(12) United States Patent
Roesler et al.

(10) Patent No.: US 7,160,988 B1
(45) Date of Patent: Jan. 9, 2007

(54) ALTERING PROTEIN FUNCTIONAL PROPERTIES THROUGH TERMINAL FUSIONS

(75) Inventors: Keith R. Roesler, Urbandale, IA (US); Jennifer K. Barry, Ames, IA (US); Aragula Gururaj Rao, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 271 days.

(21) Appl. No.: 10/795,062

(22) Filed: Mar. 5, 2004

Related U.S. Application Data

(60) Provisional application No. 60/453,132, filed on Mar. 7, 2003.

(51) Int. Cl.
*A61K 47/42* (2006.01)
*C12P 21/00* (2006.01)

(52) U.S. Cl. .................. 530/387.3; 530/300; 530/350; 424/192.1

(58) Field of Classification Search ................ 530/300, 530/350, 387.3; 424/192.1
See application file for complete search history.

(56) References Cited

U.S. PATENT DOCUMENTS 5,710,365 A    1/1998   Kerr et al.

OTHER PUBLICATIONS

Utsumi et al., Structure-function Relationships of Soybean Proteins Revealed by Usining Recombinant Systems Enzyme and Microbial Technology, 2002, vol. 30, pp. 284-288.*
Beardslee et al., Soybean Glycinin G1 Acidic Chain Shares IgE Epitopes with Peanut Allergen Ara h3 Allergy and Immunology, 2000, vol. 123, pp. 299-307.*
Gidamis et al., Modification Tolerability of Soybean Proglycinin, Biosci, Biotech, Biochem. (1995) 59(8): 1593-1595.
Jung et al., Site-Specific Limited Proteolysis of Legumin Chloramphenicol Acetyl Transferase Fusions in Vitro and In Transgenic Tobacco Seeds, Journal of Experimental Botany (1993) 44:343-349.
Kim et al., Improvement of nutritional value and funcation properties of soybean glycinin by protein engineering, Protein Enginerring (1990) 3(8):725-731.
Utsumi et al., Synthesis, processing and accumulationof modified glycinins of soybean in the seeds, leaves and stems of transgenic tobacco, Plant Science (1993) 92: 1991-202.
Utsumi et al., Effects of Deletion of Disulfide Bonds by Protein Engineering on the Confirmation and Functional Properties of Soybean Proglycinin, J. Agric. Food Chem. (1993) 41:687-691.
Utsumi et al., Structure-function relationships of soybean proteins revealed by using recombinant systems, Enzyme and Microbial Technology (2002) 30:284-288.

* cited by examiner

*Primary Examiner*—Jon Weber
*Assistant Examiner*—Samuel W. Liu
(74) *Attorney, Agent, or Firm*—Pioneer Hi-Bred International, Inc.; Kathryn K. Lappegard

(57) ABSTRACT

We disclose isolated terminal fusion polypeptides comprising a soybean glycinin or proglycinin polypeptide operably linked to the peptide of SEQ ID NO:12.

4 Claims, No Drawings

SEQUENCE LISTING

<160> NUMBER OF SEQ ID NOS: 40

<210> SEQ ID NO 1

<211> LENGTH: 1428
<212> TYPE: DNA
<213> ORGANISM: Glycine Max
<220> FEATURE:
<221> NAME/KEY: CDS
<222> LOCATION: (1)...(1428)
<223> OTHER INFORMATION: Gly1 unmodified

<400> SEQUENCE: 1

| | | | | | | | | | | | | | | | | |
|---|---|---|---|---|---|---|---|---|---|---|---|---|---|---|---|---|
| atg | ggt | tcc | aga | gag | cag | cct | cag | caa | aac | gag | tgc | cag | atc | caa | aaa | 48 |
| Met | Gly | Ser | Arg | Glu | Gln | Pro | Gln | Gln | Asn | Glu | Cys | Gln | Ile | Gln | Lys | |
| 1 | | | 5 | | | | | 10 | | | | | 15 | | | |
| ctc | aat | gcc | ctc | aaa | ccg | gat | aac | cgt | ata | gag | tca | gaa | gga | ggg | ctc | 96 |
| Leu | Asn | Ala | Leu | Lys | Pro | Asp | Asn | Arg | Ile | Glu | Ser | Glu | Gly | Gly | Leu | |
| | | | 20 | | | | | 25 | | | | | 30 | | | |
| att | gag | aca | tgg | aac | cct | aac | aac | aag | cca | ttc | cag | tgt | gcc | ggt | gtt | 144 |
| Ile | Glu | Thr | Trp | Asn | Pro | Asn | Asn | Lys | Pro | Phe | Gln | Cys | Ala | Gly | Val | |
| | | | | 35 | | | | | 40 | | | | | 45 | | |
| gcc | ctc | tct | cgc | tgc | acc | ctc | aac | cgc | aac | gcc | ctt | cgt | aga | cct | tcc | 192 |
| Ala | Leu | Ser | Arg | Cys | Thr | Leu | Asn | Arg | Asn | Ala | Leu | Arg | Arg | Pro | Ser | |
| | 50 | | | | | 55 | | | | | 60 | | | | | |
| tac | acc | aac | ggt | ccc | cag | gaa | atc | tac | atc | caa | caa | ggt | aag | ggt | att | 240 |
| Tyr | Thr | Asn | Gly | Pro | Gln | Glu | Ile | Tyr | Ile | Gln | Gln | Gly | Lys | Gly | Ile | |
| 65 | | | | | 70 | | | | | 75 | | | | | 80 | |
| ttt | ggc | atg | ata | tac | ccg | ggt | tgt | cct | agc | aca | ttt | gaa | gag | cct | cag | 288 |
| Phe | Gly | Met | Ile | Tyr | Pro | Gly | Cys | Pro | Ser | Thr | Phe | Glu | Glu | Pro | Gln | |
| | | | | 85 | | | | | 90 | | | | | 95 | | |
| caa | cct | caa | caa | aga | gga | caa | agc | agc | aga | cca | caa | gac | cgt | cac | cag | 336 |
| Gln | Pro | Gln | Gln | Arg | Gly | Gln | Ser | Ser | Arg | Pro | Gln | Asp | Arg | His | Gln | |
| | | | 100 | | | | | 105 | | | | | 110 | | | |
| aag | atc | tat | aac | ttc | aga | gag | ggt | gat | ttg | atc | gca | gtg | cct | act | ggt | 384 |
| Lys | Ile | Tyr | Asn | Phe | Arg | Glu | Gly | Asp | Leu | Ile | Ala | Val | Pro | Thr | Gly | |
| | | | | 115 | | | | | 120 | | | | | 125 | | |
| gtt | gca | tgg | tgg | atg | tac | aac | aat | gaa | gac | act | cct | gtt | gtt | gcc | gtt | 432 |
| Val | Ala | Trp | Trp | Met | Tyr | Asn | Asn | Glu | Asp | Thr | Pro | Val | Val | Ala | Val | |
| | 130 | | | | | 135 | | | | | 140 | | | | | |
| tct | att | att | gac | acc | aac | agc | ttg | gag | aac | cag | ctc | gac | cag | atg | cct | 480 |
| Ser | Ile | Ile | Asp | Thr | Asn | Ser | Leu | Glu | Asn | Gln | Leu | Asp | Gln | Met | Pro | |
| 145 | | | | | 150 | | | | | 155 | | | | | 160 | |
| agg | aga | ttc | tat | ctt | gct | ggg | aac | caa | gag | caa | gag | ttt | cta | aaa | tat | 528 |
| Arg | Arg | Phe | Tyr | Leu | Ala | Gly | Asn | Gln | Glu | Gln | Glu | Phe | Leu | Lys | Tyr | |
| | | | | 165 | | | | | 170 | | | | | 175 | | |
| cag | caa | gag | caa | gga | ggt | cat | caa | agc | cag | aaa | gga | aag | cat | cag | caa | 576 |
| Gln | Gln | Glu | Gln | Gly | Gly | His | Gln | Ser | Gln | Lys | Gly | Lys | His | Gln | Gln | |
| | | | 180 | | | | | 185 | | | | | 190 | | | |
| gaa | gaa | gaa | aac | gaa | gga | ggc | agc | ata | ttg | agt | ggc | ttc | acc | ctg | gaa | 624 |
| Glu | Glu | Glu | Asn | Glu | Gly | Gly | Ser | Ile | Leu | Ser | Gly | Phe | Thr | Leu | Glu | |
| | | | | 195 | | | | | 200 | | | | | 205 | | |
| ttc | ttg | gaa | cat | gca | ttc | agc | gtg | gac | aag | cag | ata | gcg | aaa | aac | cta | 672 |
| Phe | Leu | Glu | His | Ala | Phe | Ser | Val | Asp | Lys | Gln | Ile | Ala | Lys | Asn | Leu | |
| | 210 | | | | | 215 | | | | | 220 | | | | | |
| caa | gga | gag | aac | gaa | ggg | gaa | gac | aag | gga | gcc | att | gtg | aca | gtg | aaa | 720 |
| Gln | Gly | Glu | Asn | Glu | Gly | Glu | Asp | Lys | Gly | Ala | Ile | Val | Thr | Val | Lys | |
| 225 | | | | | 230 | | | | | 235 | | | | | 240 | |
| gga | ggt | ctg | agc | gtg | tta | aaa | cca | ccc | acg | gac | gag | cag | caa | caa | aga | 768 |
| Gly | Gly | Leu | Ser | Val | Leu | Lys | Pro | Pro | Thr | Asp | Glu | Gln | Gln | Gln | Arg | |
| | | | | 245 | | | | | 250 | | | | | 255 | | |
| ccc | cag | gaa | gag | gaa | gaa | gaa | gaa | gag | gat | gag | aag | cca | cag | tgc | aag | 816 |
| Pro | Gln | Glu | Glu | Glu | Glu | Glu | Glu | Glu | Asp | Glu | Lys | Pro | Gln | Cys | Lys | |
| | | | 260 | | | | | 265 | | | | | 270 | | | |
| ggt | aaa | gac | aaa | cac | tgc | caa | cgc | ccc | cga | gga | agc | caa | agc | aaa | agc | 864 |

```
                                                                            -continued Gly Lys Asp Lys His Cys Gln Arg Pro Arg Gly Ser Gln Ser Lys Ser
            275                 280                 285 aga aga aat ggc att gac gag acc ata tgc acc atg aga ctt cgc cac          912
Arg Arg Asn Gly Ile Asp Glu Thr Ile Cys Thr Met Arg Leu Arg His
        290                 295                 300 aac att ggc cag act tca tca cct gac atc tac aac cct caa gcc ggt          960
Asn Ile Gly Gln Thr Ser Ser Pro Asp Ile Tyr Asn Pro Gln Ala Gly
305                 310                 315                 320 agc gtc aca acc gcc acc agc ctt gac ttc cca gcc ctc tcg tgg ctc         1008
Ser Val Thr Thr Ala Thr Ser Leu Asp Phe Pro Ala Leu Ser Trp Leu
                325                 330                 335 aga ctc agt gct gag ttt gga tct ctc cgc aag aat gca atg ttc gtg         1056
Arg Leu Ser Ala Glu Phe Gly Ser Leu Arg Lys Asn Ala Met Phe Val
            340                 345                 350 cca cac tac aac ctg aac gcg aac agc ata ata tac gca ttg aat gga         1104
Pro His Tyr Asn Leu Asn Ala Asn Ser Ile Ile Tyr Ala Leu Asn Gly
        355                 360                 365 cgg gca ttg ata caa gtg gtg aat tgc aac ggt gag aga gtg ttt gat         1152
Arg Ala Leu Ile Gln Val Val Asn Cys Asn Gly Glu Arg Val Phe Asp
370                 375                 380 gga gag ctg caa gag gga cgg gtg ctg atc gtg cca caa aac ttt gtg         1200
Gly Glu Leu Gln Glu Gly Arg Val Leu Ile Val Pro Gln Asn Phe Val
385                 390                 395                 400 gtg gct gca aga tca cag agt gac aac ttc gag tat gtg tca ttc aag         1248
Val Ala Ala Arg Ser Gln Ser Asp Asn Phe Glu Tyr Val Ser Phe Lys
                405                 410                 415 acc aat gat aca ccc atg atc ggc act ctt gca ggg gca aac tca ttg         1296
Thr Asn Asp Thr Pro Met Ile Gly Thr Leu Ala Gly Ala Asn Ser Leu
            420                 425                 430 ttg aac gca tta cca gag gaa gtg att cag cac act ttc aac cta aaa         1344
Leu Asn Ala Leu Pro Glu Glu Val Ile Gln His Thr Phe Asn Leu Lys
        435                 440                 445 agc cag cag gcc agg cag ata aag aac aac aac cct ttc aag ttc ctg         1392
Ser Gln Gln Ala Arg Gln Ile Lys Asn Asn Asn Pro Phe Lys Phe Leu
450                 455                 460 gtt cca cct cag gag tct cag aag aga gct gtg gct                         1428
Val Pro Pro Gln Glu Ser Gln Lys Arg Ala Val Ala
465                 470                 475

<210> SEQ ID NO 2
<211> LENGTH: 476
<212> TYPE: PRT
<213> ORGANISM: Glycine Max

<400> SEQUENCE: 2

Met Gly Ser Arg Glu Gln Pro Gln Gln Asn Glu Cys Gln Ile Gln Lys
1               5                   10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
65                  70                  75                  80

Phe Gly Met Ile Tyr Pro Gly Cys Pro Ser Thr Phe Glu Glu Pro Gln
                85                  90                  95

Gln Pro Gln Gln Arg Gly Gln Ser Ser Arg Pro Gln Asp Arg His Gln
            100                 105                 110
```

Lys Ile Tyr Asn Phe Arg Glu Gly Asp Leu Ile Ala Val Pro Thr Gly
            115                 120                 125

Val Ala Trp Met Tyr Asn Asn Glu Asp Thr Pro Val Ala Val
        130                 135                 140

Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
            165                 170                 175

Gln Gln Glu Gln Gly Gly His Gln Ser Gln Lys Gly Lys His Gln Gln
            180                 185                 190

Glu Glu Glu Asn Glu Gly Gly Ser Ile Leu Ser Gly Phe Thr Leu Glu
            195                 200                 205

Phe Leu Glu His Ala Phe Ser Val Asp Lys Gln Ile Ala Lys Asn Leu
            210                 215                 220

Gln Gly Glu Asn Glu Gly Glu Asp Lys Gly Ala Ile Val Thr Val Lys
225                 230                 235                 240

Gly Gly Leu Ser Val Leu Lys Pro Pro Thr Asp Glu Gln Gln Gln Arg
            245                 250                 255

Pro Gln Glu Glu Glu Glu Glu Asp Glu Lys Pro Gln Cys Lys
            260                 265                 270

Gly Lys Asp Lys His Cys Gln Arg Pro Arg Gly Ser Gln Ser Lys Ser
            275                 280                 285

Arg Arg Asn Gly Ile Asp Glu Thr Ile Cys Thr Met Arg Leu Arg His
            290                 295                 300

Asn Ile Gly Gln Thr Ser Ser Pro Asp Ile Tyr Asn Pro Gln Ala Gly
305                 310                 315                 320

Ser Val Thr Thr Ala Thr Ser Leu Asp Phe Pro Ala Leu Ser Trp Leu
            325                 330                 335

Arg Leu Ser Ala Glu Phe Gly Ser Leu Arg Lys Asn Ala Met Phe Val
            340                 345                 350

Pro His Tyr Asn Leu Asn Ala Asn Ser Ile Ile Tyr Ala Leu Asn Gly
            355                 360                 365

Arg Ala Leu Ile Gln Val Val Asn Cys Asn Gly Glu Arg Val Phe Asp
            370                 375                 380

Gly Glu Leu Gln Glu Gly Arg Val Leu Ile Val Pro Gln Asn Phe Val
385                 390                 395                 400

Val Ala Ala Arg Ser Gln Ser Asp Asn Phe Glu Tyr Val Ser Phe Lys
            405                 410                 415

Thr Asn Asp Thr Pro Met Ile Gly Thr Leu Ala Gly Ala Asn Ser Leu
            420                 425                 430

Leu Asn Ala Leu Pro Glu Glu Val Ile Gln His Thr Phe Asn Leu Lys
            435                 440                 445

Ser Gln Gln Ala Arg Gln Ile Lys Asn Asn Pro Phe Lys Phe Leu
            450                 455                 460

Val Pro Pro Gln Glu Ser Gln Lys Arg Ala Val Ala
465                 470                 475

<210> SEQ ID NO 3
<211> LENGTH: 1422
<212> TYPE: DNA
<213> ORGANISM: Glycine max
<220> FEATURE:
<221> NAME/KEY: CDS
<222> LOCATION: (1)...(1422)
<223> OTHER INFORMATION: modified 5' end

<400> SEQUENCE: 3

| | | | | | | | | | | | | | | | | |
|---|---|---|---|---|---|---|---|---|---|---|---|---|---|---|---|---|
| tcc | aga | gag | cag | cct | cag | caa | aac | gag | tgc | cag | atc | caa | aaa | ctc | aat | 48 |
| Ser | Arg | Glu | Gln | Pro | Gln | Gln | Asn | Glu | Cys | Gln | Ile | Gln | Lys | Leu | Asn | |
| 1 | | | | 5 | | | | | 10 | | | | | 15 | | |
| gcc | ctc | aaa | ccg | gat | aac | cgt | ata | gag | tca | gaa | gga | ggg | ctc | att | gag | 96 |
| Ala | Leu | Lys | Pro | Asp | Asn | Arg | Ile | Glu | Ser | Glu | Gly | Gly | Leu | Ile | Glu | |
| | | | 20 | | | | | 25 | | | | | 30 | | | |
| aca | tgg | aac | cct | aac | aac | aag | cca | ttc | cag | tgt | gcc | ggt | gtt | gcc | ctc | 144 |
| Thr | Trp | Asn | Pro | Asn | Asn | Lys | Pro | Phe | Gln | Cys | Ala | Gly | Val | Ala | Leu | |
| | | 35 | | | | | 40 | | | | | 45 | | | | |
| tct | cgc | tgc | acc | ctc | aac | cgc | aac | gcc | ctt | cgt | aga | cct | tcc | tac | acc | 192 |
| Ser | Arg | Cys | Thr | Leu | Asn | Arg | Asn | Ala | Leu | Arg | Arg | Pro | Ser | Tyr | Thr | |
| | 50 | | | | | 55 | | | | | 60 | | | | | |
| aac | ggt | ccc | cag | gaa | atc | tac | atc | caa | caa | ggt | aag | ggt | att | ttt | ggc | 240 |
| Asn | Gly | Pro | Gln | Glu | Ile | Tyr | Ile | Gln | Gln | Gly | Lys | Gly | Ile | Phe | Gly | |
| 65 | | | | | 70 | | | | | 75 | | | | | 80 | |
| atg | ata | tac | ccg | ggt | tgt | cct | agc | aca | ttt | gaa | gag | cct | cag | caa | cct | 288 |
| Met | Ile | Tyr | Pro | Gly | Cys | Pro | Ser | Thr | Phe | Glu | Glu | Pro | Gln | Gln | Pro | |
| | | | | 85 | | | | | 90 | | | | | 95 | | |
| caa | caa | aga | gga | caa | agc | agc | aga | cca | caa | gac | cgt | cac | cag | aag | atc | 336 |
| Gln | Gln | Arg | Gly | Gln | Ser | Ser | Arg | Pro | Gln | Asp | Arg | His | Gln | Lys | Ile | |
| | | | 100 | | | | | 105 | | | | | 110 | | | |
| tat | aac | ttc | aga | gag | ggt | gat | ttg | atc | gca | gtg | cct | act | ggt | gtt | gca | 384 |
| Tyr | Asn | Phe | Arg | Glu | Gly | Asp | Leu | Ile | Ala | Val | Pro | Thr | Gly | Val | Ala | |
| | | 115 | | | | | 120 | | | | | 125 | | | | |
| tgg | tgg | atg | tac | aac | aat | gaa | gac | act | cct | gtt | gtt | gcc | gtt | tct | att | 432 |
| Trp | Trp | Met | Tyr | Asn | Asn | Glu | Asp | Thr | Pro | Val | Val | Ala | Val | Ser | Ile | |
| | 130 | | | | | 135 | | | | | 140 | | | | | |
| att | gac | acc | aac | agc | ttg | gag | aac | cag | ctc | gac | cag | atg | cct | agg | aga | 480 |
| Ile | Asp | Thr | Asn | Ser | Leu | Glu | Asn | Gln | Leu | Asp | Gln | Met | Pro | Arg | Arg | |
| 145 | | | | | 150 | | | | | 155 | | | | | 160 | |
| ttc | tat | ctt | gct | ggg | aac | caa | gag | caa | gag | ttt | cta | aaa | tat | cag | caa | 528 |
| Phe | Tyr | Leu | Ala | Gly | Asn | Gln | Glu | Gln | Glu | Phe | Leu | Lys | Tyr | Gln | Gln | |
| | | | | 165 | | | | | 170 | | | | | 175 | | |
| gag | caa | gga | ggt | cat | caa | agc | cag | aaa | gga | aag | cat | cag | caa | gaa | gaa | 576 |
| Glu | Gln | Gly | Gly | His | Gln | Ser | Gln | Lys | Gly | Lys | His | Gln | Gln | Glu | Glu | |
| | | | 180 | | | | | 185 | | | | | 190 | | | |
| gaa | aac | gaa | gga | ggc | agc | ata | ttg | agt | ggc | ttc | acc | ctg | gaa | ttc | ttg | 624 |
| Glu | Asn | Glu | Gly | Gly | Ser | Ile | Leu | Ser | Gly | Phe | Thr | Leu | Glu | Phe | Leu | |
| | | 195 | | | | | 200 | | | | | 205 | | | | |
| gaa | cat | gca | ttc | agc | gtg | gac | aag | cag | ata | gcg | aaa | aac | cta | caa | gga | 672 |
| Glu | His | Ala | Phe | Ser | Val | Asp | Lys | Gln | Ile | Ala | Lys | Asn | Leu | Gln | Gly | |
| | 210 | | | | | 215 | | | | | 220 | | | | | |
| gag | aac | gaa | ggg | gaa | gac | aag | gga | gcc | att | gtg | aca | gtg | aaa | gga | ggt | 720 |
| Glu | Asn | Glu | Gly | Glu | Asp | Lys | Gly | Ala | Ile | Val | Thr | Val | Lys | Gly | Gly | |
| 225 | | | | | 230 | | | | | 235 | | | | | 240 | |
| ctg | agc | gtg | tta | aaa | cca | ccc | acg | gac | gag | cag | caa | caa | aga | ccc | cag | 768 |
| Leu | Ser | Val | Leu | Lys | Pro | Pro | Thr | Asp | Glu | Gln | Gln | Gln | Arg | Pro | Gln | |
| | | | | 245 | | | | | 250 | | | | | 255 | | |
| gaa | gag | gaa | gaa | gaa | gaa | gag | gat | gag | aag | cca | cag | tgc | aag | ggt | aaa | 816 |
| Glu | Glu | Glu | Glu | Glu | Glu | Glu | Asp | Glu | Lys | Pro | Gln | Cys | Lys | Gly | Lys | |
| | | | | 260 | | | | | 265 | | | | | 270 | | |
| gac | aaa | cac | tgc | caa | cgc | ccc | cga | gga | agc | caa | agc | aaa | agc | aga | aga | 864 |
| Asp | Lys | His | Cys | Gln | Arg | Pro | Arg | Gly | Ser | Gln | Ser | Lys | Ser | Arg | Arg | |
| | | 275 | | | | | 280 | | | | | 285 | | | | |
| aat | ggc | att | gac | gag | acc | ata | tgc | acc | atg | aga | ctt | cgc | cac | aac | att | 912 |
| Asn | Gly | Ile | Asp | Glu | Thr | Ile | Cys | Thr | Met | Arg | Leu | Arg | His | Asn | Ile | |
| | 290 | | | | | 295 | | | | | 300 | | | | | |

-continued

```
ggc cag act tca tca cct gac atc tac aac cct caa gcc ggt agc gtc      960
Gly Gln Thr Ser Ser Pro Asp Ile Tyr Asn Pro Gln Ala Gly Ser Val
305                 310                 315                 320 aca acc gcc acc agc ctt gac ttc cca gcc ctc tcg tgg ctc aga ctc     1008
Thr Thr Ala Thr Ser Leu Asp Phe Pro Ala Leu Ser Trp Leu Arg Leu
            325                 330                 335 agt gct gag ttt gga tct ctc cgc aag aat gca atg ttc gtg cca cac     1056
Ser Ala Glu Phe Gly Ser Leu Arg Lys Asn Ala Met Phe Val Pro His
340                 345                 350 tac aac ctg aac gcg aac agc ata ata tac gca ttg aat gga cgg gca     1104
Tyr Asn Leu Asn Ala Asn Ser Ile Ile Tyr Ala Leu Asn Gly Arg Ala
        355                 360                 365 ttg ata caa gtg gtg aat tgc aac ggt gag aga gtg ttt gat gga gag     1152
Leu Ile Gln Val Val Asn Cys Asn Gly Glu Arg Val Phe Asp Gly Glu
    370                 375                 380 ctg caa gag gga cgg gtg ctg atc gtg cca caa aac ttt gtg gtg gct     1200
Leu Gln Glu Gly Arg Val Leu Ile Val Pro Gln Asn Phe Val Val Ala
385                 390                 395                 400 gca aga tca cag agt gac aac ttc gag tat gtg tca ttc aag acc aat     1248
Ala Arg Ser Gln Ser Asp Asn Phe Glu Tyr Val Ser Phe Lys Thr Asn
            405                 410                 415 gat aca ccc atg atc ggc act ctt gca ggg gca aac tca ttg ttg aac     1296
Asp Thr Pro Met Ile Gly Thr Leu Ala Gly Ala Asn Ser Leu Leu Asn
        420                 425                 430 gca tta cca gag gaa gtg att cag cac act ttc aac cta aaa agc cag     1344
Ala Leu Pro Glu Glu Val Ile Gln His Thr Phe Asn Leu Lys Ser Gln
    435                 440                 445 cag gcc agg cag ata aag aac aac aac cct ttc aag ttc ctg gtt cca     1392
Gln Ala Arg Gln Ile Lys Asn Asn Asn Pro Phe Lys Phe Leu Val Pro
450                 455                 460 cct cag gag tct cag aag aga gct gtg gct                             1422
Pro Gln Glu Ser Gln Lys Arg Ala Val Ala
465                 470
```

<210> SEQ ID NO 4
<211> LENGTH: 474
<212> TYPE: PRT
<213> ORGANISM: Glycine max

<400> SEQUENCE: 4

```
Ser Arg Glu Gln Pro Gln Gln Asn Glu Cys Gln Ile Gln Lys Leu Asn
1               5                   10                  15

Ala Leu Lys Pro Asp Asn Arg Ile Glu Ser Glu Gly Gly Leu Ile Glu
            20                  25                  30

Thr Trp Asn Pro Asn Asn Lys Pro Phe Gln Cys Ala Gly Val Ala Leu
        35                  40                  45

Ser Arg Cys Thr Leu Asn Arg Asn Ala Leu Arg Arg Pro Ser Tyr Thr
    50                  55                  60

Asn Gly Pro Gln Glu Ile Tyr Ile Gln Gln Gly Lys Gly Ile Phe Gly
65                  70                  75                  80

Met Ile Tyr Pro Gly Cys Pro Ser Thr Phe Glu Glu Pro Gln Gln Pro
                85                  90                  95

Gln Gln Arg Gly Gln Ser Ser Arg Pro Gln Asp Arg His Gln Lys Ile
            100                 105                 110

Tyr Asn Phe Arg Glu Gly Asp Leu Ile Ala Val Pro Thr Gly Val Ala
        115                 120                 125

Trp Trp Met Tyr Asn Asn Glu Asp Thr Pro Val Val Ala Val Ser Ile
    130                 135                 140
```

```
Ile Asp Thr Asn Ser Leu Glu Asn Gln Leu Asp Gln Met Pro Arg Arg
145                 150                 155                 160

Phe Tyr Leu Ala Gly Asn Gln Glu Gln Glu Phe Leu Lys Tyr Gln Gln
                165                 170                 175

Glu Gln Gly Gly His Gln Ser Gln Lys Gly Lys His Gln Gln Glu Glu
            180                 185                 190

Glu Asn Glu Gly Gly Ser Ile Leu Ser Gly Phe Thr Leu Glu Phe Leu
        195                 200                 205

Glu His Ala Phe Ser Val Asp Lys Gln Ile Ala Lys Asn Leu Gln Gly
    210                 215                 220

Glu Asn Glu Gly Glu Asp Lys Gly Ala Ile Val Thr Val Lys Gly Gly
225                 230                 235                 240

Leu Ser Val Leu Lys Pro Pro Thr Asp Glu Gln Gln Gln Arg Pro Gln
                245                 250                 255

Glu Glu Glu Glu Glu Glu Asp Glu Lys Pro Gln Cys Lys Gly Lys
            260                 265                 270

Asp Lys His Cys Gln Arg Pro Arg Gly Ser Gln Ser Lys Ser Arg Arg
            275                 280                 285

Asn Gly Ile Asp Glu Thr Ile Cys Thr Met Arg Leu Arg His Asn Ile
290                 295                 300

Gly Gln Thr Ser Ser Pro Asp Ile Tyr Asn Pro Gln Ala Gly Ser Val
305                 310                 315                 320

Thr Thr Ala Thr Ser Leu Asp Phe Pro Ala Leu Ser Trp Leu Arg Leu
                325                 330                 335

Ser Ala Glu Phe Gly Ser Leu Arg Lys Asn Ala Met Phe Val Pro His
            340                 345                 350

Tyr Asn Leu Asn Ala Asn Ser Ile Ile Tyr Ala Leu Asn Gly Arg Ala
        355                 360                 365

Leu Ile Gln Val Val Asn Cys Asn Gly Glu Arg Val Phe Asp Gly Glu
    370                 375                 380

Leu Gln Glu Gly Arg Val Leu Ile Val Pro Gln Asn Phe Val Val Ala
385                 390                 395                 400

Ala Arg Ser Gln Ser Asp Asn Phe Glu Tyr Val Ser Phe Lys Thr Asn
                405                 410                 415

Asp Thr Pro Met Ile Gly Thr Leu Ala Gly Ala Asn Ser Leu Leu Asn
            420                 425                 430

Ala Leu Pro Glu Glu Val Ile Gln His Thr Phe Asn Leu Lys Ser Gln
        435                 440                 445

Gln Ala Arg Gln Ile Lys Asn Asn Asn Pro Phe Lys Phe Leu Val Pro
    450                 455                 460

Pro Gln Glu Ser Gln Lys Arg Ala Val Ala
465                 470

<210> SEQ ID NO 5
<211> LENGTH: 10
<212> TYPE: PRT
<213> ORGANISM: Artificial Sequence
<220> FEATURE:
<223> OTHER INFORMATION: basic N-terminal fusion peptide

<400> SEQUENCE: 5

Met Ala Lys Arg Lys Arg Lys Arg Gly Ser
 1               5                  10

<210> SEQ ID NO 6
<211> LENGTH: 10
```

```
<212> TYPE: PRT
<213> ORGANISM: Artificial Sequence
<220> FEATURE:
<223> OTHER INFORMATION: acidic N-terminal fusion peptide

<400> SEQUENCE: 6

Met Ala Asp Glu Asp Glu Asp Glu Gly Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: acidic N-terminal fusion peptide

<400> SEQUENCE: 7

Met Ala His His His His His His Gly Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: 3 basic/3 acidic N-terminal fusion peptide

<400> SEQUENCE: 8

Met Ala Lys Glu Lys Glu Lys Glu Gly Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: hydrophilic uncharged N-terminal fusion peptide

<400> SEQUENCE: 9

Met Ala Ser Gln Ser Gln Ser Gln Gly Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: weakly hydrophobic N-terminal fusion peptide

<400> SEQUENCE: 10

Met Ala Ala Ala Ala Ala Ala Ser Gly Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: strongly hydrophobic N-terminal fusion peptide

<400> SEQUENCE: 11

Met Ala Ile Ile Ile Ile Ile Ile Gly Ser
1               5                   10

<210> SEQ ID NO 12
<211> LENGTH: 10
<212> TYPE: PRT
```

```
<213> ORGANISM: Artificial Sequence
<220> FEATURE:
<223> OTHER INFORMATION: basic C-terminal fusion peptide

<400> SEQUENCE: 12

Gly Gly Gly Ser Lys Arg Lys Arg Lys Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Acidic C-terminal fusion peptide

<400> SEQUENCE: 13

Gly Gly Gly Ser Asp Glu Asp Glu Asp Glu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Basic C-terminal fusion peptide

<400> SEQUENCE: 14

Gly Gly Gly Ser His His His His His His
1               5                   10

<210> SEQ ID NO 15
<211> LENGTH: 10
<212> TYPE: PRT
<213> ORGANISM: Artificial Sequence
<220> FEATURE:
<223> OTHER INFORMATION: 3 acidic/3 basic C-terminal fusion peptide

<400> SEQUENCE: 15

Gly Gly Gly Ser Lys Glu Lys Glu Lys Glu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: hydrophilic uncharged C-terminal fusion peptide

<400> SEQUENCE: 16

Gly Gly Gly Ser Ser Gln Ser Gln Ser Gln
1               5                   10

<210> SEQ ID NO 17
<211> LENGTH: 10
<212> TYPE: PRT
<213> ORGANISM: Artificial Sequence
<220> FEATURE:
<223> OTHER INFORMATION: weakly hydrophobic C-terminal fusion peptide

<400> SEQUENCE: 17

Gly Gly Gly Ser Ala Ala Ala Ala Ala Ala
1               5                   10

<210> SEQ ID NO 18
<211> LENGTH: 10
<212> TYPE: PRT
<213> ORGANISM: Artificial Sequence
```

-continued

```
<220> FEATURE:
<223> OTHER INFORMATION: strongly hydrophobic C-terminal fusion peptide

<400> SEQUENCE: 18

Gly Gly Gly Ser Ile Ile Ile Ile Ile
 1               5                10

<210> SEQ ID NO 19
<220> FEATURE:
<223> OTHER INFORMATION: linker sequence

<400> SEQUENCE: 19

000

<210> SEQ ID NO 20
<211> LENGTH: 1800
<212> TYPE: DNA
<213> ORGANISM: Glycine max
<220> FEATURE:
<221> NAME/KEY: CDS
<222> LOCATION: (1)...(1800)

<400> SEQUENCE: 20
```

| | | | | | | | | | | | | | | | | |
|---|---|---|---|---|---|---|---|---|---|---|---|---|---|---|---|---|
| atg | gct | gaa | gtg | gaa | gag | gga | cag | gtc | atc | ggc | gtc | cac | acc | gtt | gat | 48 |
| Met | Ala | Glu | Val | Glu | Glu | Gly | Gln | Val | Ile | Gly | Val | His | Thr | Val | Asp | |
| 1 | | | | 5 | | | | | 10 | | | | | 15 | | |
| gag | tgg | aag | ctg | caa | ctc | cag | aat | gca | aaa | gac | tcc | aaa | aaa | ctg | att | 96 |
| Glu | Trp | Lys | Leu | Gln | Leu | Gln | Asn | Ala | Lys | Asp | Ser | Lys | Lys | Leu | Ile | |
| | | | 20 | | | | | 25 | | | | | 30 | | | |
| gtg | gtg | gat | ttt | act | gct | tcc | tgg | tct | ggt | cca | tgc | cgt | ttt | atg | gcc | 144 |
| Val | Val | Asp | Phe | Thr | Ala | Ser | Trp | Ser | Gly | Pro | Cys | Arg | Phe | Met | Ala | |
| | 35 | | | | | 40 | | | | | 45 | | | | | |
| cca | gtt | ctt | gca | gag | att | gca | aag | aaa | act | cct | gaa | ttg | atc | ttc | ctc | 192 |
| Pro | Val | Leu | Ala | Glu | Ile | Ala | Lys | Lys | Thr | Pro | Glu | Leu | Ile | Phe | Leu | |
| 50 | | | | | 55 | | | | | 60 | | | | | | |
| aaa | gtg | gat | gtg | gat | gaa | gtg | agg | cct | gtt | gct | gag | gaa | tat | tcc | att | 240 |
| Lys | Val | Asp | Val | Asp | Glu | Val | Arg | Pro | Val | Ala | Glu | Glu | Tyr | Ser | Ile | |
| 65 | | | | | 70 | | | | | 75 | | | | | 80 | |
| gag | gcc | atg | cca | acc | ttc | ctc | ttc | ttg | aaa | gat | ggc | gag | atc | gtg | gac | 288 |
| Glu | Ala | Met | Pro | Thr | Phe | Leu | Phe | Leu | Lys | Asp | Gly | Glu | Ile | Val | Asp | |
| | | | | 85 | | | | | 90 | | | | | 95 | | |
| aag | gtg | gtt | ggt | gct | agt | aag | gat | gac | ctt | caa | gcc | acc | ata | gcc | aag | 336 |
| Lys | Val | Val | Gly | Ala | Ser | Lys | Asp | Asp | Leu | Gln | Ala | Thr | Ile | Ala | Lys | |
| | | | 100 | | | | | 105 | | | | | 110 | | | |
| cat | gca | tct | gct | gtt | gct | gct | gct | tct | tct | tct | gtc | atg | ggt | tcc | aga | 384 |
| His | Ala | Ser | Ala | Val | Ala | Ala | Ala | Ser | Ser | Ser | Val | Met | Gly | Ser | Arg | |
| | 115 | | | | | 120 | | | | | 125 | | | | | |
| gag | cag | cct | cag | caa | aac | gag | tgc | cag | atc | caa | aaa | ctc | aat | gcc | ctc | 432 |
| Glu | Gln | Pro | Gln | Gln | Asn | Glu | Cys | Gln | Ile | Gln | Lys | Leu | Asn | Ala | Leu | |
| 130 | | | | | 135 | | | | | 140 | | | | | | |
| aaa | ccg | gat | aac | cgt | ata | gag | tca | gaa | gga | ggg | ctc | att | gag | aca | tgg | 480 |
| Lys | Pro | Asp | Asn | Arg | Ile | Glu | Ser | Glu | Gly | Gly | Leu | Ile | Glu | Thr | Trp | |
| 145 | | | | | 150 | | | | | 155 | | | | | 160 | |
| aac | cct | aac | aac | aag | cca | ttc | cag | tgt | gcc | ggt | gtt | gcc | ctc | tct | cgc | 528 |
| Asn | Pro | Asn | Asn | Lys | Pro | Phe | Gln | Cys | Ala | Gly | Val | Ala | Leu | Ser | Arg | |
| | | | | 165 | | | | | 170 | | | | | 175 | | |
| tgc | acc | ctc | aac | cgc | aac | gcc | ctt | cgt | aga | cct | tcc | tac | acc | aac | ggt | 576 |
| Cys | Thr | Leu | Asn | Arg | Asn | Ala | Leu | Arg | Arg | Pro | Ser | Tyr | Thr | Asn | Gly | |
| | | | 180 | | | | | 185 | | | | | 190 | | | |
| ccc | cag | gaa | atc | tac | atc | caa | caa | ggt | aag | ggt | att | ttt | ggc | atg | ata | 624 |
| Pro | Gln | Glu | Ile | Tyr | Ile | Gln | Gln | Gly | Lys | Gly | Ile | Phe | Gly | Met | Ile | |
| | 195 | | | | | 200 | | | | | 205 | | | | | |

-continued

```
tac ccg ggt tgt cct agc aca ttt gaa gag cct cag caa cct caa caa    672
Tyr Pro Gly Cys Pro Ser Thr Phe Glu Glu Pro Gln Gln Pro Gln Gln
    210                 215                 220 aga gga caa agc agc aga cca caa gac cgt cac cag aag atc tat aac    720
Arg Gly Gln Ser Ser Arg Pro Gln Asp Arg His Gln Lys Ile Tyr Asn
225                 230                 235                 240 ttc aga gag ggt gat ttg atc gca gtg cct act ggt gtt gca tgg tgg    768
Phe Arg Glu Gly Asp Leu Ile Ala Val Pro Thr Gly Val Ala Trp Trp
                245                 250                 255 atg tac aac aat gaa gac act cct gtt gtt gcc gtt tct att att gac    816
Met Tyr Asn Asn Glu Asp Thr Pro Val Val Ala Val Ser Ile Ile Asp
            260                 265                 270 acc aac agc ttg gag aac cag ctc gac cag atg cct agg aga ttc tat    864
Thr Asn Ser Leu Glu Asn Gln Leu Asp Gln Met Pro Arg Arg Phe Tyr
        275                 280                 285 ctt gct ggg aac caa gag caa gag ttt cta aaa tat cag caa gag caa    912
Leu Ala Gly Asn Gln Glu Gln Glu Phe Leu Lys Tyr Gln Gln Glu Gln
    290                 295                 300 gga ggt cat caa agc cag aaa gga aag cat cag caa gaa gaa gaa aac    960
Gly Gly His Gln Ser Gln Lys Gly Lys His Gln Gln Glu Glu Glu Asn
305                 310                 315                 320 gaa gga ggc agc ata ttg agt ggc ttc acc ctg gaa ttc ttg gaa cat   1008
Glu Gly Gly Ser Ile Leu Ser Gly Phe Thr Leu Glu Phe Leu Glu His
                325                 330                 335 gca ttc agc gtg gac aag cag ata gcg aaa aac cta caa gga gag aac   1056
Ala Phe Ser Val Asp Lys Gln Ile Ala Lys Asn Leu Gln Gly Glu Asn
            340                 345                 350 gaa ggg gaa gac aag gga gcc att gtg aca gtg aaa gga ggt ctg agc   1104
Glu Gly Glu Asp Lys Gly Ala Ile Val Thr Val Lys Gly Gly Leu Ser
        355                 360                 365 gtg tta aaa cca ccc acg gac gag cag caa caa aga ccc cag gaa gag   1152
Val Leu Lys Pro Pro Thr Asp Glu Gln Gln Gln Arg Pro Gln Glu Glu
370                 375                 380 gaa gaa gaa gaa gag gat gag aag cca cag tgc aag ggt aaa gac aaa   1200
Glu Glu Glu Glu Glu Asp Glu Lys Pro Gln Cys Lys Gly Lys Asp Lys
385                 390                 395                 400 cac tgc caa cgc ccc cga gga agc caa agc aaa agc aga aga aat ggc   1248
His Cys Gln Arg Pro Arg Gly Ser Gln Ser Lys Ser Arg Arg Asn Gly
                405                 410                 415 att gac gag acc ata tgc acc atg aga ctt cgc cac aac att ggc cag   1296
Ile Asp Glu Thr Ile Cys Thr Met Arg Leu Arg His Asn Ile Gly Gln
            420                 425                 430 act tca tca cct gac atc tac aac cct caa gcc ggt agc gtc aca acc   1344
Thr Ser Ser Pro Asp Ile Tyr Asn Pro Gln Ala Gly Ser Val Thr Thr
        435                 440                 445 gcc acc agc ctt gac ttc cca gcc ctc tcg tgg ctc aga ctc agt gct   1392
Ala Thr Ser Leu Asp Phe Pro Ala Leu Ser Trp Leu Arg Leu Ser Ala
450                 455                 460 gag ttt gga tct ctc cgc aag aat gca atg ttc gtg cca cac tac aac   1440
Glu Phe Gly Ser Leu Arg Lys Asn Ala Met Phe Val Pro His Tyr Asn
465                 470                 475                 480 ctg aac gcg aac agc ata ata tac gca ttg aat gga cgg gca ttg ata   1488
Leu Asn Ala Asn Ser Ile Ile Tyr Ala Leu Asn Gly Arg Ala Leu Ile
                485                 490                 495 caa gtg gtg aat tgc aac ggt gag aga gtg ttt gat gga gag ctg caa   1536
Gln Val Val Asn Cys Asn Gly Glu Arg Val Phe Asp Gly Glu Leu Gln
            500                 505                 510 gag gga cgg gtg ctg atc gtg cca caa aac ttt gtg gtg gct gca aga   1584
Glu Gly Arg Val Leu Ile Val Pro Gln Asn Phe Val Val Ala Ala Arg
```

```
                515                 520                 525
tca cag agt gac aac ttc gag tat gtg tca ttc aag acc aat gat aca    1632
Ser Gln Ser Asp Asn Phe Glu Tyr Val Ser Phe Lys Thr Asn Asp Thr
        530                 535                 540 ccc atg atc ggc act ctt gca ggg gca aac tca ttg ttg aac gca tta    1680
Pro Met Ile Gly Thr Leu Ala Gly Ala Asn Ser Leu Leu Asn Ala Leu
545                 550                 555                 560 cca gag gaa gtg att cag cac act ttc aac cta aaa agc cag cag gcc    1728
Pro Glu Glu Val Ile Gln His Thr Phe Asn Leu Lys Ser Gln Gln Ala
                565                 570                 575 agg cag ata aag aac aac aac cct ttc aag ttc ctg gtt cca cct cag    1776
Arg Gln Ile Lys Asn Asn Asn Pro Phe Lys Phe Leu Val Pro Pro Gln
            580                 585                 590 gag tct cag aag aga gct gtg gct                                    1800
Glu Ser Gln Lys Arg Ala Val Ala
            595                 600

<210> SEQ ID NO 21
<211> LENGTH: 600
<212> TYPE: PRT
<213> ORGANISM: Glycine max

<400> SEQUENCE: 21

Met Ala Glu Val Glu Glu Gly Gln Val Ile Gly Val His Thr Val Asp
 1                5                  10                  15

Glu Trp Lys Leu Gln Leu Gln Asn Ala Lys Asp Ser Lys Lys Leu Ile
                20                  25                  30

Val Val Asp Phe Thr Ala Ser Trp Ser Gly Pro Cys Arg Phe Met Ala
            35                  40                  45

Pro Val Leu Ala Glu Ile Ala Lys Lys Thr Pro Glu Leu Ile Phe Leu
        50                  55                  60

Lys Val Asp Val Asp Glu Val Arg Pro Val Ala Glu Glu Tyr Ser Ile
65                  70                  75                  80

Glu Ala Met Pro Thr Phe Leu Phe Leu Lys Asp Gly Glu Ile Val Asp
                85                  90                  95

Lys Val Val Gly Ala Ser Lys Asp Asp Leu Gln Ala Thr Ile Ala Lys
            100                 105                 110

His Ala Ser Ala Val Ala Ala Ser Ser Ser Val Met Gly Ser Arg
        115                 120                 125

Glu Gln Pro Gln Gln Asn Glu Cys Gln Ile Gln Lys Leu Asn Ala Leu
    130                 135                 140

Lys Pro Asp Asn Arg Ile Glu Ser Glu Gly Gly Leu Ile Glu Thr Trp
145                 150                 155                 160

Asn Pro Asn Asn Lys Pro Phe Gln Cys Ala Gly Val Ala Leu Ser Arg
                165                 170                 175

Cys Thr Leu Asn Arg Asn Ala Leu Arg Arg Pro Ser Tyr Thr Asn Gly
            180                 185                 190

Pro Gln Glu Ile Tyr Ile Gln Gln Gly Lys Gly Ile Phe Gly Met Ile
        195                 200                 205

Tyr Pro Gly Cys Pro Ser Thr Phe Glu Glu Pro Gln Gln Pro Gln Gln
    210                 215                 220

Arg Gly Gln Ser Ser Arg Pro Gln Asp Arg His Gln Lys Ile Tyr Asn
225                 230                 235                 240

Phe Arg Glu Gly Asp Leu Ile Ala Val Pro Thr Gly Val Ala Trp Trp
                245                 250                 255

Met Tyr Asn Asn Glu Asp Thr Pro Val Val Ala Val Ser Ile Ile Asp
```

```
                260              265               270
Thr Asn Ser Leu Glu Asn Gln Leu Asp Gln Met Pro Arg Arg Phe Tyr
        275              280               285
Leu Ala Gly Asn Gln Glu Gln Glu Phe Leu Lys Tyr Gln Gln Glu Gln
        290              295               300
Gly Gly His Gln Ser Gln Lys Gly Lys His Gln Gln Glu Glu Glu Asn
305              310              315               320
Glu Gly Gly Ser Ile Leu Ser Gly Phe Thr Leu Glu Phe Leu Glu His
                325              330               335
Ala Phe Ser Val Asp Lys Gln Ile Ala Lys Asn Leu Gln Gly Glu Asn
        340              345               350
Glu Gly Glu Asp Lys Gly Ala Ile Val Thr Val Lys Gly Leu Ser
        355              360               365
Val Leu Lys Pro Pro Thr Asp Glu Gln Gln Gln Arg Pro Gln Glu Glu
        370              375               380
Glu Glu Glu Glu Asp Glu Lys Pro Gln Cys Lys Gly Lys Asp Lys
385              390              395               400
His Cys Gln Arg Pro Arg Gly Ser Gln Ser Lys Ser Arg Arg Asn Gly
                405              410               415
Ile Asp Glu Thr Ile Cys Thr Met Arg Leu Arg His Asn Ile Gly Gln
                420              425               430
Thr Ser Ser Pro Asp Ile Tyr Asn Pro Gln Ala Gly Ser Val Thr Thr
        435              440               445
Ala Thr Ser Leu Asp Phe Pro Ala Leu Ser Trp Leu Arg Leu Ser Ala
        450              455               460
Glu Phe Gly Ser Leu Arg Lys Asn Ala Met Phe Val Pro His Tyr Asn
465              470              475               480
Leu Asn Ala Asn Ser Ile Ile Tyr Ala Leu Asn Gly Arg Ala Leu Ile
                485              490               495
Gln Val Val Asn Cys Asn Gly Glu Arg Val Phe Asp Gly Glu Leu Gln
                500              505               510
Glu Gly Arg Val Leu Ile Val Pro Gln Asn Phe Val Val Ala Ala Arg
        515              520               525
Ser Gln Ser Asp Asn Phe Glu Tyr Val Ser Phe Lys Thr Asn Asp Thr
        530              535               540
Pro Met Ile Gly Thr Leu Ala Gly Ala Asn Ser Leu Leu Asn Ala Leu
545              550              555               560
Pro Glu Glu Val Ile Gln His Thr Phe Asn Leu Lys Ser Gln Gln Ala
                565              570               575
Arg Gln Ile Lys Asn Asn Asn Pro Phe Lys Phe Leu Val Pro Pro Gln
                580              585               590
Glu Ser Gln Lys Arg Ala Val Ala
        595              600

<210> SEQ ID NO 22
<211> LENGTH: 1854
<212> TYPE: DNA
<213> ORGANISM: Glycine max
<220> FEATURE:
<221> NAME/KEY: CDS
<222> LOCATION: (1)...(1854)

<400> SEQUENCE: 22 atg gca tcc cat agg caa agc tat gaa gct ggt caa act aag ggc cga    48
Met Ala Ser His Arg Gln Ser Tyr Glu Ala Gly Gln Thr Lys Gly Arg
 1               5                  10                  15
```

```
act gag gaa aag acg aac cag acg atg ggc aat att gga gag aag gct         96
Thr Glu Glu Lys Thr Asn Gln Thr Met Gly Asn Ile Gly Glu Lys Ala
             20                  25                  30 caa gct gca aag gag aag acc cag gaa atg gcc caa gct gca aag gag        144
Gln Ala Ala Lys Glu Lys Thr Gln Glu Met Ala Gln Ala Ala Lys Glu
         35                  40                  45 aag acc caa caa aca gcc caa gct gcc aag gac aag act tgc gac act        192
Lys Thr Gln Gln Thr Ala Gln Ala Ala Lys Asp Lys Thr Cys Asp Thr
     50                  55                  60 tcc caa gcg gca aag gag aag acc caa cag aat aca gga gct gct caa        240
Ser Gln Ala Ala Lys Glu Lys Thr Gln Gln Asn Thr Gly Ala Ala Gln
 65                  70                  75                  80 caa aag acc tca gag atg ggc cag tcc acg aag gaa tcg gcc cag tca        288
Gln Lys Thr Ser Glu Met Gly Gln Ser Thr Lys Glu Ser Ala Gln Ser
                 85                  90                  95 ggg aag gac aac acc caa ggg ttc ctg cag cag aca ggg gag aag gtg        336
Gly Lys Asp Asn Thr Gln Gly Phe Leu Gln Gln Thr Gly Glu Lys Val
            100                 105                 110 aag ggc gca gcc caa ggt gct aca gag gct gtg aag caa acc ctt ggc        384
Lys Gly Ala Ala Gln Gly Ala Thr Glu Ala Val Lys Gln Thr Leu Gly
        115                 120                 125 ttg ggc gaa cat gat caa gac caa cgc aga cag tac ggt ggt gga tcc        432
Leu Gly Glu His Asp Gln Asp Gln Arg Arg Gln Tyr Gly Gly Gly Ser
    130                 135                 140 tcc aga gag cag cct cag caa aac gag tgc cag atc caa aaa ctc aat        480
Ser Arg Glu Gln Pro Gln Gln Asn Glu Cys Gln Ile Gln Lys Leu Asn
145                 150                 155                 160 gcc ctc aaa ccg gat aac cgt ata gag tca gaa gga ggg ctc att gag        528
Ala Leu Lys Pro Asp Asn Arg Ile Glu Ser Glu Gly Gly Leu Ile Glu
                165                 170                 175 aca tgg aac cct aac aac aag cca ttc cag tgt gcc ggt gtt gcc ctc        576
Thr Trp Asn Pro Asn Asn Lys Pro Phe Gln Cys Ala Gly Val Ala Leu
            180                 185                 190 tct cgc tgc acc ctc aac cgc aac gcc ctt cgt aga cct tcc tac acc        624
Ser Arg Cys Thr Leu Asn Arg Asn Ala Leu Arg Arg Pro Ser Tyr Thr
        195                 200                 205 aac ggt ccc cag gaa atc tac atc caa caa ggt aag ggt att ttt ggc        672
Asn Gly Pro Gln Glu Ile Tyr Ile Gln Gln Gly Lys Gly Ile Phe Gly
    210                 215                 220 atg ata tac ccg ggt tgt cct agc aca ttt gaa gag cct cag caa cct        720
Met Ile Tyr Pro Gly Cys Pro Ser Thr Phe Glu Glu Pro Gln Gln Pro
225                 230                 235                 240 caa caa aga gga caa agc agc aga cca caa gac cgt cac cag aag atc        768
Gln Gln Arg Gly Gln Ser Ser Arg Pro Gln Asp Arg His Gln Lys Ile
                245                 250                 255 tat aac ttc aga gag ggt gat ttg atc gca gtg cct act ggt gtt gca        816
Tyr Asn Phe Arg Glu Gly Asp Leu Ile Ala Val Pro Thr Gly Val Ala
            260                 265                 270 tgg tgg atg tac aac aat gaa gac act cct gtt gtt gcc gtt tct att        864
Trp Trp Met Tyr Asn Asn Glu Asp Thr Pro Val Val Ala Val Ser Ile
        275                 280                 285 att gac acc aac agc ttg gag aac cag ctc gac cag atg cct agg aga        912
Ile Asp Thr Asn Ser Leu Glu Asn Gln Leu Asp Gln Met Pro Arg Arg
    290                 295                 300 ttc tat ctt gct ggg aac caa gag caa gag ttt cta aaa tat cag caa        960
Phe Tyr Leu Ala Gly Asn Gln Glu Gln Glu Phe Leu Lys Tyr Gln Gln
305                 310                 315                 320 gag caa gga ggt cat caa agc cag aaa gga aag cat cag caa gaa gaa       1008
Glu Gln Gly Gly His Gln Ser Gln Lys Gly Lys His Gln Gln Glu Glu
```

```
                325                 330                 335
gaa aac gaa gga ggc agc ata ttg agt ggc ttc acc ctg gaa ttc ttg     1056
Glu Asn Glu Gly Gly Ser Ile Leu Ser Gly Phe Thr Leu Glu Phe Leu
            340                 345                 350 gaa cat gca ttc agc gtg gac aag cag ata gcg aaa aac cta caa gga     1104
Glu His Ala Phe Ser Val Asp Lys Gln Ile Ala Lys Asn Leu Gln Gly
            355                 360                 365 gag aac gaa ggg gaa gac aag gga gcc att gtg aca gtg aaa gga ggt     1152
Glu Asn Glu Gly Glu Asp Lys Gly Ala Ile Val Thr Val Lys Gly Gly
            370                 375                 380 ctg agc gtg tta aaa cca ccc acg gac gag cag caa caa aga ccc cag     1200
Leu Ser Val Leu Lys Pro Pro Thr Asp Glu Gln Gln Gln Arg Pro Gln
385                 390                 395                 400 gaa gag gaa gaa gaa gaa gag gat gag aag cca cag tgc aag ggt aaa     1248
Glu Glu Glu Glu Glu Glu Glu Asp Glu Lys Pro Gln Cys Lys Gly Lys
            405                 410                 415 gac aaa cac tgc caa cgc ccc cga gga agc caa agc aaa agc aga aga     1296
Asp Lys His Cys Gln Arg Pro Arg Gly Ser Gln Ser Lys Ser Arg Arg
            420                 425                 430 aat ggc att gac gag acc ata tgc acc atg aga ctt cgc cac aac att     1344
Asn Gly Ile Asp Glu Thr Ile Cys Thr Met Arg Leu Arg His Asn Ile
            435                 440                 445 ggc cag act tca tca cct gac atc tac aac cct caa gcc ggt agc gtc     1392
Gly Gln Thr Ser Ser Pro Asp Ile Tyr Asn Pro Gln Ala Gly Ser Val
            450                 455                 460 aca acc gcc acc agc ctt gac ttc cca gcc ctc tcg tgg ctc aga ctc     1440
Thr Thr Ala Thr Ser Leu Asp Phe Pro Ala Leu Ser Trp Leu Arg Leu
465                 470                 475                 480 agt gct gag ttt gga tct ctc cgc aag aat gca atg ttc gtg cca cac     1488
Ser Ala Glu Phe Gly Ser Leu Arg Lys Asn Ala Met Phe Val Pro His
            485                 490                 495 tac aac ctg aac gcg aac agc ata ata tac gca ttg aat gga cgg gca     1536
Tyr Asn Leu Asn Ala Asn Ser Ile Ile Tyr Ala Leu Asn Gly Arg Ala
            500                 505                 510 ttg ata caa gtg gtg aat tgc aac ggt gag aga gtg ttt gat gga gag     1584
Leu Ile Gln Val Val Asn Cys Asn Gly Glu Arg Val Phe Asp Gly Glu
            515                 520                 525 ctg caa gag gga cgg gtg ctg atc gtg cca caa aac ttt gtg gtg gct     1632
Leu Gln Glu Gly Arg Val Leu Ile Val Pro Gln Asn Phe Val Val Ala
            530                 535                 540 gca aga tca cag agt gac aac ttc gag tat gtg tca ttc aag acc aat     1680
Ala Arg Ser Gln Ser Asp Asn Phe Glu Tyr Val Ser Phe Lys Thr Asn
545                 550                 555                 560 gat aca ccc atg atc ggc act ctt gca ggg gca aac tca ttg ttg aac     1728
Asp Thr Pro Met Ile Gly Thr Leu Ala Gly Ala Asn Ser Leu Leu Asn
            565                 570                 575 gca tta cca gag gaa gtg att cag cac act ttc aac cta aaa agc cag     1776
Ala Leu Pro Glu Glu Val Ile Gln His Thr Phe Asn Leu Lys Ser Gln
            580                 585                 590 cag gcc agg cag ata aag aac aac aac cct ttc aag ttc ctg gtt cca     1824
Gln Ala Arg Gln Ile Lys Asn Asn Asn Pro Phe Lys Phe Leu Val Pro
            595                 600                 605 cct cag gag tct cag aag aga gct gtg gct                             1854
Pro Gln Glu Ser Gln Lys Arg Ala Val Ala
            610                 615
```

<210> SEQ ID NO 23
<211> LENGTH: 618
<212> TYPE: PRT
<213> ORGANISM: Glycine max -continued

<400> SEQUENCE: 23

```
Met Ala Ser His Arg Gln Ser Tyr Glu Ala Gly Gln Thr Lys Gly Arg
 1               5                  10                  15

Thr Glu Glu Lys Thr Asn Gln Thr Met Gly Asn Ile Gly Glu Lys Ala
             20                  25                  30

Gln Ala Ala Lys Glu Lys Thr Gln Glu Met Ala Gln Ala Ala Lys Glu
         35                  40                  45

Lys Thr Gln Gln Thr Ala Gln Ala Ala Lys Asp Lys Thr Cys Asp Thr
     50                  55                  60

Ser Gln Ala Ala Lys Glu Lys Thr Gln Gln Asn Thr Gly Ala Ala Gln
 65                  70                  75                  80

Gln Lys Thr Ser Glu Met Gly Gln Ser Thr Lys Glu Ser Ala Gln Ser
                 85                  90                  95

Gly Lys Asp Asn Thr Gln Gly Phe Leu Gln Gln Thr Gly Glu Lys Val
            100                 105                 110

Lys Gly Ala Ala Gln Gly Ala Thr Glu Ala Val Lys Gln Thr Leu Gly
        115                 120                 125

Leu Gly Glu His Asp Gln Asp Gln Arg Arg Gln Tyr Gly Gly Gly Ser
130                 135                 140

Ser Arg Glu Gln Pro Gln Gln Asn Glu Cys Gln Ile Gln Lys Leu Asn
145                 150                 155                 160

Ala Leu Lys Pro Asp Asn Arg Ile Glu Ser Glu Gly Gly Leu Ile Glu
                165                 170                 175

Thr Trp Asn Pro Asn Asn Lys Pro Phe Gln Cys Ala Gly Val Ala Leu
            180                 185                 190

Ser Arg Cys Thr Leu Asn Arg Asn Ala Leu Arg Arg Pro Ser Tyr Thr
        195                 200                 205

Asn Gly Pro Gln Glu Ile Tyr Ile Gln Gln Gly Lys Gly Ile Phe Gly
210                 215                 220

Met Ile Tyr Pro Gly Cys Pro Ser Thr Phe Glu Glu Pro Gln Gln Pro
225                 230                 235                 240

Gln Gln Arg Gly Gln Ser Ser Arg Pro Gln Asp Arg His Gln Lys Ile
                245                 250                 255

Tyr Asn Phe Arg Glu Gly Asp Leu Ile Ala Val Pro Thr Gly Val Ala
            260                 265                 270

Trp Trp Met Tyr Asn Asn Glu Asp Thr Pro Val Val Ala Val Ser Ile
        275                 280                 285

Ile Asp Thr Asn Ser Leu Glu Asn Gln Leu Asp Gln Met Pro Arg Arg
290                 295                 300

Phe Tyr Leu Ala Gly Asn Gln Glu Gln Glu Phe Leu Lys Tyr Gln Gln
305                 310                 315                 320

Glu Gln Gly Gly His Gln Ser Gln Lys Gly Lys His Gln Gln Glu Glu
                325                 330                 335

Glu Asn Glu Gly Gly Ser Ile Leu Ser Gly Phe Thr Leu Glu Phe Leu
            340                 345                 350

Glu His Ala Phe Ser Val Asp Lys Gln Ile Ala Lys Asn Leu Gln Gly
        355                 360                 365

Glu Asn Glu Gly Glu Asp Lys Gly Ala Ile Val Thr Val Lys Gly Gly
370                 375                 380

Leu Ser Val Leu Lys Pro Pro Thr Asp Glu Gln Gln Arg Pro Gln
385                 390                 395                 400

Glu Glu Glu Glu Glu Glu Glu Asp Glu Lys Pro Gln Cys Lys Gly Lys
```

-continued

```
                405                 410                 415
Asp Lys His Cys Gln Arg Pro Arg Gly Ser Gln Ser Lys Ser Arg Arg
                420                 425                 430

Asn Gly Ile Asp Glu Thr Ile Cys Thr Met Arg Leu Arg His Asn Ile
            435                 440                 445

Gly Gln Thr Ser Ser Pro Asp Ile Tyr Asn Pro Gln Ala Gly Ser Val
        450                 455                 460

Thr Thr Ala Thr Ser Leu Asp Phe Pro Ala Leu Ser Trp Leu Arg Leu
465                 470                 475                 480

Ser Ala Glu Phe Gly Ser Leu Arg Lys Asn Ala Met Phe Val Pro His
                485                 490                 495

Tyr Asn Leu Asn Ala Asn Ser Ile Ile Tyr Ala Leu Asn Gly Arg Ala
            500                 505                 510

Leu Ile Gln Val Val Asn Cys Asn Gly Glu Arg Val Phe Asp Gly Glu
        515                 520                 525

Leu Gln Glu Gly Arg Val Leu Ile Val Pro Gln Asn Phe Val Val Ala
    530                 535                 540

Ala Arg Ser Gln Ser Asp Asn Phe Glu Tyr Val Ser Phe Lys Thr Asn
545                 550                 555                 560

Asp Thr Pro Met Ile Gly Thr Leu Ala Gly Ala Asn Ser Leu Leu Asn
                565                 570                 575

Ala Leu Pro Glu Glu Val Ile Gln His Thr Phe Asn Leu Lys Ser Gln
            580                 585                 590

Gln Ala Arg Gln Ile Lys Asn Asn Pro Phe Lys Phe Leu Val Pro
        595                 600                 605

Pro Gln Glu Ser Gln Lys Arg Ala Val Ala
    610                 615
```

<210> SEQ ID NO 24
<211> LENGTH: 1809
<212> TYPE: DNA
<213> ORGANISM: Glycine max
<220> FEATURE:
<221> NAME/KEY: CDS
<222> LOCATION: (1)...(1809)

<400> SEQUENCE: 24

```
atg ggt tcc aga gag cag cct cag caa aac gag tgc cag atc caa aaa     48
Met Gly Ser Arg Glu Gln Pro Gln Gln Asn Glu Cys Gln Ile Gln Lys
  1               5                  10                  15 ctc aat gcc ctc aaa ccg gat aac cgt ata gag tca gaa gga ggg ctc     96
Leu Asn Ala Leu Lys Pro Asp Asn Arg Ile Glu Ser Glu Gly Gly Leu
             20                  25                  30 att gag aca tgg aac cct aac aac aag cca ttc cag tgt gcc ggt gtt    144
Ile Glu Thr Trp Asn Pro Asn Asn Lys Pro Phe Gln Cys Ala Gly Val
         35                  40                  45 gcc ctc tct cgc tgc acc ctc aac cgc aac gcc ctt cgt aga cct tcc    192
Ala Leu Ser Arg Cys Thr Leu Asn Arg Asn Ala Leu Arg Arg Pro Ser
     50                  55                  60 tac acc aac ggt ccc cag gaa atc tac atc caa caa ggt aag ggt att    240
Tyr Thr Asn Gly Pro Gln Glu Ile Tyr Ile Gln Gln Gly Lys Gly Ile
 65                  70                  75                  80 ttt ggc atg ata tac ccg ggt tgt cct agc aca ttt gaa gag cct cag    288
Phe Gly Met Ile Tyr Pro Gly Cys Pro Ser Thr Phe Glu Glu Pro Gln
                 85                  90                  95 caa cct caa caa aga gga caa agc agc aga cca caa gac cgt cac cag    336
Gln Pro Gln Gln Arg Gly Gln Ser Ser Arg Pro Gln Asp Arg His Gln
            100                 105                 110
```

-continued

| | |
|---|---|
| aag atc tat aac ttc aga gag ggt gat ttg atc gca gtg cct act ggt<br>Lys Ile Tyr Asn Phe Arg Glu Gly Asp Leu Ile Ala Val Pro Thr Gly<br>115                  120                  125 | 384 |
| gtt gca tgg tgg atg tac aac aat gaa gac act cct gtt gtt gcc gtt<br>Val Ala Trp Trp Met Tyr Asn Asn Glu Asp Thr Pro Val Val Ala Val<br>130                  135                  140 | 432 |
| tct att att gac acc aac agc ttg gag aac cag ctc gac cag atg cct<br>Ser Ile Ile Asp Thr Asn Ser Leu Glu Asn Gln Leu Asp Gln Met Pro<br>145                  150                  155                  160 | 480 |
| agg aga ttc tat ctt gct ggg aac caa gag caa gag ttt cta aaa tat<br>Arg Arg Phe Tyr Leu Ala Gly Asn Gln Glu Gln Glu Phe Leu Lys Tyr<br>165                  170                  175 | 528 |
| cag caa gag caa gga ggt cat caa agc cag aaa gga aag cat cag caa<br>Gln Gln Glu Gln Gly Gly His Gln Ser Gln Lys Gly Lys His Gln Gln<br>180                  185                  190 | 576 |
| gaa gaa gaa aac gaa gga ggc agc ata ttg agt ggc ttc acc ctg gaa<br>Glu Glu Glu Asn Glu Gly Gly Ser Ile Leu Ser Gly Phe Thr Leu Glu<br>195                  200                  205 | 624 |
| ttc ttg gaa cat gca ttc agc gtg gac aag cag ata gcg aaa aac cta<br>Phe Leu Glu His Ala Phe Ser Val Asp Lys Gln Ile Ala Lys Asn Leu<br>210                  215                  220 | 672 |
| caa gga gag aac gaa ggg gaa gac aag gga gcc att gtg aca gtg aaa<br>Gln Gly Glu Asn Glu Gly Glu Asp Lys Gly Ala Ile Val Thr Val Lys<br>225                  230                  235                  240 | 720 |
| gga ggt ctg agc gtg tta aaa cca ccc acg gac gag cag caa caa aga<br>Gly Gly Leu Ser Val Leu Lys Pro Pro Thr Asp Glu Gln Gln Gln Arg<br>245                  250                  255 | 768 |
| ccc cag gaa gag gaa gaa gaa gaa gag gat gag aag cca cag tgc aag<br>Pro Gln Glu Glu Glu Glu Glu Glu Asp Glu Lys Pro Gln Cys Lys<br>260                  265                  270 | 816 |
| ggt aaa gac aaa cac tgc caa cgc ccc cga gga agc caa agc aaa agc<br>Gly Lys Asp Lys His Cys Gln Arg Pro Arg Gly Ser Gln Ser Lys Ser<br>275                  280                  285 | 864 |
| aga aga aat ggc att gac gag acc ata tgc acc atg aga ctt cgc cac<br>Arg Arg Asn Gly Ile Asp Glu Thr Ile Cys Thr Met Arg Leu Arg His<br>290                  295                  300 | 912 |
| aac att ggc cag act tca tca cct gac atc tac aac cct caa gcc ggt<br>Asn Ile Gly Gln Thr Ser Ser Pro Asp Ile Tyr Asn Pro Gln Ala Gly<br>305                  310                  315                  320 | 960 |
| agc gtc aca acc gcc acc agc ctt gac ttc cca gcc ctc tcg tgg ctc<br>Ser Val Thr Thr Ala Thr Ser Leu Asp Phe Pro Ala Leu Ser Trp Leu<br>325                  330                  335 | 1008 |
| aga ctc agt gct gag ttt gga tct ctc cgc aag aat gca atg ttc gtg<br>Arg Leu Ser Ala Glu Phe Gly Ser Leu Arg Lys Asn Ala Met Phe Val<br>340                  345                  350 | 1056 |
| cca cac tac aac ctg aac gcg aac agc ata ata tac gca ttg aat gga<br>Pro His Tyr Asn Leu Asn Ala Asn Ser Ile Ile Tyr Ala Leu Asn Gly<br>355                  360                  365 | 1104 |
| cgg gca ttg ata caa gtg gtg aat tgc aac ggt gag aga gtg ttt gat<br>Arg Ala Leu Ile Gln Val Val Asn Cys Asn Gly Glu Arg Val Phe Asp<br>370                  375                  380 | 1152 |
| gga gag ctg caa gag gga cgg gtg ctg atc gtg cca caa aac ttt gtg<br>Gly Glu Leu Gln Glu Gly Arg Val Leu Ile Val Pro Gln Asn Phe Val<br>385                  390                  395                  400 | 1200 |
| gtg gct gca aga tca cag agt gac aac ttc gag tat gtg tca ttc aag<br>Val Ala Ala Arg Ser Gln Ser Asp Asn Phe Glu Tyr Val Ser Phe Lys<br>405                  410                  415 | 1248 |
| acc aat gat aca ccc atg atc ggc act ctt gca ggg gca aac tca ttg<br>Thr Asn Asp Thr Pro Met Ile Gly Thr Leu Ala Gly Ala Asn Ser Leu | 1296 |

-continued

```
                420                 425                 430
ttg aac gca tta cca gag gaa gtg att cag cac act ttc aac cta aaa      1344
Leu Asn Ala Leu Pro Glu Glu Val Ile Gln His Thr Phe Asn Leu Lys
        435                 440                 445 agc cag cag gcc agg cag ata aag aac aac aac cct ttc aag ttc ctg      1392
Ser Gln Gln Ala Arg Gln Ile Lys Asn Asn Asn Pro Phe Lys Phe Leu
    450                 455                 460 gtt cca cct cag gag tct cag aag aga gct gtg gct ggt ggt gga tcc      1440
Val Pro Pro Gln Glu Ser Gln Lys Arg Ala Val Ala Gly Gly Gly Ser
465                 470                 475                 480 atg gct gaa gtg gaa gag gga cag gtc atc ggc gtc cac acc gtt gat      1488
Met Ala Glu Val Glu Glu Gly Gln Val Ile Gly Val His Thr Val Asp
                485                 490                 495 gag tgg aag ctg caa ctc cag aat gca aaa gac tcc aaa aaa ctg att      1536
Glu Trp Lys Leu Gln Leu Gln Asn Ala Lys Asp Ser Lys Lys Leu Ile
            500                 505                 510 gtg gtg gat ttt act gct tcc tgg tct ggt cca tgc cgt ttt atg gcc      1584
Val Val Asp Phe Thr Ala Ser Trp Ser Gly Pro Cys Arg Phe Met Ala
        515                 520                 525 cca gtt ctt gca gag att gca aag aaa act cct gaa ttg atc ttc ctc      1632
Pro Val Leu Ala Glu Ile Ala Lys Lys Thr Pro Glu Leu Ile Phe Leu
    530                 535                 540 aaa gtg gat gtg gat gaa gtg agg cct gtt gct gag gaa tat tcc att      1680
Lys Val Asp Val Asp Glu Val Arg Pro Val Ala Glu Glu Tyr Ser Ile
545                 550                 555                 560 gag gcc atg cca acc ttc ctc ttc ttg aaa gat ggc gag atc gtg gac      1728
Glu Ala Met Pro Thr Phe Leu Phe Leu Lys Asp Gly Glu Ile Val Asp
                565                 570                 575 aag gtg gtt ggt gct agt aag gat gac ctt caa gcc acc ata gcc aag      1776
Lys Val Val Gly Ala Ser Lys Asp Asp Leu Gln Ala Thr Ile Ala Lys
            580                 585                 590 cat gca tct gct gtt gct gct gct tct tct tct                          1809
His Ala Ser Ala Val Ala Ala Ala Ser Ser Ser
        595                 600

<210> SEQ ID NO 25
<211> LENGTH: 603
<212> TYPE: PRT
<213> ORGANISM: Glycine max

<400> SEQUENCE: 25

Met Gly Ser Arg Glu Gln Pro Gln Gln Asn Glu Cys Gln Ile Gln Lys
1               5                   10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
65                  70                  75                  80

Phe Gly Met Ile Tyr Pro Gly Cys Pro Ser Thr Phe Glu Glu Pro Gln
                85                  90                  95

Gln Pro Gln Gln Arg Gly Gln Ser Ser Arg Pro Gln Asp Arg His Gln
            100                 105                 110

Lys Ile Tyr Asn Phe Arg Glu Gly Asp Leu Ile Ala Val Pro Thr Gly
        115                 120                 125

Val Ala Trp Trp Met Tyr Asn Asn Glu Asp Thr Pro Val Val Ala Val
```

```
            130                 135                 140
Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
                165                 170                 175

Gln Gln Glu Gln Gly Gly His Gln Ser Gln Lys Gly Lys His Gln Gln
            180                 185                 190

Glu Glu Glu Asn Glu Gly Gly Ser Ile Leu Ser Gly Phe Thr Leu Glu
            195                 200                 205

Phe Leu Glu His Ala Phe Ser Val Asp Lys Gln Ile Ala Lys Asn Leu
210                 215                 220

Gln Gly Glu Asn Glu Gly Glu Asp Lys Gly Ala Ile Val Thr Val Lys
225                 230                 235                 240

Gly Gly Leu Ser Val Leu Lys Pro Pro Thr Asp Glu Gln Gln Gln Arg
                245                 250                 255

Pro Gln Glu Glu Glu Glu Glu Asp Glu Lys Pro Gln Cys Lys
            260                 265                 270

Gly Lys Asp Lys His Cys Gln Arg Pro Arg Gly Ser Gln Ser Lys Ser
            275                 280                 285

Arg Arg Asn Gly Ile Asp Glu Thr Ile Cys Thr Met Arg Leu Arg His
290                 295                 300

Asn Ile Gly Gln Thr Ser Ser Pro Asp Ile Tyr Asn Pro Gln Ala Gly
305                 310                 315                 320

Ser Val Thr Thr Ala Thr Ser Leu Asp Phe Pro Ala Leu Ser Trp Leu
                325                 330                 335

Arg Leu Ser Ala Glu Phe Gly Ser Leu Arg Lys Asn Ala Met Phe Val
            340                 345                 350

Pro His Tyr Asn Leu Asn Ala Asn Ser Ile Ile Tyr Ala Leu Asn Gly
            355                 360                 365

Arg Ala Leu Ile Gln Val Val Asn Cys Asn Gly Glu Arg Val Phe Asp
370                 375                 380

Gly Glu Leu Gln Glu Gly Arg Val Leu Ile Val Pro Gln Asn Phe Val
385                 390                 395                 400

Val Ala Ala Arg Ser Gln Ser Asp Asn Phe Glu Tyr Val Ser Phe Lys
                405                 410                 415

Thr Asn Asp Thr Pro Met Ile Gly Thr Leu Ala Gly Ala Asn Ser Leu
            420                 425                 430

Leu Asn Ala Leu Pro Glu Glu Val Ile Gln His Thr Phe Asn Leu Lys
            435                 440                 445

Ser Gln Gln Ala Arg Gln Ile Lys Asn Asn Asn Pro Phe Lys Phe Leu
450                 455                 460

Val Pro Pro Gln Glu Ser Gln Lys Arg Ala Val Ala Gly Gly Gly Ser
465                 470                 475                 480

Met Ala Glu Val Glu Glu Gly Gln Val Ile Gly Val His Thr Val Asp
                485                 490                 495

Glu Trp Lys Leu Gln Leu Gln Asn Ala Lys Asp Ser Lys Lys Leu Ile
            500                 505                 510

Val Val Asp Phe Thr Ala Ser Trp Ser Gly Pro Cys Arg Phe Met Ala
            515                 520                 525

Pro Val Leu Ala Glu Ile Ala Lys Lys Thr Pro Glu Leu Ile Phe Leu
530                 535                 540

Lys Val Asp Val Asp Glu Val Arg Pro Val Ala Glu Glu Tyr Ser Ile
545                 550                 555                 560
```

```
Glu Ala Met Pro Thr Phe Leu Phe Leu Lys Asp Gly Glu Ile Val Asp
                565                 570                 575

Lys Val Val Gly Ala Ser Lys Asp Asp Leu Gln Ala Thr Ile Ala Lys
            580                 585                 590

His Ala Ser Ala Val Ala Ala Ser Ser Ser
        595                 600

<210> SEQ ID NO 26
<211> LENGTH: 1860
<212> TYPE: DNA
<213> ORGANISM: Glycine max
<220> FEATURE:
<221> NAME/KEY: CDS
<222> LOCATION: (1)...(1860)

<400> SEQUENCE: 26
```

| | | | | | | | | | | | | | | | | |
|---|---|---|---|---|---|---|---|---|---|---|---|---|---|---|---|---|
| atg | ggt | tcc | aga | gag | cag | cct | cag | caa | aac | gag | tgc | cag | atc | caa | aaa | 48 |
| Met | Gly | Ser | Arg | Glu | Gln | Pro | Gln | Gln | Asn | Glu | Cys | Gln | Ile | Gln | Lys | |
| 1 | | | | 5 | | | | | 10 | | | | | 15 | | |
| ctc | aat | gcc | ctc | aaa | ccg | gat | aac | cgt | ata | gag | tca | gaa | gga | ggg | ctc | 96 |
| Leu | Asn | Ala | Leu | Lys | Pro | Asp | Asn | Arg | Ile | Glu | Ser | Glu | Gly | Gly | Leu | |
| | | | 20 | | | | | 25 | | | | | 30 | | | |
| att | gag | aca | tgg | aac | cct | aac | aac | aag | cca | ttc | cag | tgt | gcc | ggt | gtt | 144 |
| Ile | Glu | Thr | Trp | Asn | Pro | Asn | Asn | Lys | Pro | Phe | Gln | Cys | Ala | Gly | Val | |
| | | 35 | | | | | 40 | | | | | 45 | | | | |
| gcc | ctc | tct | cgc | tgc | acc | ctc | aac | cgc | aac | gcc | ctt | cgt | aga | cct | tcc | 192 |
| Ala | Leu | Ser | Arg | Cys | Thr | Leu | Asn | Arg | Asn | Ala | Leu | Arg | Arg | Pro | Ser | |
| | 50 | | | | | 55 | | | | | 60 | | | | | |
| tac | acc | aac | ggt | ccc | cag | gaa | atc | tac | atc | caa | caa | ggt | aag | ggt | att | 240 |
| Tyr | Thr | Asn | Gly | Pro | Gln | Glu | Ile | Tyr | Ile | Gln | Gln | Gly | Lys | Gly | Ile | |
| 65 | | | | | 70 | | | | | 75 | | | | | 80 | |
| ttt | ggc | atg | ata | tac | ccg | ggt | tgt | cct | agc | aca | ttt | gaa | gag | cct | cag | 288 |
| Phe | Gly | Met | Ile | Tyr | Pro | Gly | Cys | Pro | Ser | Thr | Phe | Glu | Glu | Pro | Gln | |
| | | | | 85 | | | | | 90 | | | | | 95 | | |
| caa | cct | caa | caa | aga | gga | caa | agc | agc | aga | cca | caa | gac | cgt | cac | cag | 336 |
| Gln | Pro | Gln | Gln | Arg | Gly | Gln | Ser | Ser | Arg | Pro | Gln | Asp | Arg | His | Gln | |
| | | | 100 | | | | | 105 | | | | | 110 | | | |
| aag | atc | tat | aac | ttc | aga | gag | ggt | gat | ttg | atc | gca | gtg | cct | act | ggt | 384 |
| Lys | Ile | Tyr | Asn | Phe | Arg | Glu | Gly | Asp | Leu | Ile | Ala | Val | Pro | Thr | Gly | |
| | | 115 | | | | | 120 | | | | | 125 | | | | |
| gtt | gca | tgg | tgg | atg | tac | aac | aat | gaa | gac | act | cct | gtt | gtt | gcc | gtt | 432 |
| Val | Ala | Trp | Trp | Met | Tyr | Asn | Asn | Glu | Asp | Thr | Pro | Val | Val | Ala | Val | |
| | 130 | | | | | 135 | | | | | 140 | | | | | |
| tct | att | att | gac | acc | aac | agc | ttg | gag | aac | cag | ctc | gac | cag | atg | cct | 480 |
| Ser | Ile | Ile | Asp | Thr | Asn | Ser | Leu | Glu | Asn | Gln | Leu | Asp | Gln | Met | Pro | |
| 145 | | | | | 150 | | | | | 155 | | | | | 160 | |
| agg | aga | ttc | tat | ctt | gct | ggg | aac | caa | gag | caa | gag | ttt | cta | aaa | tat | 528 |
| Arg | Arg | Phe | Tyr | Leu | Ala | Gly | Asn | Gln | Glu | Gln | Glu | Phe | Leu | Lys | Tyr | |
| | | | | 165 | | | | | 170 | | | | | 175 | | |
| cag | caa | gag | caa | gga | ggt | cat | caa | agc | cag | aaa | gga | aag | cat | cag | caa | 576 |
| Gln | Gln | Glu | Gln | Gly | Gly | His | Gln | Ser | Gln | Lys | Gly | Lys | His | Gln | Gln | |
| | | | 180 | | | | | 185 | | | | | 190 | | | |
| gaa | gaa | gaa | aac | gaa | gga | ggc | agc | ata | ttg | agt | ggc | ttc | acc | ctg | gaa | 624 |
| Glu | Glu | Glu | Asn | Glu | Gly | Gly | Ser | Ile | Leu | Ser | Gly | Phe | Thr | Leu | Glu | |
| | | 195 | | | | | 200 | | | | | 205 | | | | |
| ttc | ttg | gaa | cat | gca | ttc | agc | gtg | gac | aag | cag | ata | gcg | aaa | aac | cta | 672 |
| Phe | Leu | Glu | His | Ala | Phe | Ser | Val | Asp | Lys | Gln | Ile | Ala | Lys | Asn | Leu | |
| | 210 | | | | | 215 | | | | | 220 | | | | | |
| caa | gga | gag | aac | gaa | ggg | gaa | gac | aag | gga | gcc | att | gtg | aca | gtg | aaa | 720 |
| Gln | Gly | Glu | Asn | Glu | Gly | Glu | Asp | Lys | Gly | Ala | Ile | Val | Thr | Val | Lys | |

-continued

```
                   225                 230                 235                 240
gga ggt ctg agc gtg tta aaa cca ccc acg gac gag caa caa aga                   768
Gly Gly Leu Ser Val Leu Lys Pro Pro Thr Asp Glu Gln Gln Arg
                           245                 250                 255 ccc cag gaa gag gaa gaa gaa gag gat gag aag cca cag tgc aag                   816
Pro Gln Glu Glu Glu Glu Glu Glu Asp Glu Lys Pro Gln Cys Lys
                   260                 265                 270 ggt aaa gac aaa cac tgc caa cgc ccc cga gga agc caa agc aaa agc               864
Gly Lys Asp Lys His Cys Gln Arg Pro Arg Gly Ser Gln Ser Lys Ser
               275                 280                 285 aga aga aat ggc att gac gag acc ata tgc acc atg aga ctt cgc cac               912
Arg Arg Asn Gly Ile Asp Glu Thr Ile Cys Thr Met Arg Leu Arg His
           290                 295                 300 aac att ggc cag act tca tca cct gac atc tac aac cct caa gcc ggt               960
Asn Ile Gly Gln Thr Ser Ser Pro Asp Ile Tyr Asn Pro Gln Ala Gly
305                 310                 315                 320 agc gtc aca acc gcc acc agc ctt gac ttc cca gcc ctc tcg tgg ctc              1008
Ser Val Thr Thr Ala Thr Ser Leu Asp Phe Pro Ala Leu Ser Trp Leu
                   325                 330                 335 aga ctc agt gct gag ttt gga tct ctc cgc aag aat gca atg ttc gtg              1056
Arg Leu Ser Ala Glu Phe Gly Ser Leu Arg Lys Asn Ala Met Phe Val
               340                 345                 350 cca cac tac aac ctg aac gcg aac agc ata ata tac gca ttg aat gga              1104
Pro His Tyr Asn Leu Asn Ala Asn Ser Ile Ile Tyr Ala Leu Asn Gly
           355                 360                 365 cgg gca ttg ata caa gtg gtg aat tgc aac ggt gag aga gtg ttt gat              1152
Arg Ala Leu Ile Gln Val Val Asn Cys Asn Gly Glu Arg Val Phe Asp
370                 375                 380 gga gag ctg caa gag gga cgg gtg ctg atc gtg cca caa aac ttt gtg              1200
Gly Glu Leu Gln Glu Gly Arg Val Leu Ile Val Pro Gln Asn Phe Val
385                 390                 395                 400 gtg gct gca aga tca cag agt gac aac ttc gag tat gtg tca ttc aag              1248
Val Ala Ala Arg Ser Gln Ser Asp Asn Phe Glu Tyr Val Ser Phe Lys
                   405                 410                 415 acc aat gat aca ccc atg atc ggc act ctt gca ggg gca aac tca ttg              1296
Thr Asn Asp Thr Pro Met Ile Gly Thr Leu Ala Gly Ala Asn Ser Leu
               420                 425                 430 ttg aac gca tta cca gag gaa gtg att cag cac act ttc aac cta aaa              1344
Leu Asn Ala Leu Pro Glu Glu Val Ile Gln His Thr Phe Asn Leu Lys
           435                 440                 445 agc cag cag gcc agg cag ata aag aac aac aac cct ttc aag ttc ctg              1392
Ser Gln Gln Ala Arg Gln Ile Lys Asn Asn Asn Pro Phe Lys Phe Leu
450                 455                 460 gtt cca cct cag gag tct cag aag aga gct gtg gct ggt ggt gga tcc              1440
Val Pro Pro Gln Glu Ser Gln Lys Arg Ala Val Ala Gly Gly Gly Ser
465                 470                 475                 480 atg gca tcc cat agg caa agc tat gaa gct ggt caa act aag ggc cga              1488
Met Ala Ser His Arg Gln Ser Tyr Glu Ala Gly Gln Thr Lys Gly Arg
                   485                 490                 495 act gag gaa aag acg aac cag acg atg ggc aat att gga gag aag gct              1536
Thr Glu Glu Lys Thr Asn Gln Thr Met Gly Asn Ile Gly Glu Lys Ala
               500                 505                 510 caa gct gca aag gag aag acc cag gaa atg gcc caa gct gca aag gag              1584
Gln Ala Ala Lys Glu Lys Thr Gln Glu Met Ala Gln Ala Ala Lys Glu
           515                 520                 525 aag acc caa caa aca gcc caa gct gcc aag gac aag act tgc gac act              1632
Lys Thr Gln Gln Thr Ala Gln Ala Ala Lys Asp Lys Thr Cys Asp Thr
530                 535                 540 tcc caa gcg gca aag gag aag acc caa cag aat aca gga gct gct caa              1680
```

| | | | | | | | | | | | | |
|---|---|---|---|---|---|---|---|---|---|---|---|---|
| Ser | Gln | Ala | Ala | Lys | Glu | Lys | Thr | Gln | Gln | Asn | Thr | Gly | Ala | Ala | Gln |
| 545 | | | | 550 | | | | | 555 | | | | 560 |

```
caa aag acc tca gag atg ggc cag tcc acg aag gaa tcg gcc cag tca      1728
Gln Lys Thr Ser Glu Met Gly Gln Ser Thr Lys Glu Ser Ala Gln Ser
                565                 570                 575 ggg aag gac aac acc caa ggg ttc ctg cag cag aca ggg gag aag gtg      1776
Gly Lys Asp Asn Thr Gln Gly Phe Leu Gln Gln Thr Gly Glu Lys Val
            580                 585                 590 aag ggc gca gcc caa ggt gct aca gag gct gtg aag caa acc ctt ggc      1824
Lys Gly Ala Ala Gln Gly Ala Thr Glu Ala Val Lys Gln Thr Leu Gly
        595                 600                 605 ttg ggc gaa cat gat caa gac aac cgc aga aat tac                      1860
Leu Gly Glu His Asp Gln Asp Asn Arg Arg Asn Tyr
    610                 615                 620

<210> SEQ ID NO 27
<211> LENGTH: 620
<212> TYPE: PRT
<213> ORGANISM: Glycine max

<400> SEQUENCE: 27

Met Gly Ser Arg Glu Gln Pro Gln Gln Asn Glu Cys Gln Ile Gln Lys
 1               5                  10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
65                  70                  75                  80

Phe Gly Met Ile Tyr Pro Gly Cys Pro Ser Thr Phe Glu Glu Pro Gln
                85                  90                  95

Gln Pro Gln Gln Arg Gly Gln Ser Ser Arg Pro Gln Asp Arg His Gln
            100                 105                 110

Lys Ile Tyr Asn Phe Arg Glu Gly Asp Leu Ile Ala Val Pro Thr Gly
        115                 120                 125

Val Ala Trp Trp Met Tyr Asn Asn Glu Asp Thr Pro Val Val Ala Val
    130                 135                 140

Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
                165                 170                 175

Gln Gln Glu Gln Gly Gly His Gln Ser Gln Lys Gly Lys His Gln Gln
            180                 185                 190

Glu Glu Glu Asn Glu Gly Gly Ser Ile Leu Ser Gly Phe Thr Leu Glu
        195                 200                 205

Phe Leu Glu His Ala Phe Ser Val Asp Lys Gln Ile Ala Lys Asn Leu
    210                 215                 220

Gln Gly Glu Asn Glu Gly Glu Asp Lys Gly Ala Ile Val Thr Val Lys
225                 230                 235                 240

Gly Gly Leu Ser Val Leu Lys Pro Pro Thr Asp Glu Gln Gln Gln Arg
                245                 250                 255

Pro Gln Glu Glu Glu Glu Glu Glu Asp Glu Lys Pro Gln Cys Lys
            260                 265                 270

Gly Lys Asp Lys His Cys Gln Arg Pro Arg Gly Ser Gln Ser Lys Ser
```

```
                275                 280                 285
Arg Arg Asn Gly Ile Asp Glu Thr Ile Cys Thr Met Arg Leu Arg His
290                 295                 300

Asn Ile Gly Gln Thr Ser Ser Pro Asp Ile Tyr Asn Pro Gln Ala Gly
305                 310                 315                 320

Ser Val Thr Thr Ala Thr Ser Leu Asp Phe Pro Ala Leu Ser Trp Leu
                325                 330                 335

Arg Leu Ser Ala Glu Phe Gly Ser Leu Arg Lys Asn Ala Met Phe Val
                340                 345                 350

Pro His Tyr Asn Leu Asn Ala Asn Ser Ile Ile Tyr Ala Leu Asn Gly
                355                 360                 365

Arg Ala Leu Ile Gln Val Val Asn Cys Asn Gly Glu Arg Val Phe Asp
370                 375                 380

Gly Glu Leu Gln Glu Gly Arg Val Leu Ile Val Pro Gln Asn Phe Val
385                 390                 395                 400

Val Ala Ala Arg Ser Gln Ser Asp Asn Phe Glu Tyr Val Ser Phe Lys
                405                 410                 415

Thr Asn Asp Thr Pro Met Ile Gly Thr Leu Ala Gly Ala Asn Ser Leu
                420                 425                 430

Leu Asn Ala Leu Pro Glu Glu Val Ile Gln His Thr Phe Asn Leu Lys
                435                 440                 445

Ser Gln Gln Ala Arg Gln Ile Lys Asn Asn Asn Pro Phe Lys Phe Leu
                450                 455                 460

Val Pro Pro Gln Glu Ser Gln Lys Arg Ala Val Ala Gly Gly Gly Ser
465                 470                 475                 480

Met Ala Ser His Arg Gln Ser Tyr Glu Ala Gly Gln Thr Lys Gly Arg
                485                 490                 495

Thr Glu Glu Lys Thr Asn Gln Thr Met Gly Asn Ile Gly Glu Lys Ala
                500                 505                 510

Gln Ala Ala Lys Glu Lys Thr Gln Glu Met Ala Gln Ala Ala Lys Glu
                515                 520                 525

Lys Thr Gln Gln Thr Ala Gln Ala Ala Lys Asp Lys Thr Cys Asp Thr
530                 535                 540

Ser Gln Ala Ala Lys Glu Lys Thr Gln Asn Thr Gly Ala Ala Gln
545                 550                 555                 560

Gln Lys Thr Ser Glu Met Gly Gln Ser Thr Lys Ser Ala Gln Ser
                565                 570                 575

Gly Lys Asp Asn Thr Gln Gly Phe Leu Gln Gln Thr Gly Glu Lys Val
                580                 585                 590

Lys Gly Ala Ala Gln Gly Ala Thr Glu Ala Val Lys Gln Thr Leu Gly
                595                 600                 605

Leu Gly Glu His Asp Gln Asp Asn Arg Arg Asn Tyr
610                 615                 620

<210> SEQ ID NO 28
<211> LENGTH: 1641
<212> TYPE: DNA
<213> ORGANISM: Glycine max
<220> FEATURE:
<221> NAME/KEY: CDS
<222> LOCATION: (1)...(1641)

<400> SEQUENCE: 28 atg ggt tcc aga gag cag cct cag caa aac gag tgc cag atc caa aaa    48
Met Gly Ser Arg Glu Gln Pro Gln Gln Asn Glu Cys Gln Ile Gln Lys
1               5                   10                  15
```

-continued

```
ctc aat gcc ctc aaa ccg gat aac cgt ata gag tca gaa gga ggg ctc      96
Leu Asn Ala Leu Lys Pro Asp Asn Arg Ile Glu Ser Glu Gly Gly Leu
            20                  25                  30 att gag aca tgg aac cct aac aac aag cca ttc cag tgt gcc ggt gtt     144
Ile Glu Thr Trp Asn Pro Asn Asn Lys Pro Phe Gln Cys Ala Gly Val
        35                  40                  45 gcc ctc tct cgc tgc acc ctc aac cgc aac gcc ctt cgt aga cct tcc     192
Ala Leu Ser Arg Cys Thr Leu Asn Arg Asn Ala Leu Arg Arg Pro Ser
    50                  55                  60 tac acc aac ggt ccc cag gaa atc tac atc caa caa ggt aag ggt att     240
Tyr Thr Asn Gly Pro Gln Glu Ile Tyr Ile Gln Gln Gly Lys Gly Ile
65                  70                  75                  80 ttt ggc atg ata tac ccg ggt tgt cct agc aca ttt gaa gag cct cag     288
Phe Gly Met Ile Tyr Pro Gly Cys Pro Ser Thr Phe Glu Glu Pro Gln
                85                  90                  95 caa cct caa caa aga gga caa agc agc aga cca caa gac cgt cac cag     336
Gln Pro Gln Gln Arg Gly Gln Ser Ser Arg Pro Gln Asp Arg His Gln
            100                 105                 110 aag atc tat aac ttc aga gag ggt gat ttg atc gca gtg cct act ggt     384
Lys Ile Tyr Asn Phe Arg Glu Gly Asp Leu Ile Ala Val Pro Thr Gly
        115                 120                 125 gtt gca tgg tgg atg tac aac aat gaa gac act cct gtt gtt gcc gtt     432
Val Ala Trp Trp Met Tyr Asn Asn Glu Asp Thr Pro Val Val Ala Val
    130                 135                 140 tct att att gac acc aac agc ttg gag aac cag ctc gac cag atg cct     480
Ser Ile Ile Asp Thr Asn Ser Leu Glu Asn Gln Leu Asp Gln Met Pro
145                 150                 155                 160 agg aga ttc tat ctt gct ggg aac caa gag caa gag ttt cta aaa tat     528
Arg Arg Phe Tyr Leu Ala Gly Asn Gln Glu Gln Glu Phe Leu Lys Tyr
                165                 170                 175 cag caa gag caa gga ggt cat caa agc cag aaa gga aag cat cag caa     576
Gln Gln Glu Gln Gly Gly His Gln Ser Gln Lys Gly Lys His Gln Gln
            180                 185                 190 gaa gaa gaa aac gaa gga ggc agc ata ttg agt ggc ttc acc ctg gaa     624
Glu Glu Glu Asn Glu Gly Gly Ser Ile Leu Ser Gly Phe Thr Leu Glu
        195                 200                 205 ttc ttg gaa cat gca ttc agc gtg gac aag cag ata gcg aaa aac cta     672
Phe Leu Glu His Ala Phe Ser Val Asp Lys Gln Ile Ala Lys Asn Leu
    210                 215                 220 caa gga gag aac gaa ggg gaa gac aag gga gcc att gtg aca gtg aaa     720
Gln Gly Glu Asn Glu Gly Glu Asp Lys Gly Ala Ile Val Thr Val Lys
225                 230                 235                 240 gga ggt ctg agc gtg tta aaa cca ccc acg gac gag cag caa caa aga     768
Gly Gly Leu Ser Val Leu Lys Pro Pro Thr Asp Glu Gln Gln Gln Arg
                245                 250                 255 ccc cag gaa gag gaa gaa gaa gaa gag gat gag aag cca cag tgc aag     816
Pro Gln Glu Glu Glu Glu Glu Glu Asp Glu Lys Pro Gln Cys Lys
            260                 265                 270 ggt aaa gac aaa cac tgc caa cgc ccc cga gga agc caa agc aaa agc     864
Gly Lys Asp Lys His Cys Gln Arg Pro Arg Gly Ser Gln Ser Lys Ser
        275                 280                 285 aga aga aat ggc att gac gag acc ata tgc acc atg aga ctt cgc cac     912
Arg Arg Asn Gly Ile Asp Glu Thr Ile Cys Thr Met Arg Leu Arg His
    290                 295                 300 aac att ggc cag act tca tca cct gac atc tac aac cct caa gcc ggt     960
Asn Ile Gly Gln Thr Ser Ser Pro Asp Ile Tyr Asn Pro Gln Ala Gly
305                 310                 315                 320 agc gtc aca acc gcc acc agc ctt gac ttc cca gcc ctc tcg tgg ctc    1008
Ser Val Thr Thr Ala Thr Ser Leu Asp Phe Pro Ala Leu Ser Trp Leu
```

```
                    325                 330                 335
aga ctc agt gct gag ttt gga tct ctc cgc aag aat gca atg ttc gtg      1056
Arg Leu Ser Ala Glu Phe Gly Ser Leu Arg Lys Asn Ala Met Phe Val
            340                 345                 350 cca cac tac aac ctg aac gcg aac agc ata ata tac gca ttg aat gga      1104
Pro His Tyr Asn Leu Asn Ala Asn Ser Ile Ile Tyr Ala Leu Asn Gly
        355                 360                 365 cgg gca ttg ata caa gtg gtg aat tgc aac ggt gag aga gtg ttt gat      1152
Arg Ala Leu Ile Gln Val Val Asn Cys Asn Gly Glu Arg Val Phe Asp
    370                 375                 380 gga gag ctg caa gag gga cgg gtg ctg atc gtg cca caa aac ttt gtg      1200
Gly Glu Leu Gln Glu Gly Arg Val Leu Ile Val Pro Gln Asn Phe Val
385                 390                 395                 400 gtg gct gca aga tca cag agt gac aac ttc gag tat gtg tca ttc aag      1248
Val Ala Ala Arg Ser Gln Ser Asp Asn Phe Glu Tyr Val Ser Phe Lys
                405                 410                 415 acc aat gat aca ccc atg atc ggc act ctt gca ggg gca aac tca ttg      1296
Thr Asn Asp Thr Pro Met Ile Gly Thr Leu Ala Gly Ala Asn Ser Leu
            420                 425                 430 ttg aac gca tta cca gag gaa gtg att cag cac act ttc aac cta aaa      1344
Leu Asn Ala Leu Pro Glu Glu Val Ile Gln His Thr Phe Asn Leu Lys
        435                 440                 445 agc cag cag gcc agg cag ata aag aac aac aac cct ttc aag ttc ctg      1392
Ser Gln Gln Ala Arg Gln Ile Lys Asn Asn Asn Pro Phe Lys Phe Leu
    450                 455                 460 gtt cca cct cag gag tct cag aag aga gct gtg gct ggt ggt gga tcc      1440
Val Pro Pro Gln Glu Ser Gln Lys Arg Ala Val Ala Gly Gly Gly Ser
465                 470                 475                 480 atg gct aag att aag tgc acg tgg cct gag ctg gtg ggc aag acc gtg      1488
Met Ala Lys Ile Lys Cys Thr Trp Pro Glu Leu Val Gly Lys Thr Val
                485                 490                 495 gag aaa gcc aag aag atg atc atg aag gac aag cca gag gcg aag atc      1536
Glu Lys Ala Lys Lys Met Ile Met Lys Asp Lys Pro Glu Ala Lys Ile
            500                 505                 510 atg gtt ctg cca gtt ggg acc aaa gtg acc ggt gaa tgg aag atg gat      1584
Met Val Leu Pro Val Gly Thr Lys Val Thr Gly Glu Trp Lys Met Asp
        515                 520                 525 cgc gtc cgc ctc tgg gtc gac aag aag gac aag atc gcc aag act ccg      1632
Arg Val Arg Leu Trp Val Asp Lys Lys Asp Lys Ile Ala Lys Thr Pro
    530                 535                 540 aag tgc ggc                                                          1641
Lys Cys Gly
545

<210> SEQ ID NO 29
<211> LENGTH: 547
<212> TYPE: PRT
<213> ORGANISM: Glycine max

<400> SEQUENCE: 29

Met Gly Ser Arg Glu Gln Pro Gln Gln Asn Glu Cys Gln Ile Gln Lys
 1               5                  10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
```

-continued

```
             65                  70                  75                  80
         Phe Gly Met Ile Tyr Pro Gly Cys Pro Ser Thr Phe Glu Glu Pro Gln
                          85                  90                  95
         Gln Pro Gln Gln Arg Gly Gln Ser Ser Arg Pro Gln Asp Arg His Gln
                         100                 105                 110
         Lys Ile Tyr Asn Phe Arg Glu Gly Asp Leu Ile Ala Val Pro Thr Gly
                         115                 120                 125
         Val Ala Trp Trp Met Tyr Asn Asn Glu Asp Thr Pro Val Ala Val
                         130                 135                 140
         Ser Ile Ile Asp Thr Asn Ser Leu Glu Asn Gln Leu Asp Gln Met Pro
         145                 150                 155                 160
         Arg Arg Phe Tyr Leu Ala Gly Asn Gln Glu Gln Glu Phe Leu Lys Tyr
                         165                 170                 175
         Gln Gln Glu Gln Gly Gly His Gln Ser Gln Lys Gly Lys His Gln Gln
                         180                 185                 190
         Glu Glu Glu Asn Glu Gly Gly Ser Ile Leu Ser Gly Phe Thr Leu Glu
                         195                 200                 205
         Phe Leu Glu His Ala Phe Ser Val Asp Lys Gln Ile Ala Lys Asn Leu
         210                 215                 220
         Gln Gly Glu Asn Glu Gly Glu Asp Lys Gly Ala Ile Val Thr Val Lys
         225                 230                 235                 240
         Gly Gly Leu Ser Val Leu Lys Pro Pro Thr Asp Glu Gln Gln Gln Arg
                         245                 250                 255
         Pro Gln Glu Glu Glu Glu Glu Glu Asp Glu Lys Pro Gln Cys Lys
                         260                 265                 270
         Gly Lys Asp Lys His Cys Gln Arg Pro Arg Gly Ser Gln Ser Lys Ser
                         275                 280                 285
         Arg Arg Asn Gly Ile Asp Glu Thr Ile Cys Thr Met Arg Leu Arg His
                         290                 295                 300
         Asn Ile Gly Gln Thr Ser Ser Pro Asp Ile Tyr Asn Pro Gln Ala Gly
         305                 310                 315                 320
         Ser Val Thr Thr Ala Thr Ser Leu Asp Phe Pro Ala Leu Ser Trp Leu
                         325                 330                 335
         Arg Leu Ser Ala Glu Phe Gly Ser Leu Arg Lys Asn Ala Met Phe Val
                         340                 345                 350
         Pro His Tyr Asn Leu Asn Ala Asn Ser Ile Ile Tyr Ala Leu Asn Gly
                         355                 360                 365
         Arg Ala Leu Ile Gln Val Val Asn Cys Asn Gly Glu Arg Val Phe Asp
                         370                 375                 380
         Gly Glu Leu Gln Glu Gly Arg Val Leu Ile Val Pro Gln Asn Phe Val
         385                 390                 395                 400
         Val Ala Ala Arg Ser Gln Ser Asp Asn Phe Glu Tyr Val Ser Phe Lys
                         405                 410                 415
         Thr Asn Asp Thr Pro Met Ile Gly Thr Leu Ala Gly Ala Asn Ser Leu
                         420                 425                 430
         Leu Asn Ala Leu Pro Glu Glu Val Ile Gln His Thr Phe Asn Leu Lys
                         435                 440                 445
         Ser Gln Gln Ala Arg Gln Ile Lys Asn Asn Pro Phe Lys Phe Leu
                         450                 455                 460
         Val Pro Pro Gln Glu Ser Gln Lys Arg Ala Val Ala Gly Gly Ser
         465                 470                 475                 480
         Met Ala Lys Ile Lys Cys Thr Trp Pro Glu Leu Val Gly Lys Thr Val
                         485                 490                 495
```

```
Glu Lys Ala Lys Lys Met Ile Met Lys Asp Lys Pro Glu Ala Lys Ile
                500                 505                 510
Met Val Leu Pro Val Gly Thr Lys Val Thr Gly Glu Trp Lys Met Asp
            515                 520                 525
Arg Val Arg Leu Trp Val Asp Lys Lys Asp Lys Ile Ala Lys Thr Pro
        530                 535                 540
Lys Cys Gly
545

<210> SEQ ID NO 30
<211> LENGTH: 1641
<212> TYPE: DNA
<213> ORGANISM: Glycine max
<220> FEATURE:
<221> NAME/KEY: CDS
<222> LOCATION: (1)...(1641)

<400> SEQUENCE: 30 atg ggt tcc aga gag cag cct cag caa aac gag tgc cag atc caa aaa      48
Met Gly Ser Arg Glu Gln Pro Gln Gln Asn Glu Cys Gln Ile Gln Lys
 1               5                  10                  15 ctc aat gcc ctc aaa ccg gat aac cgt ata gag tca gaa gga ggg ctc      96
Leu Asn Ala Leu Lys Pro Asp Asn Arg Ile Glu Ser Glu Gly Gly Leu
                20                  25                  30 att gag aca tgg aac cct aac aac aag cca ttc cag tgt gcc ggt gtt     144
Ile Glu Thr Trp Asn Pro Asn Asn Lys Pro Phe Gln Cys Ala Gly Val
             35                  40                  45 gcc ctc tct cgc tgc acc ctc aac cgc aac gcc ctt cgt aga cct tcc     192
Ala Leu Ser Arg Cys Thr Leu Asn Arg Asn Ala Leu Arg Arg Pro Ser
         50                  55                  60 tac acc aac ggt ccc cag gaa atc tac atc caa caa ggt aag ggt att     240
Tyr Thr Asn Gly Pro Gln Glu Ile Tyr Ile Gln Gln Gly Lys Gly Ile
 65                  70                  75                  80 ttt ggc atg ata tac ccg ggt tgt cct agc aca ttt gaa gag cct cag     288
Phe Gly Met Ile Tyr Pro Gly Cys Pro Ser Thr Phe Glu Glu Pro Gln
                 85                  90                  95 caa cct caa caa aga gga caa agc agc aga cca caa gac cgt cac cag     336
Gln Pro Gln Gln Arg Gly Gln Ser Ser Arg Pro Gln Asp Arg His Gln
            100                 105                 110 aag atc tat aac ttc aga gag ggt gat ttg atc gca gtg cct act ggt     384
Lys Ile Tyr Asn Phe Arg Glu Gly Asp Leu Ile Ala Val Pro Thr Gly
        115                 120                 125 gtt gca tgg tgg atg tac aac aat gaa gac act cct gtt gtt gcc gtt     432
Val Ala Trp Trp Met Tyr Asn Asn Glu Asp Thr Pro Val Val Ala Val
    130                 135                 140 tct att att gac acc aac agc ttg gag aac cag ctc gac cag atg cct     480
Ser Ile Ile Asp Thr Asn Ser Leu Glu Asn Gln Leu Asp Gln Met Pro
145                 150                 155                 160 agg aga ttc tat ctt gct ggg aac caa gag caa gag ttt cta aaa tat     528
Arg Arg Phe Tyr Leu Ala Gly Asn Gln Glu Gln Glu Phe Leu Lys Tyr
                165                 170                 175 cag caa gag caa gga ggt cat caa agc cag aaa gga aag cat cag caa     576
Gln Gln Glu Gln Gly Gly His Gln Ser Gln Lys Gly Lys His Gln Gln
            180                 185                 190 gaa gaa gaa aac gaa gga ggc agc ata ttg agt ggc ttc acc ctg gaa     624
Glu Glu Glu Asn Glu Gly Gly Ser Ile Leu Ser Gly Phe Thr Leu Glu
        195                 200                 205 ttc ttg gaa cat gca ttc agc gtg gac aag cag ata gcg aaa aac cta     672
Phe Leu Glu His Ala Phe Ser Val Asp Lys Gln Ile Ala Lys Asn Leu
    210                 215                 220
```

-continued

| | |
|---|---|
| caa gga gag aac gaa ggg gaa gac aag gga gcc att gtg aca gtg aaa<br>Gln Gly Glu Asn Glu Gly Glu Asp Lys Gly Ala Ile Val Thr Val Lys<br>225                            230                          235                          240 | 720 |
| gga ggt ctg agc gtg tta aaa cca ccc acg gac gag cag caa caa aga<br>Gly Gly Leu Ser Val Leu Lys Pro Pro Thr Asp Glu Gln Gln Gln Arg<br>                          245                          250                          255 | 768 |
| ccc cag gaa gag gaa gaa gaa gaa gag gat gag aag cca cag tgc aag<br>Pro Gln Glu Glu Glu Glu Glu Glu Asp Glu Lys Pro Gln Cys Lys<br>        260                          265                          270 | 816 |
| ggt aaa gac aaa cac tgc caa cgc ccc cga gga agc caa agc aaa agc<br>Gly Lys Asp Lys His Cys Gln Arg Pro Arg Gly Ser Gln Ser Lys Ser<br>            275                          280                          285 | 864 |
| aga aga aat ggc att gac gag acc ata tgc acc atg aga ctt cgc cac<br>Arg Arg Asn Gly Ile Asp Glu Thr Ile Cys Thr Met Arg Leu Arg His<br>290                            295                          300 | 912 |
| aac att ggc cag act tca tca cct gac atc tac aac cct caa gcc ggt<br>Asn Ile Gly Gln Thr Ser Ser Pro Asp Ile Tyr Asn Pro Gln Ala Gly<br>305                            310                          315                          320 | 960 |
| agc gtc aca acc gcc acc agc ctt gac ttc cca gcc ctc tcg tgg ctc<br>Ser Val Thr Thr Ala Thr Ser Leu Asp Phe Pro Ala Leu Ser Trp Leu<br>                          325                          330                          335 | 1008 |
| aga ctc agt gct gag ttt gga tct ctc cgc aag aat gca atg ttc gtg<br>Arg Leu Ser Ala Glu Phe Gly Ser Leu Arg Lys Asn Ala Met Phe Val<br>                340                          345                          350 | 1056 |
| cca cac tac aac ctg aac gcg aac agc ata ata tac gca ttg aat gga<br>Pro His Tyr Asn Leu Asn Ala Asn Ser Ile Ile Tyr Ala Leu Asn Gly<br>            355                          360                          365 | 1104 |
| cgg gca ttg ata caa gtg gtg aat tgc aac ggt gag aga gtg ttt gat<br>Arg Ala Leu Ile Gln Val Val Asn Cys Asn Gly Glu Arg Val Phe Asp<br>370                            375                          380 | 1152 |
| gga gag ctg caa gag gga cgg gtg ctg atc gtg cca caa aac ttt gtg<br>Gly Glu Leu Gln Glu Gly Arg Val Leu Ile Val Pro Gln Asn Phe Val<br>385                            390                          395                          400 | 1200 |
| gtg gct gca aga tca cag agt gac aac ttc gag tat gtg tca ttc aag<br>Val Ala Ala Arg Ser Gln Ser Asp Asn Phe Glu Tyr Val Ser Phe Lys<br>                          405                          410                          415 | 1248 |
| acc aat gat aca ccc atg atc ggc act ctt gca ggg gca aac tca ttg<br>Thr Asn Asp Thr Pro Met Ile Gly Thr Leu Ala Gly Ala Asn Ser Leu<br>            420                          425                          430 | 1296 |
| ttg aac gca tta cca gag gaa gtg att cag cac act ttc aac cta aaa<br>Leu Asn Ala Leu Pro Glu Glu Val Ile Gln His Thr Phe Asn Leu Lys<br>435                            440                          445 | 1344 |
| agc cag cag gcc agg cag ata aag aac aac aac cct ttc aag ttc ctg<br>Ser Gln Gln Ala Arg Gln Ile Lys Asn Asn Asn Pro Phe Lys Phe Leu<br>450                            455                          460 | 1392 |
| gtt cca cct cag gag tct cag aag aga gct gtg gct ggt ggt gga tcc<br>Val Pro Pro Gln Glu Ser Gln Lys Arg Ala Val Ala Gly Gly Gly Ser<br>465                            470                          475                          480 | 1440 |
| atg gcc acc acc aag tgc acc tgg cct gag ctc gtc ggc aag acc gtg<br>Met Ala Thr Thr Lys Cys Thr Trp Pro Glu Leu Val Gly Lys Thr Val<br>                          485                          490                          495 | 1488 |
| gag tgg gcc aag aag atc atc atg aag gac aag ccg acc gcc acc atc<br>Glu Trp Ala Lys Lys Ile Ile Met Lys Asp Lys Pro Thr Ala Thr Ile<br>            500                          505                          510 | 1536 |
| atc gtg atc cca gtg ggc acc atc gtg acc ggc gag tgg aag atc gac<br>Ile Val Ile Pro Val Gly Thr Ile Val Thr Gly Glu Trp Lys Ile Asp<br>                515                          520                          525 | 1584 |
| cgc gtc cgc ctg tgg gtc gac aag acc gac acc atc gcc aag acc ccg<br>Arg Val Arg Leu Trp Val Asp Lys Thr Asp Thr Ile Ala Lys Thr Pro | 1632 |

-continued

```
                       530                 535                 540
aag tgc ggc                                                                 1641
Lys Cys Gly
545
```

<210> SEQ ID NO 31
<211> LENGTH: 547
<212> TYPE: PRT
<213> ORGANISM: Glycine max

<400> SEQUENCE: 31

```
Met Gly Ser Arg Glu Gln Pro Gln Gln Asn Glu Cys Gln Ile Gln Lys
 1               5                  10                  15

Leu Asn Ala Leu Lys Pro Asp Asn Arg Ile Glu Ser Glu Gly Gly Leu
            20                  25                  30

Ile Glu Thr Trp Asn Pro Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
65                  70                  75                  80

Phe Gly Met Ile Tyr Pro Gly Cys Pro Ser Thr Phe Glu Glu Pro Gln
                85                  90                  95

Gln Pro Gln Gln Arg Gly Gln Ser Ser Arg Pro Gln Asp Arg His Gln
           100                 105                 110

Lys Ile Tyr Asn Phe Arg Glu Gly Asp Leu Ile Ala Val Pro Thr Gly
       115                 120                 125

Val Ala Trp Trp Met Tyr Asn Asn Glu Asp Thr Pro Val Val Ala Val
130                 135                 140

Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
                165                 170                 175

Gln Gln Glu Gln Gly Gly His Gln Ser Gln Lys Gly Lys His Gln Gln
            180                 185                 190

Glu Glu Glu Asn Glu Gly Gly Ser Ile Leu Ser Gly Phe Thr Leu Glu
        195                 200                 205

Phe Leu Glu His Ala Phe Ser Val Asp Lys Gln Ile Ala Lys Asn Leu
    210                 215                 220

Gln Gly Glu Asn Glu Gly Glu Asp Lys Gly Ala Ile Val Thr Val Lys
225                 230                 235                 240

Gly Gly Leu Ser Val Leu Lys Pro Pro Thr Asp Glu Gln Gln Gln Arg
                245                 250                 255

Pro Gln Glu Glu Glu Glu Glu Glu Asp Glu Lys Pro Gln Cys Lys
            260                 265                 270

Gly Lys Asp Lys His Cys Gln Arg Pro Arg Gly Ser Gln Ser Lys Ser
        275                 280                 285

Arg Arg Asn Gly Ile Asp Glu Thr Ile Cys Thr Met Arg Leu Arg His
    290                 295                 300

Asn Ile Gly Gln Thr Ser Ser Pro Asp Ile Tyr Asn Pro Gln Ala Gly
305                 310                 315                 320

Ser Val Thr Thr Ala Thr Ser Leu Asp Phe Pro Ala Leu Ser Trp Leu
                325                 330                 335

Arg Leu Ser Ala Glu Phe Gly Ser Leu Arg Lys Asn Ala Met Phe Val
            340                 345                 350
```

```
Pro His Tyr Asn Leu Asn Ala Asn Ser Ile Ile Tyr Ala Leu Asn Gly
            355                 360                 365

Arg Ala Leu Ile Gln Val Val Asn Cys Asn Gly Glu Arg Val Phe Asp
        370                 375                 380

Gly Glu Leu Gln Glu Gly Arg Val Leu Ile Val Pro Gln Asn Phe Val
385                 390                 395                 400

Val Ala Ala Arg Ser Gln Ser Asp Asn Phe Glu Tyr Val Ser Phe Lys
                405                 410                 415

Thr Asn Asp Thr Pro Met Ile Gly Thr Leu Ala Gly Ala Asn Ser Leu
            420                 425                 430

Leu Asn Ala Leu Pro Glu Glu Val Ile Gln His Thr Phe Asn Leu Lys
        435                 440                 445

Ser Gln Gln Ala Arg Gln Ile Lys Asn Asn Asn Pro Phe Lys Phe Leu
    450                 455                 460

Val Pro Pro Gln Glu Ser Gln Lys Arg Ala Val Ala Gly Gly Gly Ser
465                 470                 475                 480

Met Ala Thr Thr Lys Cys Thr Trp Pro Glu Leu Val Gly Lys Thr Val
                485                 490                 495

Glu Trp Ala Lys Lys Ile Ile Met Lys Asp Lys Pro Thr Ala Thr Ile
            500                 505                 510

Ile Val Ile Pro Val Gly Thr Ile Val Thr Gly Glu Trp Lys Ile Asp
        515                 520                 525

Arg Val Arg Leu Trp Val Asp Lys Thr Asp Thr Ile Ala Lys Thr Pro
    530                 535                 540

Lys Cys Gly
545

<210> SEQ ID NO 32
<211> LENGTH: 2862
<212> TYPE: DNA
<213> ORGANISM: Glycine max
<220> FEATURE:
<221> NAME/KEY: CDS
<222> LOCATION: (1)...(2862)

<400> SEQUENCE: 32 atg ggt tcc aga gag cag cct cag caa aac gag tgc cag atc caa aaa       48
Met Gly Ser Arg Glu Gln Pro Gln Gln Asn Glu Cys Gln Ile Gln Lys
1               5                   10                  15 ctc aat gcc ctc aaa ccg gat aac cgt ata gag tca gaa gga ggg ctc       96
Leu Asn Ala Leu Lys Pro Asp Asn Arg Ile Glu Ser Glu Gly Gly Leu
            20                  25                  30 att gag aca tgg aac cct aac aac aag cca ttc cag tgt gcc ggt gtt      144
Ile Glu Thr Trp Asn Pro Asn Asn Lys Pro Phe Gln Cys Ala Gly Val
        35                  40                  45 gcc ctc tct cgc tgc acc ctc aac cgc aac gcc ctt cgt aga cct tcc      192
Ala Leu Ser Arg Cys Thr Leu Asn Arg Asn Ala Leu Arg Arg Pro Ser
    50                  55                  60 tac acc aac ggt ccc cag gaa atc tac atc caa caa ggt aag ggt att      240
Tyr Thr Asn Gly Pro Gln Glu Ile Tyr Ile Gln Gln Gly Lys Gly Ile
65                  70                  75                  80 ttt ggc atg ata tac ccg ggt tgt cct agc aca ttt gaa gag cct cag      288
Phe Gly Met Ile Tyr Pro Gly Cys Pro Ser Thr Phe Glu Glu Pro Gln
                85                  90                  95 caa cct caa caa aga gga caa agc agc aga cca caa gac cgt cac cag      336
Gln Pro Gln Gln Arg Gly Gln Ser Ser Arg Pro Gln Asp Arg His Gln
            100                 105                 110
```

-continued

```
aag atc tat aac ttc aga gag ggt gat ttg atc gca gtg cct act ggt        384
Lys Ile Tyr Asn Phe Arg Glu Gly Asp Leu Ile Ala Val Pro Thr Gly
        115                 120                 125 gtt gca tgg tgg atg tac aat aat gaa gac act cct gtt gtt gcc gtt        432
Val Ala Trp Trp Met Tyr Asn Asn Glu Asp Thr Pro Val Val Ala Val
130                 135                 140 tct att att gac acc aac agc ttg gag aac cag ctc gac cag atg cct        480
Ser Ile Ile Asp Thr Asn Ser Leu Glu Asn Gln Leu Asp Gln Met Pro
145                 150                 155                 160 agg aga ttc tat ctt gct ggg aac caa gag caa gag ttt cta aaa tat        528
Arg Arg Phe Tyr Leu Ala Gly Asn Gln Glu Gln Glu Phe Leu Lys Tyr
        165                 170                 175 cag caa gag caa gga ggt cat caa agc cag aaa gga aag cat cag caa        576
Gln Gln Glu Gln Gly Gly His Gln Ser Gln Lys Gly Lys His Gln Gln
        180                 185                 190 gaa gaa gaa aac gaa gga ggc agc ata ttg agt ggc ttc acc ctg gaa        624
Glu Glu Glu Asn Glu Gly Gly Ser Ile Leu Ser Gly Phe Thr Leu Glu
        195                 200                 205 ttc ttg gaa cat gca ttc agc gtg gac aag cag ata gcg aaa aac cta        672
Phe Leu Glu His Ala Phe Ser Val Asp Lys Gln Ile Ala Lys Asn Leu
210                 215                 220 caa gga gag aac gaa ggg gaa gac aag gga gcc att gtg aca gtg aaa        720
Gln Gly Glu Asn Glu Gly Glu Asp Lys Gly Ala Ile Val Thr Val Lys
225                 230                 235                 240 gga ggt ctg agc gtg tta aaa cca ccc acg gac gag cag caa caa aga        768
Gly Gly Leu Ser Val Leu Lys Pro Pro Thr Asp Glu Gln Gln Gln Arg
            245                 250                 255 ccc cag gaa gag gaa gaa gaa gag gat gag aag cca cag tgc aag        816
Pro Gln Glu Glu Glu Glu Glu Glu Asp Glu Lys Pro Gln Cys Lys
            260                 265                 270 ggt aaa gac aaa cac tgc caa cgc ccc cga gga agc caa agc aaa agc        864
Gly Lys Asp Lys His Cys Gln Arg Pro Arg Gly Ser Gln Ser Lys Ser
        275                 280                 285 aga aga aat ggc att gac gag acc ata tgc acc atg aga ctt cgc cac        912
Arg Arg Asn Gly Ile Asp Glu Thr Ile Cys Thr Met Arg Leu Arg His
        290                 295                 300 aac att ggc cag act tca tca cct gac atc tac aac cct caa gcc ggt        960
Asn Ile Gly Gln Thr Ser Ser Pro Asp Ile Tyr Asn Pro Gln Ala Gly
305                 310                 315                 320 agc gtc aca acc gcc acc agc ctt gac ttc cca gcc ctc tcg tgg ctc       1008
Ser Val Thr Thr Ala Thr Ser Leu Asp Phe Pro Ala Leu Ser Trp Leu
            325                 330                 335 aga ctc agt gct gag ttt gga tct ctc cgc aag aat gca atg ttc gtg       1056
Arg Leu Ser Ala Glu Phe Gly Ser Leu Arg Lys Asn Ala Met Phe Val
            340                 345                 350 cca cac tac aac ctg aac gcg aac agc ata ata tac gca ttg aat gga       1104
Pro His Tyr Asn Leu Asn Ala Asn Ser Ile Ile Tyr Ala Leu Asn Gly
        355                 360                 365 cgg gca ttg ata caa gtg gtg aat tgc aac ggt gag aga gtg ttt gat       1152
Arg Ala Leu Ile Gln Val Val Asn Cys Asn Gly Glu Arg Val Phe Asp
        370                 375                 380 gga gag ctg caa gag gga cgg gtg ctg atc gtg cca caa aac ttt gtg       1200
Gly Glu Leu Gln Glu Gly Arg Val Leu Ile Val Pro Gln Asn Phe Val
385                 390                 395                 400 gtg gct gca aga tca cag agt gac aac ttc gag tat gtg tca ttc aag       1248
Val Ala Ala Arg Ser Gln Ser Asp Asn Phe Glu Tyr Val Ser Phe Lys
            405                 410                 415 acc aat gat aca ccc atg atc ggc act ctt gca ggg gca aac tca ttg       1296
Thr Asn Asp Thr Pro Met Ile Gly Thr Leu Ala Gly Ala Asn Ser Leu
            420                 425                 430
```

-continued

| | |
|---|---|
| ttg aac gca tta cca gag gaa gtg att cag cac act ttc aac cta aaa<br>Leu Asn Ala Leu Pro Glu Glu Val Ile Gln His Thr Phe Asn Leu Lys<br>435                          440                      445 | 1344 |
| agc cag cag gcc agg cag ata aag aac aac aac cct ttc aag ttc ctg<br>Ser Gln Gln Ala Arg Gln Ile Lys Asn Asn Asn Pro Phe Lys Phe Leu<br>     450                     455                     460 | 1392 |
| gtt cca cct cag gag tct cag aag aga gct gtg gct ggt ggt gga tcc<br>Val Pro Pro Gln Glu Ser Gln Lys Arg Ala Val Ala Gly Gly Gly Ser<br>465                          470                     475                 480 | 1440 |
| tcc aga gag cag cct cag caa aac gag tgc cag atc caa aaa ctc aat<br>Ser Arg Glu Gln Pro Gln Gln Asn Glu Cys Gln Ile Gln Lys Leu Asn<br>                     485                     490                     495 | 1488 |
| gcc ctc aaa ccg gat aac cgt ata gag tca gaa gga ggg ctc att gag<br>Ala Leu Lys Pro Asp Asn Arg Ile Glu Ser Glu Gly Gly Leu Ile Glu<br>500                          505                     510 | 1536 |
| aca tgg aac cct aac aac aag cca ttc cag tgt gcc ggt gtt gcc ctc<br>Thr Trp Asn Pro Asn Asn Lys Pro Phe Gln Cys Ala Gly Val Ala Leu<br>     515                     520                     525 | 1584 |
| tct cgc tgc acc ctc aac cgc aac gcc ctt cgt aga cct tcc tac acc<br>Ser Arg Cys Thr Leu Asn Arg Asn Ala Leu Arg Arg Pro Ser Tyr Thr<br>530                          535                     540 | 1632 |
| aac ggt ccc cag gaa atc tac atc caa caa ggt aag ggt att ttt ggc<br>Asn Gly Pro Gln Glu Ile Tyr Ile Gln Gln Gly Lys Gly Ile Phe Gly<br>545                          550                     555                 560 | 1680 |
| atg ata tac ccg ggt tgt cct agc aca ttt gaa gag cct cag caa cct<br>Met Ile Tyr Pro Gly Cys Pro Ser Thr Phe Glu Glu Pro Gln Gln Pro<br>                     565                     570                     575 | 1728 |
| caa caa aga gga caa agc agc aga cca caa gac cgt cac cag aag atc<br>Gln Gln Arg Gly Gln Ser Ser Arg Pro Gln Asp Arg His Gln Lys Ile<br>                         580                     585                     590 | 1776 |
| tat aac ttc aga gag ggt gat ttg atc gca gtg cct act ggt gtt gca<br>Tyr Asn Phe Arg Glu Gly Asp Leu Ile Ala Val Pro Thr Gly Val Ala<br>     595                     600                     605 | 1824 |
| tgg tgg atg tac aac aat gaa gac act cct gtt gtt gcc gtt tct att<br>Trp Trp Met Tyr Asn Asn Glu Asp Thr Pro Val Val Ala Val Ser Ile<br>610                          615                     620 | 1872 |
| att gac acc aac agc ttg gag aac cag ctc gac cag atg cct agg aga<br>Ile Asp Thr Asn Ser Leu Glu Asn Gln Leu Asp Gln Met Pro Arg Arg<br>625                          630                     635                 640 | 1920 |
| ttc tat ctt gct ggg aac caa gag caa gag ttt cta aaa tat cag caa<br>Phe Tyr Leu Ala Gly Asn Gln Glu Gln Glu Phe Leu Lys Tyr Gln Gln<br>                     645                     650                     655 | 1968 |
| gag caa gga ggt cat caa agc cag aaa gga aag cat cag caa gaa gaa<br>Glu Gln Gly Gly His Gln Ser Gln Lys Gly Lys His Gln Gln Glu Glu<br>                     660                     665                     670 | 2016 |
| gaa aac gaa gga ggc agc ata ttg agt ggc ttc acc ctg gaa ttc ttg<br>Glu Asn Glu Gly Gly Ser Ile Leu Ser Gly Phe Thr Leu Glu Phe Leu<br>     675                     680                     685 | 2064 |
| gaa cat gca ttc agc gtg gac aag cag ata gcg aaa aac cta caa gga<br>Glu His Ala Phe Ser Val Asp Lys Gln Ile Ala Lys Asn Leu Gln Gly<br>690                          695                     700 | 2112 |
| gag aac gaa ggg gaa gac aag gga gcc att gtg aca gtg aaa gga ggt<br>Glu Asn Glu Gly Glu Asp Lys Gly Ala Ile Val Thr Val Lys Gly Gly<br>705                          710                     715                 720 | 2160 |
| ctg agc gtg tta aaa cca ccc acg gac gag cag caa caa aga ccc cag<br>Leu Ser Val Leu Lys Pro Pro Thr Asp Glu Gln Gln Gln Arg Pro Gln<br>                     725                     730                     735 | 2208 |
| gaa gag gaa gaa gaa gaa gag gat gag aag cca cag tgc aag ggt aaa<br>Glu Glu Glu Glu Glu Glu Glu Asp Glu Lys Pro Gln Cys Lys Gly Lys | 2256 |

```
                    740                 745                 750
gac aaa cac tgc caa cgc ccc cga gga agc caa agc aaa agc aga aga              2304
Asp Lys His Cys Gln Arg Pro Arg Gly Ser Gln Ser Lys Ser Arg Arg
        755                 760                 765 aat ggc att gac gag acc ata tgc acc atg aga ctt cgc cac aac att              2352
Asn Gly Ile Asp Glu Thr Ile Cys Thr Met Arg Leu Arg His Asn Ile
770                 775                 780 ggc cag act tca tca cct gac atc tac aac cct caa gcc ggt agc gtc              2400
Gly Gln Thr Ser Ser Pro Asp Ile Tyr Asn Pro Gln Ala Gly Ser Val
785                 790                 795                 800 aca acc gcc acc agc ctt gac ttc cca gcc ctc tcg tgg ctc aga ctc              2448
Thr Thr Ala Thr Ser Leu Asp Phe Pro Ala Leu Ser Trp Leu Arg Leu
                805                 810                 815 agt gct gag ttt gga tct ctc cgc aag aat gca atg ttc gtg cca cac              2496
Ser Ala Glu Phe Gly Ser Leu Arg Lys Asn Ala Met Phe Val Pro His
            820                 825                 830 tac aac ctg aac gcg aac agc ata ata tac gca ttg aat gga cgg gca              2544
Tyr Asn Leu Asn Ala Asn Ser Ile Ile Tyr Ala Leu Asn Gly Arg Ala
        835                 840                 845 ttg ata caa gtg gtg aat tgc aac ggt gag aga gtg ttt gat gga gag              2592
Leu Ile Gln Val Val Asn Cys Asn Gly Glu Arg Val Phe Asp Gly Glu
850                 855                 860 ctg caa gag gga cgg gtg ctg atc gtg cca caa aac ttt gtg gtg gct              2640
Leu Gln Glu Gly Arg Val Leu Ile Val Pro Gln Asn Phe Val Val Ala
865                 870                 875                 880 gca aga tca cag agt gac aac ttc gag tat gtg tca ttc aag acc aat              2688
Ala Arg Ser Gln Ser Asp Asn Phe Glu Tyr Val Ser Phe Lys Thr Asn
                885                 890                 895 gat aca ccc atg atc ggc act ctt gca ggg gca aac tca ttg ttg aac              2736
Asp Thr Pro Met Ile Gly Thr Leu Ala Gly Ala Asn Ser Leu Leu Asn
            900                 905                 910 gca tta cca gag gaa gtg att cag cac act ttc aac cta aaa agc cag              2784
Ala Leu Pro Glu Glu Val Ile Gln His Thr Phe Asn Leu Lys Ser Gln
        915                 920                 925 cag gcc agg cag ata aag aac aac aac cct ttc aag ttc ctg gtt cca              2832
Gln Ala Arg Gln Ile Lys Asn Asn Asn Pro Phe Lys Phe Leu Val Pro
930                 935                 940 cct cag gag tct cag aag aga gct gtg gct                                      2862
Pro Gln Glu Ser Gln Lys Arg Ala Val Ala
945                 950

<210> SEQ ID NO 33
<211> LENGTH: 954
<212> TYPE: PRT
<213> ORGANISM: Glycine max

<400> SEQUENCE: 33

Met Gly Ser Arg Glu Gln Pro Gln Gln Asn Glu Cys Gln Ile Gln Lys
1               5                   10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
65                  70                  75                  80

Phe Gly Met Ile Tyr Pro Gly Cys Pro Ser Thr Phe Glu Glu Pro Gln
                85                  90                  95
```

```
Gln Pro Gln Gln Arg Gly Gln Ser Ser Arg Pro Gln Asp Arg His Gln
            100                 105                 110

Lys Ile Tyr Asn Phe Arg Glu Gly Asp Leu Ile Ala Val Pro Thr Gly
            115                 120                 125

Val Ala Trp Trp Met Tyr Asn Asn Glu Asp Thr Pro Val Val Ala Val
            130                 135                 140

Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
            165                 170                 175

Gln Gln Glu Gln Gly Gly His Gln Ser Gln Lys Gly Lys His Gln Gln
            180                 185                 190

Glu Glu Glu Asn Glu Gly Gly Ser Ile Leu Ser Gly Phe Thr Leu Glu
            195                 200                 205

Phe Leu Glu His Ala Phe Ser Val Asp Lys Gln Ile Ala Lys Asn Leu
            210                 215                 220

Gln Gly Glu Asn Glu Gly Glu Asp Lys Gly Ala Ile Val Thr Val Lys
225                 230                 235                 240

Gly Gly Leu Ser Val Leu Lys Pro Pro Thr Asp Gln Gln Gln Gln Arg
            245                 250                 255

Pro Gln Glu Glu Glu Glu Glu Glu Asp Glu Lys Pro Gln Cys Lys
            260                 265                 270

Gly Lys Asp Lys His Cys Gln Arg Pro Arg Gly Ser Gln Ser Lys Ser
            275                 280                 285

Arg Arg Asn Gly Ile Asp Glu Thr Ile Cys Thr Met Arg Leu Arg His
            290                 295                 300

Asn Ile Gly Gln Thr Ser Ser Pro Asp Ile Tyr Asn Pro Gln Ala Gly
305                 310                 315                 320

Ser Val Thr Thr Ala Thr Ser Leu Asp Phe Pro Ala Leu Ser Trp Leu
            325                 330                 335

Arg Leu Ser Ala Glu Phe Gly Ser Leu Arg Lys Asn Ala Met Phe Val
            340                 345                 350

Pro His Tyr Asn Leu Asn Ala Asn Ser Ile Ile Tyr Ala Leu Asn Gly
            355                 360                 365

Arg Ala Leu Ile Gln Val Val Asn Cys Asn Gly Glu Arg Val Phe Asp
            370                 375                 380

Gly Glu Leu Gln Glu Gly Arg Val Leu Ile Val Pro Gln Asn Phe Val
385                 390                 395                 400

Val Ala Ala Arg Ser Gln Ser Asp Asn Phe Glu Tyr Val Ser Phe Lys
            405                 410                 415

Thr Asn Asp Thr Pro Met Ile Gly Thr Leu Ala Gly Ala Asn Ser Leu
            420                 425                 430

Leu Asn Ala Leu Pro Glu Glu Val Ile Gln His Thr Phe Asn Leu Lys
            435                 440                 445

Ser Gln Gln Ala Arg Gln Ile Lys Asn Asn Pro Phe Lys Phe Leu
450                 455                 460

Val Pro Pro Gln Glu Ser Gln Lys Arg Ala Val Ala Gly Gly Gly Ser
465                 470                 475                 480

Ser Arg Glu Gln Pro Gln Gln Asn Glu Cys Gln Ile Gln Lys Leu Asn
            485                 490                 495

Ala Leu Lys Pro Asp Asn Arg Ile Glu Ser Glu Gly Gly Leu Ile Glu
            500                 505                 510
```

-continued

```
Thr Trp Asn Pro Asn Asn Lys Pro Phe Gln Cys Ala Gly Val Ala Leu
    515                 520                 525

Ser Arg Cys Thr Leu Asn Arg Asn Ala Leu Arg Arg Pro Ser Tyr Thr
    530                 535                 540

Asn Gly Pro Gln Glu Ile Tyr Ile Gln Gln Gly Lys Gly Ile Phe Gly
545                 550                 555                 560

Met Ile Tyr Pro Gly Cys Pro Ser Thr Phe Glu Glu Pro Gln Gln Pro
                565                 570                 575

Gln Gln Arg Gly Gln Ser Ser Arg Pro Gln Asp Arg His Gln Lys Ile
            580                 585                 590

Tyr Asn Phe Arg Glu Gly Asp Leu Ile Ala Val Pro Thr Gly Val Ala
        595                 600                 605

Trp Trp Met Tyr Asn Asn Glu Asp Thr Pro Val Ala Val Ser Ile
    610                 615                 620

Ile Asp Thr Asn Ser Leu Glu Asn Gln Leu Asp Gln Met Pro Arg Arg
625                 630                 635                 640

Phe Tyr Leu Ala Gly Asn Gln Glu Gln Glu Phe Leu Lys Tyr Gln Gln
                645                 650                 655

Glu Gln Gly Gly His Gln Ser Gln Lys Gly Lys His Gln Gln Glu Glu
            660                 665                 670

Glu Asn Glu Gly Gly Ser Ile Leu Ser Gly Phe Thr Leu Glu Phe Leu
        675                 680                 685

Glu His Ala Phe Ser Val Asp Lys Gln Ile Ala Lys Asn Leu Gln Gly
    690                 695                 700

Glu Asn Glu Gly Glu Asp Lys Gly Ala Ile Val Thr Val Lys Gly Gly
705                 710                 715                 720

Leu Ser Val Leu Lys Pro Pro Thr Asp Glu Gln Gln Gln Arg Pro Gln
                725                 730                 735

Glu Glu Glu Glu Glu Glu Asp Glu Lys Pro Gln Cys Lys Gly Lys
            740                 745                 750

Asp Lys His Cys Gln Arg Pro Arg Gly Ser Gln Ser Lys Ser Arg Arg
        755                 760                 765

Asn Gly Ile Asp Glu Thr Ile Cys Thr Met Arg Leu Arg His Asn Ile
    770                 775                 780

Gly Gln Thr Ser Ser Pro Asp Ile Tyr Asn Pro Gln Ala Gly Ser Val
785                 790                 795                 800

Thr Thr Ala Thr Ser Leu Asp Phe Pro Ala Leu Ser Trp Leu Arg Leu
                805                 810                 815

Ser Ala Glu Phe Gly Ser Leu Arg Lys Asn Ala Met Phe Val Pro His
            820                 825                 830

Tyr Asn Leu Asn Ala Asn Ser Ile Ile Tyr Ala Leu Asn Gly Arg Ala
        835                 840                 845

Leu Ile Gln Val Val Asn Cys Asn Gly Glu Arg Val Phe Asp Gly Glu
    850                 855                 860

Leu Gln Glu Gly Arg Val Leu Ile Val Pro Gln Asn Phe Val Val Ala
865                 870                 875                 880

Ala Arg Ser Gln Ser Asp Asn Phe Glu Tyr Val Ser Phe Lys Thr Asn
                885                 890                 895

Asp Thr Pro Met Ile Gly Thr Leu Ala Gly Ala Asn Ser Leu Leu Asn
            900                 905                 910

Ala Leu Pro Glu Glu Val Ile Gln His Thr Phe Asn Leu Lys Ser Gln
        915                 920                 925

Gln Ala Arg Gln Ile Lys Asn Asn Asn Pro Phe Lys Phe Leu Val Pro
```

```
                930             935             940
Pro Gln Glu Ser Gln Lys Arg Ala Val Ala
945             950

<210> SEQ ID NO 34
<211> LENGTH: 3069
<212> TYPE: DNA
<213> ORGANISM: Glycine max
<220> FEATURE:
<221> NAME/KEY: CDS
<222> LOCATION: (1)...(3069)
<223> OTHER INFORMATION: GlyaCG:  proglycinin1 fused to beta subunit of
      alpha-conglycinin with linker

<400> SEQUENCE: 34 atg ggt tcc aga gag cag cct cag caa aac gag tgc cag atc caa aaa      48
Met Gly Ser Arg Glu Gln Pro Gln Gln Asn Glu Cys Gln Ile Gln Lys
 1               5                  10                  15 ctc aat gcc ctc aaa ccg gat aac cgt ata gag tca gaa gga ggg ctc      96
Leu Asn Ala Leu Lys Pro Asp Asn Arg Ile Glu Ser Glu Gly Gly Leu
             20                  25                  30 att gag aca tgg aac cct aac aac aag cca ttc cag tgt gcc ggt gtt     144
Ile Glu Thr Trp Asn Pro Asn Asn Lys Pro Phe Gln Cys Ala Gly Val
         35                  40                  45 gcc ctc tct cgc tgc acc ctc aac cgc aac gcc ctt cgt aga cct tcc     192
Ala Leu Ser Arg Cys Thr Leu Asn Arg Asn Ala Leu Arg Arg Pro Ser
     50                  55                  60 tac acc aac ggt ccc cag gaa atc tac atc caa caa ggt aag ggt att     240
Tyr Thr Asn Gly Pro Gln Glu Ile Tyr Ile Gln Gln Gly Lys Gly Ile
 65                  70                  75                  80 ttt ggc atg ata tac ccg ggt tgt cct agc aca ttt gaa gag cct cag     288
Phe Gly Met Ile Tyr Pro Gly Cys Pro Ser Thr Phe Glu Glu Pro Gln
                 85                  90                  95 caa cct caa caa aga gga caa agc agc aga cca caa gac cgt cac cag     336
Gln Pro Gln Gln Arg Gly Gln Ser Ser Arg Pro Gln Asp Arg His Gln
            100                 105                 110 aag atc tat aac ttc aga gag ggt gat ttg atc gca gtg cct act ggt     384
Lys Ile Tyr Asn Phe Arg Glu Gly Asp Leu Ile Ala Val Pro Thr Gly
        115                 120                 125 gtt gca tgg tgg atg tac aac aat gaa gac act cct gtt gtt gcc gtt     432
Val Ala Trp Trp Met Tyr Asn Asn Glu Asp Thr Pro Val Val Ala Val
    130                 135                 140 tct att att gac acc aac agc ttg gag aac cag ctc gac cag atg cct     480
Ser Ile Ile Asp Thr Asn Ser Leu Glu Asn Gln Leu Asp Gln Met Pro
145                 150                 155                 160 agg aga ttc tat ctt gct ggg aac caa gag caa gag ttt cta aaa tat     528
Arg Arg Phe Tyr Leu Ala Gly Asn Gln Glu Gln Glu Phe Leu Lys Tyr
                165                 170                 175 cag caa gag caa gga ggt cat caa agc cag aaa gga aag cat cag caa     576
Gln Gln Glu Gln Gly Gly His Gln Ser Gln Lys Gly Lys His Gln Gln
            180                 185                 190 gaa gaa gaa aac gaa gga ggc agc ata ttg agt ggc ttc acc ctg gaa     624
Glu Glu Glu Asn Glu Gly Gly Ser Ile Leu Ser Gly Phe Thr Leu Glu
        195                 200                 205 ttc ttg gaa cat gca ttc agc gtg gac aag cag ata gcg aaa aac cta     672
Phe Leu Glu His Ala Phe Ser Val Asp Lys Gln Ile Ala Lys Asn Leu
    210                 215                 220 caa gga gag aac gaa ggg gaa gac aag gga gcc att gtg aca gtg aaa     720
Gln Gly Glu Asn Glu Gly Glu Asp Lys Gly Ala Ile Val Thr Val Lys
225                 230                 235                 240 gga ggt ctg agc gtg tta aaa cca ccc acg gac gag cag caa caa aga     768
```

-continued

```
                Gly Gly Leu Ser Val Leu Lys Pro Pro Thr Asp Glu Gln Gln Arg
                                245                 250                 255 ccc cag gaa gag gaa gaa gaa gag gat gag aag cca cag tgc aag            816
Pro Gln Glu Glu Glu Glu Glu Glu Asp Glu Lys Pro Gln Cys Lys
            260                 265                 270 ggt aaa gac aaa cac tgc caa cgc ccc cga gga agc caa agc aaa agc        864
Gly Lys Asp Lys His Cys Gln Arg Pro Arg Gly Ser Gln Ser Lys Ser
        275                 280                 285 aga aga aat ggc att gac gag acc ata tgc acc atg aga ctt cgc cac        912
Arg Arg Asn Gly Ile Asp Glu Thr Ile Cys Thr Met Arg Leu Arg His
    290                 295                 300 aac att ggc cag act tca tca cct gac atc tac aac cct caa gcc ggt        960
Asn Ile Gly Gln Thr Ser Ser Pro Asp Ile Tyr Asn Pro Gln Ala Gly
305                 310                 315                 320 agc gtc aca acc gcc acc agc ctt gac ttc cca gcc ctc tcg tgg ctc       1008
Ser Val Thr Thr Ala Thr Ser Leu Asp Phe Pro Ala Leu Ser Trp Leu
                325                 330                 335 aga ctc agt gct gag ttt gga tct ctc cgc aag aat gca atg ttc gtg       1056
Arg Leu Ser Ala Glu Phe Gly Ser Leu Arg Lys Asn Ala Met Phe Val
            340                 345                 350 cca cac tac aac ctg aac gcg aac agc ata ata tac gca ttg aat gga       1104
Pro His Tyr Asn Leu Asn Ala Asn Ser Ile Ile Tyr Ala Leu Asn Gly
        355                 360                 365 cgg gca ttg ata caa gtg gtg aat tgc aac ggt gag aga gtg ttt gat       1152
Arg Ala Leu Ile Gln Val Val Asn Cys Asn Gly Glu Arg Val Phe Asp
    370                 375                 380 gga gag ctg caa gag gga cgg gtg ctg atc gtg cca caa aac ttt gtg       1200
Gly Glu Leu Gln Glu Gly Arg Val Leu Ile Val Pro Gln Asn Phe Val
385                 390                 395                 400 gtg gct gca aga tca cag agt gac aac ttc gag tat gtg tca ttc aag       1248
Val Ala Ala Arg Ser Gln Ser Asp Asn Phe Glu Tyr Val Ser Phe Lys
                405                 410                 415 acc aat gat aca ccc atg atc ggc act ctt gca ggg gca aac tca ttg       1296
Thr Asn Asp Thr Pro Met Ile Gly Thr Leu Ala Gly Ala Asn Ser Leu
            420                 425                 430 ttg aac gca tta cca gag gaa gtg att cag cac act ttc aac cta aaa       1344
Leu Asn Ala Leu Pro Glu Glu Val Ile Gln His Thr Phe Asn Leu Lys
        435                 440                 445 agc cag cag gcc agg cag ata aag aac aac aac cct ttc aag ttc ctg       1392
Ser Gln Gln Ala Arg Gln Ile Lys Asn Asn Asn Pro Phe Lys Phe Leu
    450                 455                 460 gtt cca cct cag gag tct cag aag aga gct gtg gct ggt ggt gga tcc       1440
Val Pro Pro Gln Glu Ser Gln Lys Arg Ala Val Ala Gly Gly Gly Ser
465                 470                 475                 480 gtg gag aaa gaa gaa tgt gaa gaa ggt gaa att cca cga cca cga cca       1488
Val Glu Lys Glu Glu Cys Glu Glu Gly Glu Ile Pro Arg Pro Arg Pro
                485                 490                 495 cga cca caa cac ccg gag agg gaa cct cag caa ccc ggt gag aag gag       1536
Arg Pro Gln His Pro Glu Arg Glu Pro Gln Gln Pro Gly Glu Lys Glu
            500                 505                 510 gaa gac gaa gat gag caa cca cgt cca atc cca ttc cca cgc cca caa       1584
Glu Asp Glu Asp Glu Gln Pro Arg Pro Ile Pro Phe Pro Arg Pro Gln
        515                 520                 525 cct cgt caa gaa gaa gag cac gag cag aga gag gaa cag gaa tgg cct       1632
Pro Arg Gln Glu Glu Glu His Glu Gln Arg Glu Glu Gln Glu Trp Pro
    530                 535                 540 cgc aag gag gaa aaa cgc gga gaa aag gga agt gaa gag gaa gat gag       1680
Arg Lys Glu Glu Lys Arg Gly Glu Lys Gly Ser Glu Glu Glu Asp Glu
545                 550                 555                 560
```

```
gat gag gat gag gaa caa gat gaa cgt caa ttc cca ttc cca cgc cca       1728
Asp Glu Asp Glu Glu Gln Asp Glu Arg Gln Phe Pro Phe Pro Arg Pro
                565                 570                 575 cct cat cag aag gaa gag cga aac gaa gag gaa gat gag gat gag gag       1776
Pro His Gln Lys Glu Glu Arg Asn Glu Glu Glu Asp Glu Asp Glu Glu
                580                 585                 590 cag cag cga gag agc gaa gaa agt gaa gat tct gag tta cga aga cat       1824
Gln Gln Arg Glu Ser Glu Glu Ser Glu Asp Ser Glu Leu Arg Arg His
            595                 600                 605 aag aat aag aac cct ttt ctc ttc ggc tct aac agg ttc gaa act ctc       1872
Lys Asn Lys Asn Pro Phe Leu Phe Gly Ser Asn Arg Phe Glu Thr Leu
        610                 615                 620 ttc aaa aac caa tat ggt cgc att cgc gtc ctc cag agg ttc aac caa       1920
Phe Lys Asn Gln Tyr Gly Arg Ile Arg Val Leu Gln Arg Phe Asn Gln
625                 630                 635                 640 cgc tcc cca caa ctt cag aat ctc cga gac tac cgc att ttg gag ttc       1968
Arg Ser Pro Gln Leu Gln Asn Leu Arg Asp Tyr Arg Ile Leu Glu Phe
                645                 650                 655 aac tcc aaa ccc aac acc ctc ctt ctc ccc aac cat gct gac gct gat       2016
Asn Ser Lys Pro Asn Thr Leu Leu Leu Pro Asn His Ala Asp Ala Asp
                660                 665                 670 tac ctc atc gtt atc ctt aac ggg act gcc att ctt tcc ttg gtg aac       2064
Tyr Leu Ile Val Ile Leu Asn Gly Thr Ala Ile Leu Ser Leu Val Asn
            675                 680                 685 aac gac gac aga gac tcc tac aga ctt caa tct ggt gat gcc ctg aga       2112
Asn Asp Asp Arg Asp Ser Tyr Arg Leu Gln Ser Gly Asp Ala Leu Arg
        690                 695                 700 gtc ccc tca gga acc aca tac tat gtg gtc aac cct gac aac aac gaa       2160
Val Pro Ser Gly Thr Thr Tyr Tyr Val Val Asn Pro Asp Asn Asn Glu
705                 710                 715                 720 aat ctc aga tta ata aca ctc gcc ata ccc gtt aac aag cct ggt aga       2208
Asn Leu Arg Leu Ile Thr Leu Ala Ile Pro Val Asn Lys Pro Gly Arg
                725                 730                 735 ttt gag agt ttc ttc cta tct agc act gaa gct caa caa tcc tac ttg       2256
Phe Glu Ser Phe Phe Leu Ser Ser Thr Glu Ala Gln Gln Ser Tyr Leu
                740                 745                 750 caa gga ttc agc agg aac att tta gag gcc tcc tac gat acc aaa ttc       2304
Gln Gly Phe Ser Arg Asn Ile Leu Glu Ala Ser Tyr Asp Thr Lys Phe
            755                 760                 765 gag gag ata aac aag gtt ctg ttt agt aga gag gaa ggg cag cag caa       2352
Glu Glu Ile Asn Lys Val Leu Phe Ser Arg Glu Glu Gly Gln Gln Gln
        770                 775                 780 ggg gag cag agg ctg caa gag agc gtg att gtg gaa atc tcg aag gaa       2400
Gly Glu Gln Arg Leu Gln Glu Ser Val Ile Val Glu Ile Ser Lys Glu
785                 790                 795                 800 cag att cgg gca ctg agc aaa cgt gcc aaa tct agt tca agg aaa acc       2448
Gln Ile Arg Ala Leu Ser Lys Arg Ala Lys Ser Ser Arg Lys Thr
                805                 810                 815 att tct tct gaa gat aaa cct ttt aac ttg aga agc cgc gac ccc atc       2496
Ile Ser Ser Glu Asp Lys Pro Phe Asn Leu Arg Ser Arg Asp Pro Ile
                820                 825                 830 tac tcc aac aag ctt ggc aag ttc ttt gag atc acc cca gag aaa aac       2544
Tyr Ser Asn Lys Leu Gly Lys Phe Phe Glu Ile Thr Pro Glu Lys Asn
            835                 840                 845 ccc cag ctt cgg gac ttg gat atc ttc ctc agt att gtg gat atg aac       2592
Pro Gln Leu Arg Asp Leu Asp Ile Phe Leu Ser Ile Val Asp Met Asn
        850                 855                 860 gag gga gct ctt ctt cta cca cac ttc aat tca aag gcg ata gtg ata       2640
Glu Gly Ala Leu Leu Leu Pro His Phe Asn Ser Lys Ala Ile Val Ile
865                 870                 875                 880
```

```
ctg gta att aat gaa gga gat gca aac att gaa ctt gtt ggc cta aaa    2688
Leu Val Ile Asn Glu Gly Asp Ala Asn Ile Glu Leu Val Gly Leu Lys
            885                 890                 895 gaa caa caa cag gag cag caa cag gaa gag caa cct ttg gaa gtg cgg    2736
Glu Gln Gln Gln Glu Gln Gln Gln Glu Glu Gln Pro Leu Glu Val Arg
        900                 905                 910 aaa tat aga gcc gaa ttg tct gaa caa gat ata ttt gta atc cca gca    2784
Lys Tyr Arg Ala Glu Leu Ser Glu Gln Asp Ile Phe Val Ile Pro Ala
    915                 920                 925 ggt tat cca gtt gtg gtc aac gct acc tca aat ctg aat ttc ttt gct    2832
Gly Tyr Pro Val Val Val Asn Ala Thr Ser Asn Leu Asn Phe Phe Ala
930                 935                 940 att ggt att aat gcc gag aac aac cag agg aac ttc ctc gca ggt tcg    2880
Ile Gly Ile Asn Ala Glu Asn Asn Gln Arg Asn Phe Leu Ala Gly Ser
945                 950                 955                 960 caa gac aat gtg ata agc cag ata cct agt caa gtg cag gag ctt gca    2928
Gln Asp Asn Val Ile Ser Gln Ile Pro Ser Gln Val Gln Glu Leu Ala
                965                 970                 975 ttc cct ggg tct gca caa gct gtt gag aag cta tta aag aac caa aga    2976
Phe Pro Gly Ser Ala Gln Ala Val Glu Lys Leu Leu Lys Asn Gln Arg
            980                 985                 990 gaa tcc tac ttt gtg gat gct cag cct aag aag aaa gag gag ggg aat    3024
Glu Ser Tyr Phe Val Asp Ala Gln Pro Lys Lys Lys Glu Glu Gly Asn
        995                 1000                1005 aag gga aga aag ggt cct ttg tct tca att ttg agg gct ttt tac        3069
Lys Gly Arg Lys Gly Pro Leu Ser Ser Ile Leu Arg Ala Phe Tyr
    1010                1015                1020

<210> SEQ ID NO 35
<211> LENGTH: 1023
<212> TYPE: PRT
<213> ORGANISM: Glycine max

<400> SEQUENCE: 35

Met Gly Ser Arg Glu Gln Pro Gln Gln Asn Glu Cys Gln Ile Gln Lys
1               5                   10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gly Lys Gly Ile
65              70                  75                  80

Phe Gly Met Ile Tyr Pro Gly Cys Pro Ser Thr Phe Glu Glu Pro Gln
                85                  90                  95

Gln Pro Gln Gln Arg Gly Gln Ser Ser Arg Pro Gln Asp Arg His Gln
            100                 105                 110

Lys Ile Tyr Asn Phe Arg Glu Gly Asp Leu Ile Ala Val Pro Thr Gly
        115                 120                 125

Val Ala Trp Trp Met Tyr Asn Asn Glu Asp Thr Pro Val Val Ala Val
    130                 135                 140

Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
                165                 170                 175

Gln Gln Glu Gln Gly Gly His Gln Ser Gln Lys Gly Lys His Gln Gln
```

```
            180             185             190
Glu Glu Glu Asn Glu Gly Gly Ser Ile Leu Ser Gly Phe Thr Leu Glu
        195                 200                 205
Phe Leu Glu His Ala Phe Ser Val Asp Lys Gln Ile Ala Lys Asn Leu
        210                 215                 220
Gln Gly Glu Asn Glu Gly Glu Asp Lys Gly Ala Ile Val Thr Val Lys
225                 230                 235                 240
Gly Gly Leu Ser Val Leu Lys Pro Pro Thr Asp Glu Gln Gln Gln Arg
                245                 250                 255
Pro Gln Glu Glu Glu Glu Glu Glu Asp Glu Lys Pro Gln Cys Lys
        260                 265                 270
Gly Lys Asp Lys His Cys Gln Arg Pro Arg Gly Ser Gln Ser Lys Ser
        275                 280                 285
Arg Arg Asn Gly Ile Asp Glu Thr Ile Cys Thr Met Arg Leu Arg His
        290                 295                 300
Asn Ile Gly Gln Thr Ser Ser Pro Asp Ile Tyr Asn Pro Gln Ala Gly
305                 310                 315                 320
Ser Val Thr Thr Ala Thr Ser Leu Asp Phe Pro Ala Leu Ser Trp Leu
                325                 330                 335
Arg Leu Ser Ala Glu Phe Gly Ser Leu Arg Lys Asn Ala Met Phe Val
                340                 345                 350
Pro His Tyr Asn Leu Asn Ala Asn Ser Ile Ile Tyr Ala Leu Asn Gly
            355                 360                 365
Arg Ala Leu Ile Gln Val Val Asn Cys Asn Gly Glu Arg Val Phe Asp
        370                 375                 380
Gly Glu Leu Gln Glu Gly Arg Val Leu Ile Val Pro Gln Asn Phe Val
385                 390                 395                 400
Val Ala Ala Arg Ser Gln Ser Asp Asn Phe Glu Tyr Val Ser Phe Lys
                405                 410                 415
Thr Asn Asp Thr Pro Met Ile Gly Thr Leu Ala Gly Ala Asn Ser Leu
                420                 425                 430
Leu Asn Ala Leu Pro Glu Glu Val Ile Gln His Thr Phe Asn Leu Lys
                435                 440                 445
Ser Gln Gln Ala Arg Gln Ile Lys Asn Asn Asn Pro Phe Lys Phe Leu
        450                 455                 460
Val Pro Pro Gln Glu Ser Gln Lys Arg Ala Val Ala Gly Gly Gly Ser
465                 470                 475                 480
Val Glu Lys Glu Glu Cys Glu Glu Gly Glu Ile Pro Arg Pro Arg Pro
                485                 490                 495
Arg Pro Gln His Pro Glu Arg Glu Pro Gln Gln Pro Gly Glu Lys Glu
            500                 505                 510
Glu Asp Glu Asp Glu Gln Pro Arg Pro Ile Pro Phe Pro Arg Pro Gln
        515                 520                 525
Pro Arg Gln Glu Glu Glu His Glu Gln Arg Glu Glu Gln Glu Trp Pro
        530                 535                 540
Arg Lys Glu Glu Lys Arg Gly Glu Lys Gly Ser Glu Glu Glu Asp Glu
545                 550                 555                 560
Asp Glu Asp Glu Glu Gln Asp Glu Arg Gln Phe Pro Phe Pro Arg Pro
                565                 570                 575
Pro His Gln Lys Glu Glu Arg Asn Glu Glu Glu Asp Glu Asp Glu Glu
            580                 585                 590
Gln Gln Arg Glu Ser Glu Glu Ser Glu Asp Ser Glu Leu Arg Arg His
        595                 600                 605
```

-continued

```
Lys Asn Lys Asn Pro Phe Leu Phe Gly Ser Asn Arg Phe Glu Thr Leu
    610                 615                 620
Phe Lys Asn Gln Tyr Gly Arg Ile Arg Val Leu Gln Arg Phe Asn Gln
625                 630                 635                 640
Arg Ser Pro Gln Leu Gln Asn Leu Arg Asp Tyr Arg Ile Leu Glu Phe
                    645                 650                 655
Asn Ser Lys Pro Asn Thr Leu Leu Pro Asn His Ala Asp Ala Asp
                660                 665                 670
Tyr Leu Ile Val Ile Leu Asn Gly Thr Ala Ile Leu Ser Leu Val Asn
            675                 680                 685
Asn Asp Asp Arg Asp Ser Tyr Arg Leu Gln Ser Gly Asp Ala Leu Arg
690                 695                 700
Val Pro Ser Gly Thr Thr Tyr Tyr Val Val Asn Pro Asp Asn Asn Glu
705                 710                 715                 720
Asn Leu Arg Leu Ile Thr Leu Ala Ile Pro Val Asn Lys Pro Gly Arg
                    725                 730                 735
Phe Glu Ser Phe Phe Leu Ser Ser Thr Glu Ala Gln Gln Ser Tyr Leu
                740                 745                 750
Gln Gly Phe Ser Arg Asn Ile Leu Glu Ala Ser Tyr Asp Thr Lys Phe
            755                 760                 765
Glu Glu Ile Asn Lys Val Leu Phe Ser Arg Glu Glu Gly Gln Gln Gln
770                 775                 780
Gly Glu Gln Arg Leu Gln Glu Ser Val Ile Val Glu Ile Ser Lys Glu
785                 790                 795                 800
Gln Ile Arg Ala Leu Ser Lys Arg Ala Lys Ser Ser Arg Lys Thr
                    805                 810                 815
Ile Ser Ser Glu Asp Lys Pro Phe Asn Leu Arg Ser Arg Asp Pro Ile
                820                 825                 830
Tyr Ser Asn Lys Leu Gly Lys Phe Phe Glu Ile Thr Pro Glu Lys Asn
            835                 840                 845
Pro Gln Leu Arg Asp Leu Asp Ile Phe Leu Ser Ile Val Asp Met Asn
850                 855                 860
Glu Gly Ala Leu Leu Leu Pro His Phe Asn Ser Lys Ala Ile Val Ile
865                 870                 875                 880
Leu Val Ile Asn Glu Gly Asp Ala Asn Ile Glu Leu Val Gly Leu Lys
                    885                 890                 895
Glu Gln Gln Gln Glu Gln Gln Glu Gln Pro Leu Glu Val Arg
                900                 905                 910
Lys Tyr Arg Ala Glu Leu Ser Glu Gln Asp Ile Phe Val Ile Pro Ala
            915                 920                 925
Gly Tyr Pro Val Val Val Asn Ala Thr Ser Asn Leu Asn Phe Phe Ala
930                 935                 940
Ile Gly Ile Asn Ala Glu Asn Asn Gln Arg Asn Phe Leu Ala Gly Ser
945                 950                 955                 960
Gln Asp Asn Val Ile Ser Gln Ile Pro Ser Gln Val Gln Glu Leu Ala
                    965                 970                 975
Phe Pro Gly Ser Ala Gln Ala Val Glu Lys Leu Leu Lys Asn Gln Arg
                980                 985                 990
Glu Ser Tyr Phe Val Asp Ala Gln Pro Lys Lys Glu Glu Gly Asn
            995                 1000                1005
Lys Gly Arg Lys Gly Pro Leu Ser Ser Ile Leu Arg Ala Phe Tyr
    1010                1015                1020
```

<210> SEQ ID NO 36
<211> LENGTH: 6
<212> TYPE: PRT
<213> ORGANISM: Artificial Sequence
<220> FEATURE:
<223> OTHER INFORMATION: GlyF2: C-terminal fusion peptide

<400> SEQUENCE: 36

Gly Gly Gly Ser Phe Phe
 1               5

<210> SEQ ID NO 37
<211> LENGTH: 8
<212> TYPE: PRT
<213> ORGANISM: Artificial Sequence
<220> FEATURE:
<223> OTHER INFORMATION: GlyF4: C terminal fusion peptide

<400> SEQUENCE: 37

Gly Gly Gly Ser Phe Phe Phe Phe
 1               5

<210> SEQ ID NO 38
<211> LENGTH: 10
<212> TYPE: PRT
<213> ORGANISM: Artificial Sequence
<220> FEATURE:
<223> OTHER INFORMATION: GlyF6: C terminal fusion peptide

<400> SEQUENCE: 38

Gly Gly Gly Ser Phe Phe Phe Phe Phe Phe
 1               5                  10

<210> SEQ ID NO 39
<211> LENGTH: 1806
<212> TYPE: DNA
<213> ORGANISM: Glycine max
<220> FEATURE:
<221> NAME/KEY: CDS
<222> LOCATION: (1)...(1806)
<223> OTHER INFORMATION: acgeGly: alpha subunit of beta-conglycinin ext
      region fused to N-terminus of proglycinin 1

<400> SEQUENCE: 39

```
atg gcg gtg gag aaa gaa gaa tgt gaa gaa ggt gaa att cca cga cca      48
Met Ala Val Glu Lys Glu Glu Cys Glu Glu Gly Glu Ile Pro Arg Pro
 1               5                  10                  15 cga cca cga cca caa cac ccg gag agg gaa cct cag caa ccc ggt gag      96
Arg Pro Arg Pro Gln His Pro Glu Arg Glu Pro Gln Gln Pro Gly Glu
                20                  25                  30 aag gag gaa gac gaa gat gag caa cca cgt cca atc cca ttc cca cgc     144
Lys Glu Glu Asp Glu Asp Glu Gln Pro Arg Pro Ile Pro Phe Pro Arg
            35                  40                  45 cca caa cct cgt caa gaa gaa gag cac gag cag aga gag gaa cag gaa     192
Pro Gln Pro Arg Gln Glu Glu His Glu Gln Arg Glu Glu Gln Glu
        50                  55                  60 tgg cct cgc aag gag gaa aaa cgc gga gaa aag gga agt gaa gag gaa     240
Trp Pro Arg Lys Glu Glu Lys Arg Gly Glu Lys Gly Ser Glu Glu Glu
 65                  70                  75                  80 gat gag gat gag gat gag gaa caa gat gaa cgt caa ttc cca ttc ccg     288
Asp Glu Asp Glu Asp Glu Glu Gln Asp Glu Arg Gln Phe Pro Phe Pro
                85                  90                  95 cgg ccg cct cat cag aag gaa gag cga aac gaa gag gaa gat gag gat     336
Arg Pro Pro His Gln Lys Glu Glu Arg Asn Glu Glu Glu Asp Glu Asp
                100                 105                 110
```

-continued

| | |
|---|---|
| gag gag cag cag cga gag agc gaa gaa agt gaa gat tct gag gga tcc<br>Glu Glu Gln Gln Arg Glu Ser Glu Glu Ser Glu Asp Ser Glu Gly Ser<br>115                   120                   125 | 384 |
| tcc aga gag cag cct cag caa aac gag tgc cag atc caa aaa ctc aat<br>Ser Arg Glu Gln Pro Gln Gln Asn Glu Cys Gln Ile Gln Lys Leu Asn<br>130                   135                   140 | 432 |
| gcc ctc aaa ccg gat aac cgt ata gag tca gaa gga ggg ctc att gag<br>Ala Leu Lys Pro Asp Asn Arg Ile Glu Ser Glu Gly Gly Leu Ile Glu<br>145                   150                   155                   160 | 480 |
| aca tgg aac cct aac aac aag cca ttc cag tgt gcc ggt gtt gcc ctc<br>Thr Trp Asn Pro Asn Asn Lys Pro Phe Gln Cys Ala Gly Val Ala Leu<br>                   165                   170                   175 | 528 |
| tct cgc tgc acc ctc aac cgc aac gcc ctt cgt aga cct tcc tac acc<br>Ser Arg Cys Thr Leu Asn Arg Asn Ala Leu Arg Arg Pro Ser Tyr Thr<br>                   180                   185                   190 | 576 |
| aac ggt ccc cag gaa atc tac atc caa caa ggt aag ggt att ttt ggc<br>Asn Gly Pro Gln Glu Ile Tyr Ile Gln Gln Gly Lys Gly Ile Phe Gly<br>         195                   200                   205 | 624 |
| atg ata tac ccg ggt tgt cct agc aca ttt gaa gag cct cag caa cct<br>Met Ile Tyr Pro Gly Cys Pro Ser Thr Phe Glu Glu Pro Gln Gln Pro<br>210                   215                   220 | 672 |
| caa caa aga gga caa agc agc aga cca caa gac cgt cac cag aag atc<br>Gln Gln Arg Gly Gln Ser Ser Arg Pro Gln Asp Arg His Gln Lys Ile<br>225                   230                   235                   240 | 720 |
| tat aac ttc aga gag ggt gat ttg atc gca gtg cct act ggt gtt gca<br>Tyr Asn Phe Arg Glu Gly Asp Leu Ile Ala Val Pro Thr Gly Val Ala<br>                   245                   250                   255 | 768 |
| tgg tgg atg tac aac aat gaa gac act cct gtt gtt gcc gtt tct att<br>Trp Trp Met Tyr Asn Asn Glu Asp Thr Pro Val Val Ala Val Ser Ile<br>                   260                   265                   270 | 816 |
| att gac acc aac agc ttg gag aac cag ctc gac cag atg cct agg aga<br>Ile Asp Thr Asn Ser Leu Glu Asn Gln Leu Asp Gln Met Pro Arg Arg<br>                   275                   280                   285 | 864 |
| ttc tat ctt gct ggg aac caa gag caa gag ttt cta aaa tat cag caa<br>Phe Tyr Leu Ala Gly Asn Gln Glu Gln Glu Phe Leu Lys Tyr Gln Gln<br>290                   295                   300 | 912 |
| gag caa gga ggt cat caa agc cag aaa gga aag cat cag caa gaa gaa<br>Glu Gln Gly Gly His Gln Ser Gln Lys Gly Lys His Gln Gln Glu Glu<br>305                   310                   315                   320 | 960 |
| gaa aac gaa gga ggc agc ata ttg agt ggc ttc acc ctg gaa ttc ttg<br>Glu Asn Glu Gly Gly Ser Ile Leu Ser Gly Phe Thr Leu Glu Phe Leu<br>                   325                   330                   335 | 1008 |
| gaa cat gca ttc agc gtg gac aag cag ata gcg aaa aac cta caa gga<br>Glu His Ala Phe Ser Val Asp Lys Gln Ile Ala Lys Asn Leu Gln Gly<br>                   340                   345                   350 | 1056 |
| gag aac gaa ggg gaa gac aag gga gcc att gtg aca gtg aaa gga ggt<br>Glu Asn Glu Gly Glu Asp Lys Gly Ala Ile Val Thr Val Lys Gly Gly<br>                   355                   360                   365 | 1104 |
| ctg agc gtg tta aaa cca ccc acg gac gag cag caa caa aga ccc cag<br>Leu Ser Val Leu Lys Pro Pro Thr Asp Glu Gln Gln Gln Arg Pro Gln<br>370                   375                   380 | 1152 |
| gaa gag gaa gaa gaa gaa gag gat gag aag cca cag tgc aag ggt aaa<br>Glu Glu Glu Glu Glu Glu Glu Asp Glu Lys Pro Gln Cys Lys Gly Lys<br>385                   390                   395                   400 | 1200 |
| gac aaa cac tgc caa cgc ccc cga gga agc caa agc aaa agc aga aga<br>Asp Lys His Cys Gln Arg Pro Arg Gly Ser Gln Ser Lys Ser Arg Arg<br>                   405                   410                   415 | 1248 |
| aat ggc att gac gag acc ata tgc acc atg aga ctt cgc cac aac att<br>Asn Gly Ile Asp Glu Thr Ile Cys Thr Met Arg Leu Arg His Asn Ile | 1296 |

```
                    420                 425                 430
ggc cag act tca tca cct gac atc tac aac cct caa gcc ggt agc gtc    1344
Gly Gln Thr Ser Ser Pro Asp Ile Tyr Asn Pro Gln Ala Gly Ser Val
            435                 440                 445 aca acc gcc acc agc ctt gac ttc cca gcc ctc tcg tgg ctc aga ctc    1392
Thr Thr Ala Thr Ser Leu Asp Phe Pro Ala Leu Ser Trp Leu Arg Leu
    450                 455                 460 agt gct gag ttt gga tct ctc cgc aag aat gca atg ttc gtg cca cac    1440
Ser Ala Glu Phe Gly Ser Leu Arg Lys Asn Ala Met Phe Val Pro His
465                 470                 475                 480 tac aac ctg aac gcg aac agc ata ata tac gca ttg aat gga cgg gca    1488
Tyr Asn Leu Asn Ala Asn Ser Ile Ile Tyr Ala Leu Asn Gly Arg Ala
                485                 490                 495 ttg ata caa gtg gtg aat tgc aac ggt gag aga gtg ttt gat gga gag    1536
Leu Ile Gln Val Val Asn Cys Asn Gly Glu Arg Val Phe Asp Gly Glu
            500                 505                 510 ctg caa gag gga cgg gtg ctg atc gtg cca caa aac ttt gtg gtg gct    1584
Leu Gln Glu Gly Arg Val Leu Ile Val Pro Gln Asn Phe Val Val Ala
        515                 520                 525 gca aga tca cag agt gac aac ttc gag tat gtg tca ttc aag acc aat    1632
Ala Arg Ser Gln Ser Asp Asn Phe Glu Tyr Val Ser Phe Lys Thr Asn
    530                 535                 540 gat aca ccc atg atc ggc act ctt gca ggg gca aac tca ttg ttg aac    1680
Asp Thr Pro Met Ile Gly Thr Leu Ala Gly Ala Asn Ser Leu Leu Asn
545                 550                 555                 560 gca tta cca gag gaa gtg att cag cac act ttc aac cta aaa agc cag    1728
Ala Leu Pro Glu Glu Val Ile Gln His Thr Phe Asn Leu Lys Ser Gln
                565                 570                 575 cag gcc agg cag ata aag aac aac aac cct ttc aag ttc ctg gtt cca    1776
Gln Ala Arg Gln Ile Lys Asn Asn Asn Pro Phe Lys Phe Leu Val Pro
            580                 585                 590 cct cag gag tct cag aag aga gct gtg gct                            1806
Pro Gln Glu Ser Gln Lys Arg Ala Val Ala
        595                 600

<210> SEQ ID NO 40
<211> LENGTH: 602
<212> TYPE: PRT
<213> ORGANISM: Glycine max

<400> SEQUENCE: 40

Met Ala Val Glu Lys Glu Glu Cys Glu Glu Gly Glu Ile Pro Arg Pro
1               5                   10                  15

Arg Pro Arg Pro Gln His Pro Glu Arg Glu Pro Gln Pro Gly Glu
            20                  25                  30

Lys Glu Glu Asp Glu Asp Glu Gln Pro Arg Pro Ile Pro Phe Pro Arg
        35                  40                  45

Pro Gln Pro Arg Gln Glu Glu His Glu Gln Arg Glu Glu Gln Glu
    50                  55                  60

Trp Pro Arg Lys Glu Glu Lys Arg Gly Glu Lys Gly Ser Glu Glu Glu
65                  70                  75                  80

Asp Glu Asp Glu Asp Glu Gln Asp Glu Arg Gln Phe Pro Phe Pro
                85                  90                  95

Arg Pro Pro His Gln Lys Glu Glu Arg Asn Glu Glu Asp Glu Asp
            100                 105                 110

Glu Glu Gln Gln Arg Glu Ser Glu Ser Glu Asp Ser Glu Gly Ser
        115                 120                 125

Ser Arg Glu Gln Pro Gln Gln Asn Glu Cys Gln Ile Gln Lys Leu Asn
```

-continued

```
            130                 135                 140
Ala Leu Lys Pro Asp Asn Arg Ile Glu Ser Glu Gly Gly Leu Ile Glu
145                 150                 155                 160

Thr Trp Asn Pro Asn Asn Lys Pro Phe Gln Cys Ala Gly Val Ala Leu
                165                 170                 175

Ser Arg Cys Thr Leu Asn Arg Asn Ala Leu Arg Arg Pro Ser Tyr Thr
                180                 185                 190

Asn Gly Pro Gln Glu Ile Tyr Ile Gln Gln Gly Lys Gly Ile Phe Gly
                195                 200                 205

Met Ile Tyr Pro Gly Cys Pro Ser Thr Phe Glu Glu Pro Gln Gln Pro
210                 215                 220

Gln Gln Arg Gly Gln Ser Ser Arg Pro Gln Asp Arg His Gln Lys Ile
225                 230                 235                 240

Tyr Asn Phe Arg Glu Gly Asp Leu Ile Ala Val Pro Thr Gly Val Ala
                245                 250                 255

Trp Trp Met Tyr Asn Asn Glu Asp Thr Pro Val Val Ala Val Ser Ile
                260                 265                 270

Ile Asp Thr Asn Ser Leu Glu Asn Gln Leu Asp Gln Met Pro Arg Arg
                275                 280                 285

Phe Tyr Leu Ala Gly Asn Gln Glu Gln Glu Phe Leu Lys Tyr Gln Gln
                290                 295                 300

Glu Gln Gly Gly His Gln Ser Gln Lys Gly Lys His Gln Gln Glu Glu
305                 310                 315                 320

Glu Asn Glu Gly Gly Ser Ile Leu Ser Gly Phe Thr Leu Glu Phe Leu
                325                 330                 335

Glu His Ala Phe Ser Val Asp Lys Gln Ile Ala Lys Asn Leu Gln Gly
                340                 345                 350

Glu Asn Glu Gly Glu Asp Lys Gly Ala Ile Val Thr Val Lys Gly Gly
                355                 360                 365

Leu Ser Val Leu Lys Pro Pro Thr Asp Glu Gln Gln Gln Arg Pro Gln
370                 375                 380

Glu Glu Glu Glu Glu Glu Asp Glu Lys Pro Gln Cys Lys Gly Lys
385                 390                 395                 400

Asp Lys His Cys Gln Arg Pro Arg Gly Ser Gln Ser Lys Ser Arg Arg
                405                 410                 415

Asn Gly Ile Asp Glu Thr Ile Cys Thr Met Arg Leu Arg His Asn Ile
                420                 425                 430

Gly Gln Thr Ser Ser Pro Asp Ile Tyr Asn Pro Gln Ala Gly Ser Val
                435                 440                 445

Thr Thr Ala Thr Ser Leu Asp Phe Pro Ala Leu Ser Trp Leu Arg Leu
450                 455                 460

Ser Ala Glu Phe Gly Ser Leu Arg Lys Asn Ala Met Phe Val Pro His
465                 470                 475                 480

Tyr Asn Leu Asn Ala Asn Ser Ile Ile Tyr Ala Leu Asn Gly Arg Ala
                485                 490                 495

Leu Ile Gln Val Val Asn Cys Asn Gly Glu Arg Val Phe Asp Gly Glu
                500                 505                 510

Leu Gln Glu Gly Arg Val Leu Ile Val Pro Gln Asn Phe Val Val Ala
                515                 520                 525

Ala Arg Ser Gln Ser Asp Asn Phe Glu Tyr Val Ser Phe Lys Thr Asn
                530                 535                 540

Asp Thr Pro Met Ile Gly Thr Leu Ala Gly Ala Asn Ser Leu Leu Asn
545                 550                 555                 560
```

-continued

```
Ala Leu Pro Glu Glu Val Ile Gln His Thr Phe Asn Leu Lys Ser Gln
            565                 570                 575

Gln Ala Arg Gln Ile Lys Asn Asn Asn Pro Phe Lys Phe Leu Val Pro
            580                 585                 590

Pro Gln Glu Ser Gln Lys Arg Ala Val Ala
            595                 600
```

US 7,160,988 B1

ALTERING PROTEIN FUNCTIONAL PROPERTIES THROUGH TERMINAL FUSIONS

CROSS-REFERENCE TO RELATED APPLICATIONS

This application claims priority to U.S. Provisional Application Ser. No. 60/453,132 filed Mar. 7, 2003, the contents of which are incorporated herein by reference.

BACKGROUND OF THE INVENTION

Glycinin is a major soybean seed storage protein used extensively in soy food products. However, these proteins have functional properties that do not make them ideally suited in all product applications.

It has been found that the functional properties (emulsification, gelation, solubility, etc.) of a protein are directly related to amino acid composition, sequence, and structure. Therefore, the properties can be altered through protein engineering.

Currently, improvement in soy protein functionality has been achieved through protein engineering of the core amino acid sequence. However, these alterations are limited due to the necessity of maintaining the wild-type three-dimensional structure so that the protein can assemble correctly.

The present invention provides methods and compositions for changing the properties of glycinin without having to alter the core structure responsible for correct assembly. This approach provides greater flexibility, allowing more radical changes than might be tolerated by alterations to the native protein structure.

DETAILED DESCRIPTION OF THE INVENTION

Glycinin is an 11S soybean globulin composed of six subunits. Each subunit is synthesized as a single polypeptide precursor containing an acidic region, a basic region, and an endoplasmic reticulum (ER) signal peptide. This precursor is preproglycinin. The signal peptide is removed by a first cleavage in the endoplasmic reticulum and the subunits assemble into trimers to form proglycinin. Preferably, modifications to the protein sequence should not disrupt this formation of trimers, because monomers are proteolytically unstable and unlikely to accumulate to useful levels. The proglycinin trimers move into protein storage vacuoles where a post-translational (second) cleavage by the vacuolar processing enzyme (VPE) results in hexamers that are glycinin. This second cleavage, between an asparagine and glycine residue at the junction of the acidic and basic regions, is highly conserved and considered a diagnostic characteristic of 11S globulins (see, for example, PubMed accession number M36686); (Dickinson et al., Plant Cell 1:459–469 (1989); Jung et al., Plant Cell 10:343–357 (1998). Improved functional properties of either proglycinin trimers or glycinin hexamers are potentially useful. It is thought that evaluation of the assembly and functional properties of E. coli-expressed proglycinin mutants is helpful in predicting properties of the corresponding glycinin mutants (Kim et al., Agric. Biol. Chem. 54:1543–1550 (1990); Kim et al., Protein Eng. 3:725–731 (1990)).

Glycinin polypeptides are encoded primarily by 5 genes: Gy1, Gy2, Gy3, Gy4, and Gy5, (Nielsen et al., Plant Cell 1:313–328 (1989)), and to a lesser extent by at least one other gene, Gy7 (Beilinson et al., Theor. Appl. Genet. 104:1132–1140 (2002)). In soybeans, glycinin hexamers are comprised of a heterogeneous mixture of the different glycinin gene products in various ratios. Changes in properties of any of the polypeptides encoded by any of the glycinin genes are potentially useful in improving functional properties.

Proglycinin1 and proglycinin4 (products of the Gy1 and Gy4 genes) were previously modified at non-conserved regions of the sequence to try to improve nutritional value or functional properties (Kim et al., Protein Eng. 3:725–731 (1990); Dickinson et al., Plant Cell 2:403–413 (1990)). Some, but not all of the mutant polypeptides assembled into trimers. Deletion of proglycinin disulfide bonds was also examined to assess effects on functional properties (Utsumi et al., J. Agric. Food Chem. 41:687–691 (1993). However, fusion of polypeptides to proglycinin or glycinin for the purpose of improving functional properties has not been previously explored.

The reporter protein chloramphenicol acetyl transferase was fused to the C-terminus of legumin, a glycinin homolog from Vicia faba, in order to study assembly and processing of 11S globulins. The fusion protein did not accumulate in plants, however, suggesting that the approach of fusing proteins to 11S globulins would be difficult. (Jung et al., J. of Exp. Botany 44:343–349).

It has been unexpectedly found that terminal fusions facilitate a change in the properties of the protein without having to alter the glycinin or proglycinin core sequence. Further, it is feasible to alter protein functional properties by the selection of fusion partners that possess the desired characteristics.

The fusion proteins of the present invention are produced by creating DNA constructs operably linking nucleic acid sequences encoding polypeptides having desired characteristics (e.g., acidic, basic, hydrophobic, hydrophilic), to a nucleic acid sequence encoding a soybean proglycinin polypeptide at either the C or N terminus, or both. The construct can include a linker sequence between proglycinin and the polypeptide being fused to it. The construct is then inserted into an expression cassette for transformation into plants or into bacterial expression systems. The fusion proteins can be produced in the hexameric glycinin form through expression in plants, or through expression in E. coli and subsequently adding VPE to the purified protein. Alternatively, the fusion proteins could be made in the trimeric, proglycinin (unprocessed), form through expression in E. coli and not adding VPE to the purified protein, or through expression in plants that are deficient in VPE activity (Gruis et al., Plant Cell 14:2863–2882, (2002); Gruis et al., Plant Cell 16:270–290 (2004)), or through expression in plants in a subcellular location different from the VPE location (Kinney et al., Plant Cell 13:1165–1178, (2001).

Units, prefixes, and symbols can be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. The terms defined below are more fully defined by reference to the specification as a whole.

modified: measurably different from wild-type functional properties: include but not limited to: solubility, water absorption and binding, viscosity, gelation (including gel firmness, translucence, and gelation temperature), cohesion-adhesion, elasticity, emulsification, fat adsorption, flavor-binding, foaming and color control. See Kinsella, J. E., J. Am. Oil Chem. Soc. 56:242–258 (1979).

expression cassette: a set of control sequences including initiation, promoter, and termination sequences which function in a plant cell when they flank a structural gene in the proper reading frame. Expression cassettes frequently and preferably contain an assortment of restriction sites suitable for cleavage and insertion of any desired structural gene.

solubility: dispensability in fluid as measured by the nitrogen solubility index (NSI) or protein dispersibility index (PDI). See Johnson, D. W., Food Prod. Dev. 3:78 (1970); and J. Am. Oil Chem. Soc. 47:402 (1970), herein incorporated by reference. The solubility of a protein solution can be measured by incubation for the desired time in the desired conditions, centrifuging at 17,000 g for 10 minutes, and assaying the supernatant for protein content.

gel-forming or gelation: the ability of protein to form a three-dimensional matrix of intertwined, partially associated polypeptides in which water can be held. See Kinsella, J. E., J. Am. Oil Chem. Soc. 56:242–258 (1979); herein incorporated by reference.

emulsifying or emulsification: the ability of protein to aid the uniform formation and stabilization of fat emulsions. See Kinsella, J. E., J. Am. Oil Chem. Soc. 56:242–258, (1979); herein incorporated by reference.

operably linked: A first nucleic acid sequence is operably linked with a second nucleic acid sequence when the first nucleic acid sequences is placed in a functional relationship with the second nucleic acid sequence. For example, a promoter is operably linked to a coding sequence if the promoter affects the transcription or expression of the coding sequence. Generally, operably linked DNA sequences are contiguous and, where necessary, join two protein-coding regions in the same reading frame. With respect to polypeptides, two polypeptide sequences can be operably linked by covalent linkage, such as through peptide bonds or disulfide bonds. Additionally, nucleic acid and polypeptide sequences can be operably linked through a linker sequence. Such linker sequences provide flexibility and spacing, or facilitates construction of expression cassettes, while maintaining desired function.

soybean protein product: a soy flour, a concentrate, or an isolate and products made with soy flours, concentrates, or isolates. (Kinsella, J. E., J. Am. Oil Chem. Soc. 56:242–258 (1979).

By "encoding" or "encoded", with respect to a specified nucleic acid, is meant comprising the information for translation into the specified protein. A nucleic acid encoding a protein can comprise non-translated sequences (e.g., introns) within translated regions of the nucleic acid, or can lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, can be used when the nucleic acid is expressed therein.

By "non-human host cell" is meant a cell which contains a vector and supports the replication and/or expression of the vector. Host cells can be prokaryotic cells such as *E. coli*, or eukaryotic cells such as yeast, insect, amphibian, or mammalian cells excluding humans. Preferably, host cells are monocotyledonous or dicotyledonous plant cells.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide" and "peptide" are used interchangeably herein to refer to a polymer of amino acid residues. A protein can contain one or more polypeptides. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation, deamidation, cross-linking, and ADP-ribosylation. It will be appreciated, as is well known and as noted above, that polypeptides are not always entirely linear. For instance, polypeptides can be branched as a result of ubiquitination, and they can be circular, with or without branching, generally as a result of posttranslation events, including natural processing event and events brought about by human manipulation which do not occur naturally. Circular, branched and branched circular polypeptides can be synthesized by non-translation natural process and by entirely synthetic methods, as well. Further, this invention contemplates the use of both the methionine-containing and the methionine-less amino terminal variants of the protein of the invention.

The term "residue" or "amino acid residue" or "amino acid" are used interchangeably herein to refer to an amino acid that is incorporated into a protein, polypeptide, or peptide (collectively "protein"). The amino acid can be a naturally occurring amino acid and, unless otherwise limited, can encompass non-natural analogs of natural amino acids that can function in a similar manner as naturally occurring amino acids.

"Terminal fusions of a glycinin polypeptide" refer to the N and C termini present before cleavage by VPE, as opposed to new termini formed at the VPE cleavage site.

As used herein, "transgenic plant" includes reference to a plant which comprises within its genome a non-native polynucleotide. Generally, the non-native polynucleotide is stably integrated within the genome such that the polynucleotide is passed on to successive generations. The non-native polynucleotide can be integrated into the genome alone or as part of a recombinant expression cassette. "Transgenic" is used herein to include any cell, cell line, callus, tissue, plant part or plant, the genotype of which has been altered by the presence of a non-native nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides can also be employed in the methods disclosed herein. Thus, the DNA constructs of the present invention encompass all nucleotide constructs that can be employed in the methods of the present invention including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

The isolated nucleic acids of the present invention can be made using (a) standard recombinant methods, (b) synthetic techniques, or combinations thereof. The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation or detection of the translated polypeptide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences can be added to such cloning and/or expression sequences to optimize their function in cloning and/or expression, to aid in isolation of the polynucleotide, or to improve the introduction of the polynucleotide into a cell.

Use of cloning vectors, expression vectors, adapters, and linkers is well known and extensively described in the art. For a description of various nucleic acids see, for example, Stratagene Cloning Systems, current catalog, (La Jolla, Calif.); Amersham Life Sciences, Inc, current catalog, (Arlington Heights, Ill.), and Novagen, Inc. current catalog, (Madison, Wis.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries can be performed by methods well known to those of ordinary skill in the art.

The sequences of the invention are provided in expression cassettes for expression in the plant of interest. The cassette will include 5' and 3' regulatory sequences operably linked to a soybean glycinin nucleic acid sequence.

The cassette can additionally contain at least one additional gene to be cotransformed into the organism. Alternatively, the additional gene(s) can be provided on multiple expression cassettes.

The expression cassette will include in the 5'–3' direction of transcription, a transcriptional and translational initiation region, a DNA sequence of the invention, and a transcriptional and translational termination region functional in plants. The transcriptional initiation region, the promoter, can be native or analogous or foreign or heterologous to the plant host. Additionally, the promoter can be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

A number of promoters can be used in the practice of the invention. The promoters can be selected based on the desired timing, localization and level of expression genes encoding enzymes in a plant. Constitutive, seed-preferred, germination-preferred, tissue-preferred and chemical-regulatable promoters can be used in the practice of the invention. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810–812); rice actin (McElroy et al. (1990) Plant Cell 2:163–171); ubiquitin (Christensen et al. (1989) Plant Mol. Biol. 12:619–632 and Christensen et al. (1992) Plant Mol. Biol. 18:675–689); pEMU (Last et al. (1991) Theor. Appl. Genet. 81:581–588); MAS (Velten et al. (1984) EMBO J. 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The methods of the invention are useful for producing modified glycinins in seeds. Toward this end, the coding sequences for the proteins of the invention can be utilized in expression cassettes or DNA constructs with seed-preferred promoters, seed-development promoters (those promoters active during seed development), as well as seed-germination promoters (those promoters active during seed germination). For dicots, such seed-preferred promoters include, but are not limited to, those from the following genes: glycinin, phaseolin, napin, β-conglycinin, soybean lectin, Kunitz trypsin inhibitor, and the like.

To achieve the desired subcellular location of a protein, sequence encoding a signal peptide can be included in the expression cassette. For example, DNA sequence encoding the signal peptide of preproglycinin can be operably linked to the DNA sequence encoding the proglycinin fusion of interest.

The termination region can be native with the transcriptional initiation region, can be native with the operably linked DNA sequence of interest, or can be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. (1989) Nucleic Acids Res. 17:7891–7903; and Joshi et al. (1987) Nucleic Acid Res. 15:9627–9639.

Additional sequence modifications are known to enhance gene expression in a cellular host. These include elimination of sequences encoding spurious polyadenylation signals, exon-intron splice site signals, transposon-like repeats, and other such well-characterized sequences that can be deleterious to gene expression. The G-C content of the sequence can be adjusted to levels average for a given cellular host, as calculated by reference to known genes expressed in the host cell. When possible, the sequence is modified to avoid predicted hairpin secondary mRNA structures.

The expression cassettes can additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126–6130); potyvirus leaders, for example, TEV leader (Tobacco Etch Virus) (Gallie et al. (1995) Gene 165(2):233–238), MDMV leader (Maize Dwarf Mosaic Virus) (Virology 154:9–20), and human immunoglobulin heavy-chain binding protein (BiP) (Macejak et al. (1991) Nature 353:90–94); untranslated leader from the coat protein mRNA of alfalfa mosaic virus (AMV RNA 4) (Jobling et al. (1987) Nature 325:622–625); tobacco mosaic virus leader (TMV) (Gallie et al. (1989) in Molecular Biology of RNA, ed. Cech (Liss, N.Y.), pp. 237–256); and maize chlorotic mottle virus leader (MCMV) (Lommel et al. (1991) Virology 81:382–385). See also, Della-Cioppa et al. (1987) Plant Physiol. 84:965–968. Other methods known to enhance translation can also be utilized, for example, introns, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction, annealing, resubstitutions, e.g., transitions and transversions, can be involved.

It is further recognized that the components of the expression cassette can be modified to increase expression. For example, truncated sequences, nucleotide substitutions or other modifications can be employed. See, for example Perlak et al. (1991) Proc. Natl. Acad. Sci. USA 88:3324–3328; Murray et al. (1989) Nucleic Acid Res. 17:477–498; and WO 91/16432.

The method of transformation/transfection is not critical to the instant invention; various methods of transformation or transfection are currently available. As newer methods are available to transform crops or other host cells they can be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection can be employed.

Transformation protocols can vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320–334), electroporation (Riggs et al. (1986) Proc. Natl. Acad. Sci. USA 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) EMBO J. 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923–926). Also see Weissinger et al. (1988) Ann. Rev. Genet. 22:421477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Finer and McMullen (1991) In Vitro Cell Dev. Biol. 27P: 175–182 (soybean); Singh et al. (1998) Theor. Appl. Genet. 96:319–324 (soybean); Datta et al. (1990) Biotechnology 8:736–740 (rice); Klein et al. (1988) Proc. Natl. Acad. Sci. USA 85:43054309 (maize); Klein et al. (1988) Biotechnology 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (cereals); Bytebier et al. (1987) Proc. Natl. Acad. Sci. USA 84:5345–5349 (Liliaceae); De Wet et al. (1985) in The Experimental Manipulation of Ovule Tissues, ed. Chapman et al. (Longman, N.Y.), pp. 197–209 (pollen); Kaeppler et al. (1990) Plant Cell Reports 9:415–418 and Kaeppler et al. (1992) Theor. Appl. Genet 84:560–566 (whisker-mediated transformation); D'Halluin et al. (1992) Plant Cell 4:1495–1505 (electroporation); Li et al. (1993) Plant Cell Reports 12:250–255 and Christou and Ford (1995) Annals of Botany 75:407413 (rice); Osjoda et al. (1996) Nature Biotechnology 14:745–750 (maize via *Agrobacterium tumefaciens*); all of which are herein incorporated by reference.

The cells that have been transformed can be grown into plants in accordance with conventional ways. See, for example, McCormick et al. (1986) Plant Cell Reports 5:81–84. These plants can then be grown, and either pollinated with the same transformed strain or different strains, and the resulting hybrid having constitutive expression of the desired phenotypic characteristic identified. Two or more generations can be grown to ensure that expression of the desired phenotypic characteristic is stably maintained and inherited and then seeds harvested to ensure expression of the desired phenotypic characteristic has been achieved.

Using the nucleic acids of the present invention, one can express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Additionally, nucleotide sequences of the invention can be used in methods for producing modified glycinin in host organisms other than plants, including but not limited to bacteria, yeasts and other fungi. Useful host organisms for modified glycinin production include Actinomycetes (e.g., *Streptomyces* sp. and *Nocardia* sp.); bacteria (e.g., *Alcaligenes* (e.g., *A. eutrophus*), *Bacillus cereus*, *B. subtilis*, *B. licheniformis*, *B. megaterium*, *Escherichia coli*, *Klebsiella* (e.g., *K. aerogenes* and *K. oxytoca*), *Lactobacillus*, *Methylomonas*, *Pseudomonas* (e.g., *P. putida* and *P. fluorescens*); fungi (e.g., *Aspergillus*, *Cephalosporium*, and *Penicillium*); and yeast (e.g., *Saccharomyces*, *Rhodotorula*, *Candida*, *Hansenula*, and *Pichia*).

It is expected that those of skill in the art are knowledgeable in the numerous expression systems available for expression of a nucleic acid encoding a protein of the present invention.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a promoter to direct transcription, a ribosome binding site for translational initiation, and a transcription/translation terminator. One of skill will recognize that modifications can be made to a protein of the present invention without diminishing its biological activity. Some modifications can be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Prokaryotic cells can be used as hosts for expression. Prokaryotes most frequently are represented by various strains of *E. coli*; however, other microbial strains can also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al., Gene 22:229–235 (1983); Mosbach et al., Nature 302:543–545 (1983)).

The proteins of this invention, recombinant or synthetic, can be purified to substantial purity by standard techniques well known in the art, including detergent solubilization, selective precipitation with such substances as ammonium sulfate, column chromatography, immunopurification methods, and others. See, for instance, R. Scopes, Protein Purification: Principles and Practice, Springer-Verlag: New York (1982); Deutscher, Guide to Protein Purification, Academic Press (1990). For example, antibodies can be raised to the proteins as described herein. Purification from *E. coli* can be achieved following procedures described in U.S. Pat. No. 4,511,503. The protein can then be isolated from cells expressing the protein and further purified by standard protein chemistry techniques as described herein.

Detection of the expressed protein in all in vivo systems is achieved by methods known in the art and include, for example, radioimmunoassays, Western blotting techniques or immunoprecipitation.

The following examples are offered by way of illustration and not by way of limitation.

EXAMPLES

Description and Isoelectric Points of Glycinin Fusions

Examples of fusions to proglycinin1 (encoded by the Gy1 gene) for expression in *E. coli* are listed in the accompanying table. Similar fusions can be made with other proglycinins or with proglycinin homologs (such as those listed in FIG. 2B of Adachi et al, Proc. Natl. Acad. Sci. USA 10:100, 7395–7400 (2003). The isoelectric points (pI) were calculated by using Vector NTI software (InforMax, Inc., Gaithersburg, Md.). Further descriptions of some of the fusions follow the table. When the fusions are expressed in *E. coli*, the start methionine is often not retained (pET System Manual, Novagen, Inc., Madison, Wis.).

TABLE 1

Proglycinin Fusions. The residues are fused to the core sequence of proglycinin1. The core sequence is SREQP . . . [464 amino acids] . . . KRAVA. The sequence of the 464 amino acids is identical to the corresponding "G1" sequence of Nielsen et al, Plant Cell 1:313–328 (1989), except that the sequence used here has L, rather than I, at position 278 of the published sequence.

| Name | N-terminal Fusion | C-terminal Fusion | Property of underlined residues. | Calculated pI of entire fusion. | Expressed in *E. coli*. |
|---|---|---|---|---|---|
| WT (wild type proglycinin1 used for *E. coli* expression) | MG | — | — | 5.8 | yes |
| KRGly | MAKRKRKRGS | | Basic | 6.8 | yes |
| GlyKR | MG | GGGSKRKRKR | Basic | 6.8 | yes |
| KRGlyKR | MAKRKRKRGS | GGGSKRKRKR | Basic | 8.6 | yes |
| DEGly | MADEDEDEGS | | Acidic | 5.3 | yes |
| GlyDE | MG | GGGSDEDEDE | Acidic | 5.3 | yes |
| DEGlyDE | MADEDEDEGS | GGGSDEDEDE | Acidic | 5.0 | yes |
| KEGly | MAKEKEKEGS | | 3 basic/3 acidic | 5 8 | yes |
| GlyKE | MG | GGGSKEKEKE | 3 basic/3 acidic | 5.8 | no |
| KEGlyKE | MAKEKEKEGS | GGGSKEKEKE | 3 basic/3 acidic | 5.8 | no |
| SQGly | MASQSQSQGS | | Hydrophilic but uncharged | 5.8 | yes |
| GlySQ | MG | GGGSSQSQSQ | Hydrophilic but uncharged | 5.8 | yes |
| SQGlySQ | MASQSQSQGS | GGGSSQSQSQ | Hydrophilic but uncharged | 5.8 | yes |
| AGly | MAAAAAAGS | | Weakly hydrophobic | 5.8 | yes |
| GlyA | MG | GGGSAAAAAA | Weakly hydrophobic | 5.8 | no |
| AGlyA | MAAAAAAGS | GGGSAAAAAA | Weakly hydrophobic | 5.8 | no |
| IGly | MAIIIIIIGS | | Strongly hydrophobic | 5.8 | yes |
| GlyI | MG | GGGSIIIIII | Strongly hydrophobic | 5.8 | no |
| IGlyI | MAIIIIIIGS | GGGSIIIIII | Strongly hydrophobic | 5.8 | no |
| ThioGly | Soybean thioredoxin. | | Acidic | 5.4 | yes |
| GlyThio | MG | Soybean thioredoxin. | Acidic | 5.4 | no |

TABLE 1-continued

Proglycinin Fusions. The residues are fused to the core sequence of proglycinin1.
The core sequence is SREQP . . . [464 amino acids] . . . KRAVA. The sequence of the
464 amino acids is identical to the corresponding "G1" sequence of Nielsen et al,
Plant Cell 1:313–328 (1989), except that the sequence used here has L, rather than
I, at position 278 of the published sequence.

| Name | N-terminal Fusion | C-terminal Fusion | Property of underlined residues. | Calculated pl of entire fusion. | Expressed in E. coli. |
|---|---|---|---|---|---|
| LEAGly | Late embryogenesis abundant protein. | | Basic | 6.3 | no |
| GlyLEA | | Late embryogenesis abundant protein. | Basic | 6.3 | no |
| GlyBHL8 | MG | BHL8 | Basic | 8.2 | yes |
| GlyBHL9 | MG | BHL9 | Basic | 6.5 | no |
| Gly—Gly | Proglycinin1 fusion with itself. | — | | 5.8 | yes |
| Gly-aCG | Proglycinin1 fusion with mature α subunit of β-Conglycinin | — | | 5.1 | no |
| DEGlyKR | MADEDEDEGS | GGGSKRKRKR | Acidic N terminal; basic C terminal. | 5.8 | yes |
| KRGlyDE | MAKRKRKRGS | GGGSDEDEDE | Basic N terminal; acidic C terminal. | 5.8 | no |
| GlyKR(4 basic) | MG | GGGSKRKR | Basic | 6.3 | yes |
| GlyKR(2 basic) | MG | GGGSKR | Basic | 6.0 | yes |
| GlyKR(no linker) | MG | KRKRKR | Basic | 6.8 | no |
| ThioGlyDE | Soybean thioredoxin. | GGGSDEDEDE | Acidic | 5.2 | yes |
| acgeGlyDE | Extension region of mature α subunit of β-Conglycinin | GGGSDEDEDE | Acidic | 4.7 | no |
| GlyF6 | MG | GGGSFFFFFF | Aromatic | 5.8 | no |
| GlyF4 | MG | GGGSFFFF | Aromatic | 5.8 | no |
| GlyF2 | MG | GGGSFF | Aromatic | 5.8 | no |

BHL8 (Barley High Lysine Protein 8) and BHL9 (Barley High Lysine Protein 9) are derivatives of barley chymotrypsin inhibitor-2 (CI-2) that were previously engineered for a high essential amino acid content to improve the nutritional value of maize and other crops (Roesler and Rao; 2000, Protein Sci. 9:1642–1650); (Roesler and Rao; 2001, J. Agric. Food Chem. 49:3443–3451). The 4$^{th}$ residue of the BHL8 used in the present work differs from the BHL8 reported in Roesler and Rao (2000). The amino acid at this position was isoleucine in the present study, methionine in the published BHL8, and leucine in wild type CI-2, and there are a wide variety of other residues at this position in CI-2 homologs. The position of this substitution is position 20 according to the numbering of the above Roesler and Rao (2000) reference. The soybean thioredoxin used here was inactivated by mutating an active site cysteine at position 41 to serine. The LEA protein used here is also known as seed maturation protein PM30 (Chow et al.; Plant Physiol. 121: 1054 (1999); Accession number AF117884). It includes 6 repeats of 11 amino acids in its sequence. For the LEAGly fusion, two asn residues near the C-terminus of LEA were mutated to gln—the 2nd to the last and the 5th to the last residues. For the GlyLEA fusion, no substitutions in the LEA protein were used. Short linkers (SEQ ID NO: 19) were included for the fusions with BHL8, and LEA.

Expression of Fusions in E. coli and Purification

The recombinant protein expression system used for E. coli is the pET System (Novagen). The DNA sequences encoding any desired glycinin fusions could be obtained by ordering them from a commercial vendor such as The Midland Certified Reagent Company (Midland, Tex.). However, most of the fusions described here were made as follows. Polymerase chain reaction with the wild type DNA was performed to add a BamH1 restriction site (encoding glycine-serine) at the 5' end to facilitate N-terminal fusions, or alternatively, to add sequence at the 3' end encoding two glycines followed by a BamH1 site encoding glycine-serine, to facilitate C-terminal fusions. The short peptide N terminal fusions of Table 1 were prepared by annealing pairs of synthetic oligonucleotides that encoded the desired peptide and gave overhangs suitable for ligating into the Nco I site that encodes the start methionine, and the BamH1 site. The short peptide C terminal fusions of Table 1 were prepared by annealing pairs of synthetic oligonucleotides that encoded the desired peptide and gave overhangs suitable for ligating into the BamH1 site and a Hind III site in the pET expression vector downstream from the stop codon. To make fusions at both terminii, a fragment containing the N-terminal fusion was ligated to a fragment containing the C-terminal fusion at an Nde I site in the glycinin gene. Annealed oligonucleotides were not used for the larger protein fusions such as thioredoxin, BHL8, or the LEA protein. Rather, polymerase chain reaction was performed to create appropriate terminii for ligation.

Using the names of Table 1, the proglycinin fusion proteins KRGly, GlyKR, KRGlyKR, DEGly, GlyDE, DEGlyDE, SQGly, GlySQ, SQGlySQ, KEGly, AGly, IGly, GlyBHL8, ThioGly, Gly—Gly, DEGlyKR, GlyKR(4 basic), GlyKR(2 basic) and wild type were expressed in *E. coli* as the proglycinin form using the pET 28 expression vector (Novagen) and most were purified by a combination of ion exchange chromatography and isoelectric precipitation. Some flexibility in expression methods was observed, with both 37° C. and 30° C. incubation temperatures being used successfully, both 2X YT and LB media being used successfully, and with BL21 (DE3), BL21-Codon Plus (DE3)-RP, and BL21-Codon Plus (DE3)-RIL (Stratagene) *E. coli* strains being used successfully. The procedure for GlyKR is described in detail as a typical example, and then Table 2 will summarize differences among the fusion protein preps with respect to lysis buffers and purification conditions.

The GlyKR protein was expressed at 37° C. in 2X YT media with *E. coli* strain BL21-CodonPlus(DE3)-RP (Stratagene). Total volume was 800 ml in a 2.8 liter baffled shake flask. Induction was at OD600=0.8 with 1 mM IPTG and cells were harvested 3 to 4 hours later and frozen. The cells were thawed and lysed in 40 ml of 50 mM Hepes (pH 8.0), 2 mM EDTA, 300 mM NaCl, 0.1% Triton X-100, 0.1 mg/ml lysozyme for 30 min at 25° C. Alternatively, the NaCl concentration was changed midway through the lysis period (150 mM NaCl was used initially, then increased to 300 mM NaCl for the remainder of the lysis period). DNA was sheared by sonication. Centrifugation was done at 17,000 g 15 min. The supernatant was poured through one layer of Miracloth and then purified by SP Sepharose cation exchange chromatography. The protein was applied to an SP Sepharose column equilibrated with 10 mM sodium phosphate, 300 mM NaCl, pH 7.0, and washed with the same buffer. Elution was with 10 mM sodium phosphate, 500 mM NaCl, pH 7.0. The eluted protein was then precipitated by dialysis overnight in 5 mM Tris, pH 8.0. The precipitated protein was centrifuged 17,000 g 10 min, the pellet was washed with dialysis buffer, and the pelleted protein was resuspended in 10 mM sodium acetate, 500 mM NaCl, pH 5.0. The still insoluble material was removed by centrifugation. If needed, a final purification by Superose 6 gel permeation chromatography in the same buffer was done. The purified fusion protein was concentrated by Centricon-30 ultrafiltration and stored either at 4° C. or by freezing in liquid nitrogen without glycerol. The protein concentration was determined by amino acid analysis, and the absorbance at 280 nm of the same protein solution was taken to determine the extinction coefficient for future use. Alternatively, the protein was quantitated by the method of Bradford, using the Coomassie Plus® reagent from Pierce, with Bovine Serum Albumen as standard. A summary of purification conditions appropriate for the fusions that have already been expressed and purified is presented in Table 2.

TABLE 2

Lysis buffers and purification methods

| Protein | Lysis buffer (in addition to 2 mM EDTA, 0.1% Triton X-100, and 0.1 mg/ml lysozyme) | Material and buffer for ion exchange chromatography. (Sepharose is abbreviated Seph) | Buffers for isoelectric precipitation | Buffers for gel permeation chromatography (if needed) |
|---|---|---|---|---|
| KRGly | 50 mM Hepes, 300 mM NaCl, pH 8. | SP Seph; 10 mM sodium phosphate, pH 7, 300–600 mM NaCl | 5 mM Tris, pH 8 | 10 mM sodium acetate, 500 mM NaCl, pH 5 |
| GlyKR | 50 mM Hepes, 300 mM NaCl, pH 8. | SP Seph; 10 mM sodium phosphate, pH 7, 300–500 mM NaCl | 5 mM Tris, pH 8 | 10 mM sodium acetate, 500 mM NaCl, pH 5 |
| KRGlyKR | 50 mM Hepes, 300 mM NaCl, pH 8. | SP Seph; 10 mM sodium phosphate, pH 7, 600–1000 mM NaCl | 5 mM Tris, pH 8 | 10 mM sodium acetate, 500 mM NaCl, pH 5 |
| DEGly | 50 mM Tris, 200 mM NaCl, pH 8 | Q Seph; 20 mM Tris, pH 8, 200–350 mM NaCl | 2 mM Mes, pH 5.5 | 10 mM Tris, 500 mM NaCl, pH 8 |
| GlyDE | 50 mM Tris, 250 mM NaCl, pH 8 | Q Seph; 20 mM Tris, pH 8, 250–350 NaCl | 2 mM Mes, pH 5.5 | 10 mM Tris, 500 mM NaCl, pH 8 |
| DEGlyDE | 50 mM Tris, 150 mM NaCl, pH 8 | Q Seph; 20 mM Tris, pH 8, 250–350 mM NaCl | 2 mM sodium acetate, pH 5 | 10 mM Tris, 500 mM NaCl, pH 8 |
| KEGly | 50 mM Tris, 150 mM NaCl, pH 8 | Q Seph; 20 mM Tris pH 8, 150–250 mM NaCl | 2 mM Mes, pH 6.0 | 10 mM Tris, 500 mM NaCl, pH 8 |

TABLE 2-continued

Lysis buffers and purification methods

| | | | | |
|---|---|---|---|---|
| SQGly | 50 mM Tris, 150 mM NaCl, pH 8 | Q Seph; 20 mM Tris pH 8, 150–250 mM NaCl | 2 mM Mes, pH 6.0 | 10 mM Tris, 500 mM NaCl, pH 8 |
| GlySQ | 50 mM Tris, 150 mM NaCl, pH 8 | Q Seph; 20 mM Tris pH 8, 150–250 mM NaCl | 2 mM Mes, pH 6.0 | 10 mM Tris, 500 mM NaCl, pH 8 |
| SQGlySQ | 50 mM Tris, 150 mM NaCl, pH 8 | Q Seph; 20 mM Tris pH 8, 150–250 mM NaCl | 2 mM Mes, pH 6.0 | 10 mM Tris, 500 mM NaCl, pH 8 |
| DEGlyKR | 50 mM Hepes, 300 mM NaCl, pH 8 | SP Seph; 10 mM sodium phosphate, pH 7, 400–500 mM NaCl. | Not done, but 5 mM Tris, pH 8.0 should work. | 10 mM sodium acetate, 500 mM NaCl, pH 5 |
| GlyKR(4 basic) | 50 mM Hepes, 300 mM NaCl, pH 8 | SP Seph; 10 mM sodium phosphate, pH 7, 300–500 mM NaCl. | 2 mM Mes, pH 6.0. | 10 mM sodium acetate, 500 mM NaCl, pH 5 |
| GlyKR(2 basic) | 50 mM Hepes, 100 mM NaCl, pH 8 | SP Seph; 10 mM sodium phosphate, pH 7, 100–300 mM NaCl. | 2 mM Mes, pH 6.0. | 10 mM sodium acetate, 500 mM NaCl, pH 5 |
| ThioGly | 50 mM Tris, 150 mM NaCl, pH 8 | Q Seph; 20 mM Tris pH 8, 150–250 mM NaCl | 2 mM Mes, pH 5.5 | 10 mM Tris, 500 mM NaCl, pH 8 |
| GlyBHL8 | 50 mM Hepes, 200 mM NaCl, pH 8 | SP Seph; 10 mM sodium phosphate, pH 7, 200–400 mM NaCl. | 5 mM Tris, pH 8 | 10 mM sodium acetate, 500 mM NaCl, pH 5 |
| Wild type proglycinin 1 | 50 mM Tris, 150 mM NaCl, pH 8 | Q Seph; 20 mM Tris pH 8, 150–250 mM NaCl | 2 mM Mes, pH 6.0 | 10 mM Tris, 500 mM NaCl, pH 8 |

Solubility

Using the names of Table 1, the proglycinin fusion proteins KRGly, GlyKR, KRGlyKR, DEGly, GlyDE, DEGlyDE, SQGly, GlySQ, SQGlySQ, KEGly, DEGlyKR, GlyKR(4 basic), GlyKR(2 basic), Gly-BHL8, Thio-Gly, and wild type were expressed in *E. coli* as the proglycinin (trimeric, unprocessed) form, purified, and characterized with respect to solubility. The purified proteins were incubated in 20 mM buffer, 20 mM NaCl for 16 hours at 25° C. at a concentration of 0.5 mg/ml protein. Following centrifugation at 17,000 g for 10 min., the supernatant was assayed for soluble protein using the method of Bradford with the Coomassie Plus reagent (Pierce) and bovine serum albumen as standard. The buffers used were Caps for pH 11.5, 11, 10.5, 10.0, and 9.5; Tris for pH 9.0 and 8.5; Hepes for pH 8, 7.5, and 7; Mes for pH 6.5, 6, and 5.5; and sodium acetate for pH 5, 4.5, 4, and 3.5. The basic fusions KRGly, GlyKR, KRGlyKR, GlyKR(4 basic), and GlyBHL8 had significantly greater solubility than wild type proglycinin1 at pH 3.5 to pH 5.5. For example, at pH 5.5, the wild type proglycinin was 19% soluble, while KRGlyKR was 93% soluble. These basic fusions also had less solubility than wild type from pH 6.5 to pH 10.0. Thus, fusion of basic residues to proglycinin1 had a major impact on solubility. The GlyKR(2 basic) protein also had increases in solubility at pH 3.5 to pH 5.5, and decreases in solubility at pH 6.5 to 10.0, but the changes were smaller than those observed for the other basic fusions. The acidic fusions DEGly, GlyDE, DEGlyDE, and ThioGly had solubility minima at pH 5.0 or 5.5, clearly different than the wild type solubility minimum at pH 6.0. This shift in the solubility curve resulted in greater than wild type solubility for the acidic fusions at pH 6.0, 6.5, and 7.0. Thus, fusion of acidic residues to proglycinin1 had a significant effect on solubility. The net neutral fusion KEGly (3 basic and 3 acidic residues in the fused peptide), and the neutral fusions SQGly, GlySQ, and SQGlySQ all had solubility minima at pH 6.0 like wild type, yet some had greater than wild type solubility from pH 4.0 to pH 5.0. The observation that fusing as few as 6 basic or 6 acidic residues to either terminus of proglycinin1 can result in such major changes in solubility behavior was unexpected.

Gel Firmness

Gel firmness was determined for the purified KRGly, GlyKR, KRGlyKR, DEGly, GlyDE, SQGly, SQGlySQ, GlyBHL8, ThioGly, and wild type proteins following their expression in *E. coli* as the proglycinin (trimeric, unprocessed) form. Gels were formed as follows: The proteins were concentrated by ultrafiltration to 60 mg/ml in 20 mM potassium phosphate, 500 mM NaCl, pH 7. 50 μl of 60 mg/ml protein was transferred to a thin-walled 0.2 ml PCR tube. Samples were sonicated one minute to remove bubbles with a Branson ultrasonic cleaner B-220 (Shelton, Conn., USA). The samples were heated and cooled in a PTC-100 Programmable Thermal Controller from MJ Research, Inc., using the following temperature changes: 50° C. for 2 min; change from 50° to 98° C. at 0.1/sec; hold at 98° C. 5 min; change from 98° to 50° C. at 0.1/sec; hold at 50° C. 2 min. Gel firmness was measured with a TA.XT.Plus Texture Analyzer (Texture Technologies Corp., Scarsdale, N.Y.) using a 2 mm diameter cylindrical probe. The probe was pushed against the gels for a distance of 2 mm, using pre-test and test speeds of 0.5 mm/sec, a post-test speed of 10 mm/sec, and a trigger force of 1.5 grams. The value (force in grams) at 1 mm distance was compared between gels. The gels made from the basic peptide fusions KRGly, GlyKR, and KRGlyKR were less firm than gels made from wild type proglycinin1. In contrast, gels made from the other fusions were more firm than gels made from wild type. For example, values at 1 mm for wildtype, KRGlyKR, and SQGlySQ gels were 20.1, 12.7, and 45.7 grams of force. Thus, fusion of even a few residues to proglycinin markedly changed gelation properties.

Differential Scanning Calorimetry

Differential scanning calorimetry was done to determine the thermal denaturation temperatures for the purified KRGly, GlyKR, KRGlyKR, DEGly, GlyDE, DEGlyDE, SQGly, GlySQ, SQGlySQ, GlyBHL8, ThioGly, and wild type proteins following their expression in E. coli as the proglycinin (trimeric, unprocessed) form. Scans were done from 30° C. to 110° C. at a rate of 90° C./hour, using a VP-DSC Microcalorimeter from MicroCal (Northampton, Mass.). Peak values at the thermal transition were compared. The GlyBHL8 protein had a denaturation temperature of 78.3° C., which was 7.1° C. less than the wild type value of 85.4° C. For the ThioGly protein, two transitions were observed, at 15.5 and 8.6° C. less than the wild type value. The two transitions may be due to independent unfolding of thioredoxin and proglycinin. Denaturation temperatures for the other proteins were all within 3.4° C. of the wild type value. Because denaturation is a prerequisite for gelation, some proglycinin fusions such as GlyBHL8 or ThioGly may form gels at a lower temperature than required for wild type protein gels.

Characterization of oligomeric state

Gel permeation chromatography: Using the names of Table 1, the proglycinin fusion proteins GlyBHL8, ThioGly, KRGly, GlyKR, KRGlyKR, DEGly, GlyDE, DEGlyDE, SQGly, GlySQ, SQGlySQ, and wild type were expressed in E. coli as the unprocessed (trimeric, proglycinin) form, purified, and characterized with respect to oligomeric state. Superose 6 gel permeation chromatography with appropriate molecular mass markers was done with the purified proteins, using 10 mM Tris, 500 mM NaCl, pH 8. The wild type protein eluted at a similar position as the aldolase marker (158,000 mW), consistent with expectations for trimeric proglycinin. All of the fusions eluted at a similar or slightly earlier position than wild type, demonstrating that the fusions also assembled into oligomers.

Proteolytic Stability of Glycinin Fusions

Using the names of Table 1, the proglycinin fusion proteins KRGly, GlyKR, KRGlyKR, DEGly, GlyDE, DEGlyDE, GlyBHL8, ThioGly, and wild type were expressed in E. coli as the proglycinin (trimeric, unprocessed) form, purified, and characterized with respect to stability against digestion by the protease chymotrypsin. The purified proteins were incubated with chymotrypsin at 37° C. for 1, 2, 4, 8, 15, 30 or 60 min. Incubation was done in 100 mM Tris (pH 8.0), 500 mM NaCl, 1 mM $CaCl_2$, with a ratio (wt:wt) of 1:20 chymotrypsin:substrate protein. Results were assessed by SDS-PAGE. The stability against digestion by chymotrypsin was similar for wild type and for all of the glycinin fusions except for ThioGly. The similar proteolytic stability suggested that the fusion proteins were correctly folded, because malfolded proteins would have been more susceptible to the protease. The results of the ThioGly fusion suggest that all or part of the thioredoxin was clipped off by the protease. Incubations with 1:100 trypsin:substrate were also done for GlyBHL8, ThioGly and wild type, and the rate of digestion with this protease was approximately the same for wild type and the two fusion proteins, suggesting that the fusion proteins were correctly folded.

In Planta Expression of Glycinin Fusions and Incorporation into Hexamers

Constructs appropriate for expression in plants were prepared that fused the glycinin1 promoter and signal peptide (both encoded by the Gy1 gene) to the ThioGly protein, the GlyBHL8 protein, the KRGlyKR protein, and the DEGlyDE protein (SEQ ID NOS: 35, 36, 37, 38, 39, 40, 41, 42), followed by the phaseolin 3' non-translated region. Three amino acids of mature glycinin1 (Phe-Ser-Ser) were also included following the signal peptide in the ThioGly, KRGlyKR, and DEGlyDE constructs.

Soybean embryogenic suspension cultures were transformed with the plasmids and DNA fragments by the method of particle gun bombardment (Klein et al., 1987, Nature 327:70). A DuPont Biolistic PDS1000/HE instrument (helium retrofit) was used for all transformations. Protein expression was assessed by western blots. Antibodies against BHL8 were used to detect the GlyBHL8 fusion. The GlyBHL8 protein was highly expressed and stably accumulated in both soybean somatic embryos and mature seeds. Antibodies against wild type proglycinin 1 plus a mobility difference from wild type during SDS-PAGE were used to detect the ThioGly fusion. The ThioGly fusion expressed well in soybean embryos, thus demonstrating that glycinin fusion proteins with either an N or a C terminal fusion could accumulate in plants. Furthermore, the mobility in SDS-PAGE suggested that the fusion proteins were processed by VPE. To assess whether the fusion proteins were incorporated into hexamers, protein fractionation followed by additional western blots was done. Proteins from untransformed or transformed soybean seeds were extracted and fractionated by 6%–22% sucrose density gradients (Gruis et al, Plant Cell 16:270–290 (2004)), and fractions were then assessed by western blots probed with the appropriate antibodies.

The GlyBHL8, and ThioGly were primarily in 11S hexamer fraction based on Coomassie Blue staining and Western blot, confirming that the fusion polypeptides were incorporated into hexamers. Protein solubility analyses indicated that the 11S fraction of the GlyBHL8 soybean seeds provided better solubility than the 11S fraction of the wild type soybean seeds from pH 2.8–6.0. In summary, these results demonstrated that glycinin fusions in plants can accumulate and can be incorporated into hexamers. The glycinin fusions can change the functionality of the soybean seed proteins.

What is claimed is:

1. An isolated terminal fusion polypeptide comprising: a first soybean glycinin or proglycinin polypeptide operably linked to a second polypeptide of SEQ ID NO:12 wherein the resulting terminal fusion polypeptide exhibits modified functional properties.

2. The fusion polypeptide of claim 1 wherein the second polypeptide is operably linked to the C terminus of the first polypeptide.

3. The fusion polypeptide of claim 1 wherein the calculated pI of the fusion polypeptide is from 0.2 to 2.8 pH units greater than the pI of the wild type proglycinin or glycinin polypeptide.

4. A soybean protein product comprising the terminal fusion polypeptide of claim 1.

* * * * *